United States Patent
Havelund et al.

(10) Patent No.: US 11,167,035 B2
(45) Date of Patent: *Nov. 9, 2021

(54) INSULIN COMPOSITIONS AND METHOD OF MAKING A COMPOSITION

(71) Applicant: Novo Nordisk A/S, Bagsvaerd (DK)

(72) Inventors: Svend Havelund, Bagsvaerd (DK); Frantisek Hubalek, Copenhagen (DK); Helle Birk Olsen, Alleroed (DK); Ib Jonassen, Valby (DK); Thomas Hoeg-Jensen, Klampenborg (DK); Anne Plum, Birkeroed (DK); Ulla Ribel-Madsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/332,906

(22) Filed: Jul. 16, 2014

(65) Prior Publication Data

US 2014/0328943 A1 Nov. 6, 2014

Related U.S. Application Data

(63) Continuation of application No. 12/096,476, filed as application No. PCT/EP2006/070104 on Dec. 21, 2006, now abandoned.

(60) Provisional application No. 60/755,915, filed on Jan. 3, 2006.

(30) Foreign Application Priority Data

Dec. 28, 2005 (EP) .................................... 05113021

(51) Int. Cl.
*A61K 9/62* (2006.01)
*A61K 47/52* (2017.01)
*A61K 38/28* (2006.01)
*C07K 14/62* (2006.01)

(52) U.S. Cl.
CPC .............. *A61K 47/52* (2017.08); *A61K 38/28* (2013.01); *C07K 14/62* (2013.01)

(58) Field of Classification Search
CPC ......... A61K 47/52; A61K 38/28; C07K 14/62
See application file for complete search history.

(56) References Cited

U.S. PATENT DOCUMENTS

| | | |
|---|---|---|
| 3,528,960 A | 9/1970 | Haas |
| 3,868,358 A | 2/1975 | Jackson |
| 3,907,676 A | 9/1975 | Jorgensen |
| 4,476,118 A | 10/1984 | Brange et al. |
| 4,652,548 A | 3/1987 | Chance et al. |
| 4,669,430 A | 6/1987 | Reinold et al. |
| 4,764,592 A | 8/1988 | Massey et al. |
| 4,876,322 A | 10/1989 | Budde et al. |
| 4,983,658 A | 1/1991 | Kress et al. |
| 5,008,241 A | 4/1991 | Markussen et al. |
| 5,177,058 A | 1/1993 | Dorschug |
| 5,382,574 A | 1/1995 | Jorgensen |
| 5,605,884 A | 2/1997 | Lee et al. |
| 5,646,242 A | 7/1997 | Baker et al. |
| 5,750,497 A | 5/1998 | Havelund et al. |
| 5,830,999 A | 11/1998 | Dunn |
| 5,866,538 A | 2/1999 | Norup et al. |
| 5,898,067 A | 4/1999 | Balschmidt et al. |
| 5,905,140 A | 5/1999 | Hansen |
| 6,011,007 A | 1/2000 | Havelund et al. |
| 6,174,856 B1 | 1/2001 | Langballe et al. |
| 6,211,144 B1 | 4/2001 | Havelund |
| 6,221,837 B1 | 4/2001 | Ertl et al. |
| 6,251,856 B1 | 6/2001 | Markussen et al. |
| 6,335,316 B1 | 1/2002 | Hughes et al. |
| 6,451,762 B1 * | 9/2002 | Havelund ............. A61K 38/28 514/6.3 |
| 6,451,970 B1 | 9/2002 | Schaffer et al. |
| 6,504,005 B1 | 1/2003 | Fridkin et al. |
| 6,620,780 B2 | 9/2003 | Markussen et al. |
| 6,652,886 B2 | 11/2003 | Ahn et al. |
| 6,869,930 B1 | 3/2005 | Havelund et al. |
| 7,229,964 B2 | 6/2007 | Markussen et al. |
| 7,402,565 B2 | 7/2008 | Kjeldsen et al. |
| 7,544,656 B2 | 6/2009 | Sabetsky |
| 7,615,532 B2 | 11/2009 | Jonassen et al. |
| 8,003,605 B2 | 8/2011 | Bayer et al. |
| 8,067,362 B2 | 11/2011 | Kodra et al. |
| 8,404,645 B2 | 3/2013 | Schlein |
| 8,691,759 B2 | 4/2014 | Madsen et al. |

(Continued)

FOREIGN PATENT DOCUMENTS

| | | |
|---|---|---|
| AU | 2011252127 B2 | 2/2014 |
| CN | 86101489 A | 1/1987 |

(Continued)

OTHER PUBLICATIONS

Lane W. S. et al., High-dose insulin therapy: is it time for U-500 insulin?, Endocrine Practice, 2009, vol. 15, No. 1, pp. 71-79.
Segal a. R. et al., Use of concentrated insulin human regular (U-500) for patients with diabetes, American Journal of Health-System Pharmacy, 2010, vol. 67, No. 18, pp. 1526-1535.
Valentine V., Don't Resist Using U-500 Insulin and Pramlintide for Severe Insulin Resistance, Clinical Diabetes, 2012, vol. 30, No. 2, pp. 80-84.
Obesity Society: Your weight and diabetes—http://www.obesity.org/resources-for/your-weight-and-diabetes.htm, (accessed Jul. 21, 2015).
Inzucchi S. E. et al., Management of hyperglycaemia in type 2 diabetes: a patient-centered approach. Position statement of the American Diabetes Association (ADA) and the European Association for the Study of Diabetes (EASD), Diabetologia, 2012, vol. 55, No. 6, pp. 1577-1596.

(Continued)

*Primary Examiner* — David Browe
(74) *Attorney, Agent, or Firm* — Rosemarie R. Wilk-Orescan

(57) ABSTRACT

The invention is related to insulin compositions with a high content of zinc atoms per six molecules of acylated insulin. The insulin is an acylated insulin and may be mixed with a further insulin analogue such as the rapid acting insulin Asp B28 human insulin.

7 Claims, 7 Drawing Sheets

(56) References Cited

U.S. PATENT DOCUMENTS

| | | | |
|---|---|---|---|
| 8,722,620 B2 | 5/2014 | Fynbo et al. |
| 8,796,205 B2 | 8/2014 | Jonassen et al. |
| 8,828,923 B2 | 9/2014 | Jonassen et al. |
| 8,933,021 B2 | 1/2015 | Hubalek et al. |
| 8,962,794 B2 | 2/2015 | Madsen et al. |
| 9,034,818 B2 | 5/2015 | Poulsen et al. |
| 9,045,560 B2 | 6/2015 | Madsen et al. |
| 9,447,163 B2 | 9/2016 | Mollerup et al. |
| 9,481,721 B2 | 11/2016 | Naver et al. |
| 9,603,904 B2 | 3/2017 | Johansen et al. |
| 9,688,737 B2 | 6/2017 | Madsen et al. |
| 9,839,579 B2 | 12/2017 | Weeks et al. |
| 9,884,094 B2 | 2/2018 | Johansen et al. |
| 10,137,172 B2 | 11/2018 | Johansen et al. |
| 2002/0045731 A1 | 4/2002 | Schaffer et al. |
| 2002/0155994 A1 | 10/2002 | Havelund et al. |
| 2003/0004096 A1 | 1/2003 | Boderke |
| 2003/0236196 A1 | 12/2003 | Kerwin et al. |
| 2004/0006000 A1 | 1/2004 | Langkjaer |
| 2004/0116345 A1 | 6/2004 | Besman et al. |
| 2004/0138099 A1 | 7/2004 | Draeger |
| 2005/0054818 A1 | 3/2005 | Brader et al. |
| 2005/0074866 A1 | 4/2005 | Grancha et al. |
| 2005/0222006 A1 | 10/2005 | Havelund et al. |
| 2005/0232899 A1 | 10/2005 | Balwani et al. |
| 2006/0183668 A1 | 8/2006 | Jonassen et al. |
| 2008/0076705 A1 | 3/2008 | Kodra et al. |
| 2009/0074882 A1 | 3/2009 | Havelund et al. |
| 2009/0137454 A1 | 5/2009 | Fynbo et al. |
| 2009/0239785 A1 | 9/2009 | Hubalek et al. |
| 2009/0312236 A1 | 12/2009 | Beals et al. |
| 2010/0009899 A1 | 1/2010 | Jonassen et al. |
| 2010/0167990 A1 | 7/2010 | Poulsen et al. |
| 2011/0152185 A1 | 6/2011 | Plum et al. |
| 2011/0230402 A1 | 9/2011 | Johansen et al. |
| 2011/0301081 A1 | 12/2011 | Becker et al. |
| 2013/0261051 A1 | 10/2013 | Johansen |
| 2014/0073759 A1 | 3/2014 | Mollerup et al. |
| 2014/0349925 A1 | 11/2014 | Jonassen et al. |
| 2015/0126439 A1 | 5/2015 | Johansen et al. |
| 2015/0250857 A1 | 9/2015 | Andresen et al. |
| 2016/0058840 A1 | 3/2016 | Johansen et al. |
| 2016/0296602 A1 | 10/2016 | Johansen |
| 2017/0165327 A1 | 6/2017 | Andresen et al. |
| 2017/0319664 A1 | 11/2017 | Johansen |
| 2018/0125946 A1 | 5/2018 | Johansen |
| 2019/0112348 A1 | 4/2019 | Madsen et al. |
| 2019/0160155 A1 | 5/2019 | Johansen |
| 2019/0194285 A1 | 6/2019 | Olsen et al. |
| 2021/0060132 A1 | 3/2021 | Andresen et al. |

FOREIGN PATENT DOCUMENTS

| | | | |
|---|---|---|---|
| CN | 88102311 A | 11/1988 |
| CN | 1829738 A | 9/2006 |
| CN | 101389650 A | 12/2006 |
| CN | 101454019 A | 6/2009 |
| DE | 1212679 B | 3/1966 |
| EP | 214826 A2 | 3/1987 |
| EP | 315968 A1 | 5/1989 |
| EP | 375437 A2 | 6/1990 |
| EP | 383472 A2 | 8/1990 |
| EP | 420649 A2 | 4/1991 |
| EP | 818204 A2 | 1/1998 |
| EP | 925792 A2 | 6/1999 |
| EP | 1153608 A1 | 11/2001 |
| EP | 884053 B1 | 10/2002 |
| EP | 1283051 A1 | 2/2003 |
| EP | 0894095 | 5/2003 |
| EP | 0785713 B1 | 9/2003 |
| EP | 1595544 A1 | 11/2005 |
| EP | 2107069 A2 | 10/2009 |
| EP | 1951198 B1 | 6/2010 |
| EP | 2264065 A2 | 12/2010 |
| EP | 2264066 A2 | 12/2010 |
| EP | 2275439 A2 | 1/2011 |
| EP | 2287184 A2 | 2/2011 |
| EP | 2387989 A2 | 11/2011 |
| EP | 2389945 A1 | 11/2011 |
| EP | 2505593 A1 | 10/2012 |
| GB | 1042194 A | 9/1966 |
| GB | 1492997 | 11/1977 |
| JP | B S36-11994 | 7/1961 |
| JP | 38005689 | 5/1963 |
| JP | B S38-5689 | 5/1963 |
| JP | 1254699 | 5/1979 |
| JP | 57-067548 A | 4/1982 |
| JP | 02101022 | 4/1990 |
| JP | H09502867 | 3/1997 |
| JP | H10509176 | 8/1998 |
| JP | 11-502110 | 2/1999 |
| JP | 2000-501419 A | 2/2000 |
| JP | 2000-504732 A | 4/2000 |
| JP | 2000-515542 | 11/2000 |
| JP | 2001-518915 A | 10/2001 |
| JP | 2001-518916 A | 10/2001 |
| JP | 2001-521004 A | 11/2001 |
| JP | 2001-521006 A | 11/2001 |
| JP | 2001-521904 A | 11/2001 |
| JP | 2001-526225 A | 12/2001 |
| JP | 2002-527487 A | 8/2002 |
| JP | 2002-308899 A | 10/2002 |
| JP | 2002-543092 A | 12/2002 |
| JP | 2004-523589 A | 8/2004 |
| JP | 2006-511441 A | 4/2006 |
| JP | 2006-519253 | 8/2006 |
| JP | 2007-523881 | 8/2007 |
| JP | 2009-522231 | 6/2009 |
| JP | 4808785 B2 | 11/2011 |
| JP | 4959005 B2 | 6/2012 |
| JP | 5026567 B2 | 9/2012 |
| JP | 5331071 B2 | 10/2013 |
| RU | 2160118 C2 | 12/2000 |
| RU | 2164520 C2 | 3/2001 |
| RU | 2317821 C2 | 2/2008 |
| RU | 2352581 C2 | 4/2009 |
| WO | 91/09617 A1 | 7/1991 |
| WO | 91/12817 A1 | 9/1991 |
| WO | 9307922 A1 | 4/1993 |
| WO | 93/12812 A1 | 7/1993 |
| WO | 95/07931 A1 | 3/1995 |
| WO | 95/32730 A1 | 12/1995 |
| WO | 96/10417 A1 | 4/1996 |
| WO | 96/29344 | 9/1996 |
| WO | 97/04801 A1 | 2/1997 |
| WO | 97/31022 A1 | 8/1997 |
| WO | 98/02460 A1 | 1/1998 |
| WO | 98/05361 A2 | 2/1998 |
| WO | 98/42367 A1 | 10/1998 |
| WO | 98/42368 A1 | 10/1998 |
| WO | 98/47529 A1 | 10/1998 |
| WO | 99/21573 | 5/1999 |
| WO | 99/21578 | 5/1999 |
| WO | 99/21888 A1 | 5/1999 |
| WO | 99/22754 | 5/1999 |
| WO | 99/24071 A1 | 5/1999 |
| WO | 99/32116 A1 | 7/1999 |
| WO | 00/23098 A1 | 4/2000 |
| WO | 00/43034 A2 | 7/2000 |
| WO | 00/64940 | 11/2000 |
| WO | 2001/49314 A2 | 7/2001 |
| WO | 02076495 A1 | 10/2002 |
| WO | 2003/002136 A2 | 1/2003 |
| WO | 03/013573 | 2/2003 |
| WO | 03030829 A2 | 4/2003 |
| WO | 03/0053339 A2 | 7/2003 |
| WO | 03/053339 A2 | 7/2003 |
| WO | 03/094951 A1 | 11/2003 |
| WO | 03/094956 A1 | 11/2003 |
| WO | 2004/039392 A2 | 5/2004 |
| WO | 2004/112828 A1 | 12/2004 |
| WO | 2005/005477 A2 | 1/2005 |
| WO | 2005/012347 A2 | 2/2005 |
| WO | 2005/016365 A2 | 2/2005 |

(56) References Cited

FOREIGN PATENT DOCUMENTS

| | | |
|---|---|---|
| WO | 2005/021022 A2 | 3/2005 |
| WO | 2005/47508 A1 | 5/2005 |
| WO | 2005/063298 A1 | 7/2005 |
| WO | 2005/089722 A1 | 9/2005 |
| WO | 2005/117948 A1 | 12/2005 |
| WO | 2006/008238 A1 | 1/2006 |
| WO | 2006/020720 A2 | 2/2006 |
| WO | 2006/023665 A2 | 3/2006 |
| WO | 06/51103 A2 | 5/2006 |
| WO | 2006/053906 A1 | 5/2006 |
| WO | 2006/079019 A2 | 7/2006 |
| WO | 2006/082204 | 8/2006 |
| WO | 2006/082205 | 8/2006 |
| WO | 2007/041481 A1 | 4/2007 |
| WO | 2007/074133 A2 | 7/2007 |
| WO | 2007/096431 A1 | 8/2007 |
| WO | 2007/121256 A2 | 10/2007 |
| WO | 2007/128815 A1 | 11/2007 |
| WO | 2007/128817 A2 | 11/2007 |
| WO | 2007/135117 A2 | 11/2007 |
| WO | 2008/034881 A1 | 3/2008 |
| WO | 2008/152106 A1 | 12/2008 |
| WO | 2009/060071 A1 | 5/2009 |
| WO | 2009/063072 A2 | 5/2009 |
| WO | 2010/049488 A1 | 5/2010 |
| WO | 2011141407 A1 | 11/2011 |
| WO | 2012055967 A2 | 5/2012 |
| WO | 2012119007 A1 | 9/2012 |
| WO | 2013037754 A2 | 3/2013 |
| WO | 2013164375 A1 | 11/2013 |

OTHER PUBLICATIONS

Crasto W et al., Insulin U-500 in severe insulin resistance in type 2 diabetes mellitus, Postgraduate Medical Journal, 2009, vol. 85, No. 1002, pp. 219-222.
Heise T et al., Insulin Degludec Has a Two-Fold Longer Half-Life and a More Consistent Pharmacokinetic Profile Than Insulin Glargine, Diabetes, 2011, vol. 60(Suppl 1), LB11, (Abstract 37-LB).
Nosek L. et al., Ultra-Long-Acting Insulin Degludec Has a Flat and Stable Glucose-Lowering Effect, Diabetes 2011, 60(Suppl 1), LB14 (Abstract 49-LB).
Korsatko S. et al., Ultra-Long-Acting Insulin Degludec: Two Different Formulations (U100 and U200) Are Bioequivalent and Show Similar Pharmacodynamics, Diabetes 2011, 60(Suppl 1), A624 (Abstract 2349-PO).
Zinman B. et al., Insulin degludec, an ultra-long-acting basal insulin, once a day or three times a week versus insulin glargine once a day in patients with type 2 diabetes: a 16-week, randomized, open-label, phase 2 trial. The Lancet, 2011, vol. 377, 924-931.
Heller S. et al., Insulin degludec, an ultra-longacting basal insulin, versus insulin glargine in basal-bolus treatment with mealtime insulin aspart in type 1 diabetes (BEGIN Basal-Bolus Type 1): a phase 3, randomised, open-label, treat-to-target non-inferiority trial, The Lancet 2012, vol. 379, pp. 1489-1497.
Garber A. J. et al., Insulin degludec, an ultra-longacting basal insulin, versus insulin glargine in basal-bolus treatment with mealtime insulin aspart in type 2 diabetes (BEGIN Basal-Bolus Type 2): a phase 3, randomised, open-label, treat-to-target non-inferiority trial, The Lancet, 2012, vol. 379, pp. 1498-1507.
Declaration of Helsinki, Ethical principles for medical research involving human subjects., Journal of Indian Medical Association, 2009, vol. 107, No. 6, pp. 403-405.
Defining and Reporting Hypoglycemia in Diabetes: A report from the American Diabetes Association Workgroup on Hypoglycemia, Diabetes Care, 2005, vol. 28, No. 5, pp. 1245-1249.
Humulin® R Regular U-500 (Concentrated), Insulin Human Injection, USP (rDNA Origin), Eli Lilly and Company, Lilly USA, LLC, Indianapolis, IN 46285, USA.
Thornton S. et al., Intravenous overdose of insulin glargine without prolonged hypoglycemic effects, The Journal of Emergency Medicine, 2012, vol. 43, No. 3, pp. 435-437, XP002711646.
Zinman B. et al., Insulin degludec versus insulin glargine in insulin-naive patients with type 2 diabetes: a 1-year, randomized, treat-to-target trial (BEGIN Once long), Diabetes Care, 2012, vol. 35, No. 12, pp. 2464-2471, XP9172018.
Rodbard H et al., Reduced risk of hypoglycaemia with insulin degludec vs insulin glargine in patients with type 2 diabetes requiring high doses of basal insulin: meta-analysis of five randomized trials. Presented as an oral at the AACE 21st Annual Scientific and Clinical Congress, Philadelphia, PA, 2012, (Abstract 241).
ICH Harmonised Tripartite Guideline: Guideline for Good Clinical Practice, Journal of postgraduate medicine, 2001, vol. 47, No. 3, pp. 199-203.
Marcus A., Diabetes care—insulin delivery in a changing world, The Medscape Journal of Medicine, 2008, vol. 10, No. 5, 120.
Hoevelmann U. et al., Insulin degludec 200 U/ml is ultra-lang-acting and has a flat and stable glucose-lowering effect, Diabetologia, 2012, vol. 55, No. Suppl. 1, pp. 5374-5375, XP002723769 & 48th Annual Meeting of the European-Association-For-The-Study-Of-Diabetes; Berlin, Germany; Oct. 1-5, 2012.
Wang F. et al., Insulin degludec as an ultralong-acting basal insulin once a day: a systematic review, Diabetes, Metabolic Syndrome and Obesity: Targets and Therapy, 2012, vol. 5, pp. 191-204, XP002723770.
Korsatko S. et al., Ultra-long-acting insulin degludec: bioequivalence and similar pharmacodynamics shown for two different formulations (U100 and U200), Diabetologia, 2011, vol. 54, No. Suppl. 1, XP002723771, p. S427, & 47th Annual Meeting of the European-Association-For-The-Study-Of-Diabetes (EASD); Lisbon, Portugal; Sep. 12-16, 2011.
Barnett, A.H., "A Review of Basal Insulins," Diabet Med, 2003, vol. 20, No. 11, pp. 873-885.
Brussels: International Diabetes Federation, IDF Clinical Guidelines Task Force, Guideline for Management of Postmeal Glucose, 2007, pp. 1-32, http://www.idf.org/webdata/docs/Guideline_PMG_final.pdf.
Brussels: International Diabetes Federation, IDF Clinical Guidelines Task Force, Global Guideline for Type 2 Diabetes, 2005, pp. 1-82, http://www.idf.org/webdata/docs/IDF%20GGT2D.pdf.
Definition of Moiety From http://dictionary.reference.com/browse/moiety, 2010, pp. 1-3.
English Language Abstract for JP 57-067548, published Apr. 24, 1982.
English Language Abstract for JP 1-254699, published Oct. 11, 1989.
English Language Machine Translation of CN101389650, published Mar. 18, 2009.
Irie et al., "Pharmacokinetics and Pharmacodynamics of Single Dose Insulin Detemir, Long-Acting Soluble Insulin Analogue Compared to NPH Insulin in Patients With Type 1 Diabetes Mellitus", J Clin Ther Med, 2007, vol. 23, No. 5, pp. 349-356.
Machine Translation of JP 2006-519253, published Aug. 24, 2006.
Machine Translation of JP 2007-523881, published Aug. 23, 2007.
Schlichtkrull, J., "Insulin Crystals", Acta Chemica Scandinavica, 1956, vol. 10, No. 9, pp. 1455-1458.
Vajo et al., "Genetically Engineered Insulin Analogs: Diabetes in the New Millennium," Pharma Rev, 2000, vol. 52, No. 1, pp. 1-9.
Whittingham, J.L. et al., "Crystallographic and Solution Studies of N-Lithocholyl Insulin: A New Generation of prolonged-Acting Human Insulins", Biochemistry, 2004, vol. 42, pp. 5987-5995.
Brange, J et al Diabetic Medicine Neutral Insulin Solutions Physically Stabilized by Addition of ZN2+, 1986, vol. 3, No. 6, pp. 532-536.
English abstract for JP2004523589.
English abstract for JP2002527487.
English abstract for JP2001518915.
English abstract for DE1212679.
Havelund, S. et al., "The Mechanism of Protraction of Insulin Detemir, a Long-Acting, Acylated Analog of Human Insulin", Pharmaceutical Research, 2004, vol. 21, No. 8, pp. 1498-1504.
Nathan, D. M. et al., "Management of Hyperglycemia in Type 2 Diabetes: A Consensus Algorithm for the Initiation and Adjustment of Therapy," Diabetes Care, 2008, vol. 31, No. 1, pp. 173-175.

(56) References Cited

OTHER PUBLICATIONS

Heise, T. et al., "Towards Peakless, Reproducible and Long-Acting Insulins. An Assessment of the Basal Analogues Based on Isoglycaemic Clamp Studies," Diabetes Obes Metab, 2007, vol. 9, No. 5, pp. 648-659.
Hinds et al., "PEGylated insulin in PLGA microparticles. In vivo and in vitro analysis," Journal of Controlled Release, 2005, vol. 104, No. 3, p. 447-460.
Machine Translation of JP 2000-51554, published Nov. 21, 2000.
Jonassen, I. et al., Pharmaceutical Research 2006, vol. 23, No. 1, pp. 49-55.
Annual Review Endocrine Metabolism 2000, pp. 46-53.
Machine Translation of Japanese Patent 10-509176, published Sep. 8, 1998.
Machine Translation of Japanese Patent 11-502110, published Feb. 23, 1999.
Machine Translation of Japanese Patent 2000-501419, published Feb. 8, 2000.
Machine Translation of Japanese Patent 2000-504732, published Apr. 18, 2000.
Machine Translation of Japanese Patent 2001-521004, published Nov. 6, 2001.
Machine Translation of Japanese Patent 2001-521904, published Nov. 13, 2001.
Machine Translation of Japanese Patent 2002-543092, published Dec. 17, 2002.
Machine Translation of Japanese Patent 2002-308899, published Oct. 23, 2002.
Machine Translation of Japanese Patent 9-502867, published Mar. 25, 1997.
Machine Translation of Japanese Patent 2001-521006, published Nov. 6, 2001.
Abstract of Japanese Patent 57-067548, published Apr. 24, 1982.
Abstract of Japanese Patent 1254699, published Oct. 11, 1989.
Machine Translation CN 101389650, published Mar. 18, 2009.
Machine Translation of JP 2000-515542, published Nov. 21, 2000.
Heller. S R, Current Medical Research and Opinion, "Insulin Analogues", 2002, vol. 18, No. 1, pp. 40-47.
I. Jonassen et al., Diabetologia, "Insulin Degludec: Multi-Hexamer Formation Is the Underlying Basis for This New Generation Ultra-Long Acting Basal Insulin", 2010, vol. 53, No. 1, pp. S388.
R. Cuddihy et al., Diabetologia, "Once-Daily Use of a New Generation Ultra-Long Acting Basal Insulin With a Bolus Boost in Insulin-Naive People With Type 2 Diabetes: Comparison With Insulin Glargine", 2010, vol. 53, No. 1, pp. S389.
Samuel et al. "Studies on the immunogenicity of protamines in humans and experimental animals by means of a micro-complement fixation test." Clin. Exp. Immunol. vol. 33: pp. 252-260. 1978.
Kurtz et al. "Circulating IgG antibody to protamine in patients treated with protamine-insulins." Diabetologica. vol. 25: pp. 322-324. 1983.
Definition of Moiety From http://dictionary.reference.com/browse/moiety, Aug. 26, 2010, p. 1-3.
English abstract for JP2004523589, published Aug. 5, 2004.
English abstract for JP2002527487, published Aug. 27, 2002.
English abstract for JP2001518915, published Oct. 16, 2001.
English abstract for DE1212679, published Mar. 17, 1966.
R. Cuddihy et al., "Once-Daily Use of a New Generation Ultra-Long Acting Basal Insulin With a Bolus Boost in Insulin-Naïve People With Type 2 Diabetes: Comparison With Insulin Glargine", Diabetologia, 2010, vol. 53, No. 1, pp. S389.
Ross SA, et al. Barriers to effective insulin treatment: the persistence of poor glycemic control in type 2 diabetes. Current Medical Research and Opinion 2011, vol. ;27(Suppl 3), pp. 13-20.
Reimer T, et al. Intuitiveness, instruction time, and patient acceptance of a prefilled insulin delivery device and a reusable insulin delivery device in a randomized, open-label, crossover handling study in patients with type 2 diabetes. Clinical Therapeutics. 2008, vol. 30, pp. 2252-2262.

Rubin RR et al.. Factors affecting use of insulin pens by patients with type 2 diabetes. Diabetes Care. 2008 vol. 31 pp. 430-432.
Peyrot M and Rubin RR. Factors associated with persistence and resumption of insulin pen use for patients with type 2 diabetes. Diabetes Technology & Therapeutics. 2011 vol. 13 No. 43-48.
Oyer D,et al. Ease of use and preference of a new versus widely available pre-filled insulin pen assessed by people with diabetes, physicians and nurses. Expert Opinion on Drug Delivery. 2011 vol. ;8, pp. 1259-1269.
Bailey T,et al Usability and preference evaluation of a prefilled insulin pen with a novel injection mechanism by people with diabetes and healthcare professionals. Current Medical Research and Opinion 2011, vol. 27 pp. 2043-2052.
Nadeau DA,et al. Healthcare professional and patient assessment of a new prefilled insulin pen versus two widely available prefilled insulin pens for ease of use, teaching and learning. Current Medical Research and Opinion 2012;vol. 28.No. 1 pp. 3-13.
Lajara R, et al. Healthcare professional and patient perceptions of a new prefilled insulin pen versus vial and syringe. Expert Opinion on Drug Delivery 2012, vol. 9, pp. 1181-1196.
Bailey T, et al. FlexTouch® for the delivery of insulin: technical attributes and perception among patients and healthcare professionals. Expert Review of Medical Devices 2012, vol. 9, pp. 209-217.
Anthony H. Barnett, Diabetic Medicine, A Review of Basal Insulins, 2003, vol. 20, No. 11, pp. 873-885.
Heise, T. et al., Diabetes, Obesity and Metabolism, Towards Peakless, Reproducible and Long-Acting Insulins. An Assessment of the Basal Analogues Based on Isoglycaemic Clamp Studies, 2007, vol. 9, No. 5, pp. 648-659.
IDF Clinical Guidelines Task Force, Brussels: International Diabetes Federation 2005, Global Guideline for Type 2 Diabetes, 2005.
IDF Clinical Guidelines Task Force, Brussels: International Diabetes Federation 2007, Guideline for Management of Postmeal Glucose, 2007.
Nathan, D. M. et al., Diabetes Care, Management of Hyperglycemia in Type 2 Diabetes: A Consensus Algorithm for the Initiation and Adjustment of Therapy, 2008, vol. 31, No. 1, pp. 173-175.
I. Jonassen et al., "Insulin Degludec: Multi-Hexamer Formation is the Underlying Basis for This New Generation Ultra-Long Acting Basal Insulin", Diabetologia, 2010, vol. 53, No. 1, pp. S388
I. Jonassen et al., "Insulin Degludec: Multi-Hexamer Formation is the Underlying Basis for This New Generation Ultra-Long Acting Basal Insulin", Diabetologia, Sep. 2010, vol. 53, No. 1, pp. S388
R. Cuddihy et al., "Once-Daily Use of a New Generation Ultra-Long Acting Basal Insulin With a Bolus Boost in Insulin-Naïve People With Type 2 Diabetes: Comparison With Insulin Glargine", Diabetologia, Sep. 2010, vol. 53, No. 1, pp. S389.
American Diabetes Association,Standards of Medical Care in Diabetes 2012, Diabetes Care 2012,vol. 35(Suppl 1), pp. S11-S63.
American Diabetes Association. Insulin administration. Diabetes Care. 2012 vol. 35, No. 1, pp. S1-S2.
American Diabetes Association. Standards of Medical Care in Diabetes—2014. Diabetes Care. 2014, vol. 37 Suppl 1, pp. S14-S80.
Anderson RM et al. Patient empowerment: results of a randomized controlled trial. Diabetes Care. 1995, vol. 18,No. 7 pp. 943-949.
Barnett et al: Dosing of insulin glargine in the treatment of type 2 diabetes ,Clinical Therapeutics, 2007 vol. 29, No. 6,,pp. 987-999.
Benjamin EM. Self-monitoring of blood glucose: the basics. Clinical Diabetes. 2002, vol. 20, No. 1, pp. 45-47.
Canadian Diabetes Association Clinical Practice Guidelines Expert Committee. Canadian Diabetes Association. Canadian Journal of Diabetes. 2008, vol. 32(Suppl 1)pp. S1-S201.
Davies M, et al.. Improvement of glycemic control in subjects with poorly controlled type 2 diabetes. Diabetes Care. 2005,vol. 28, No. 6, pp. 1282-1288.
Deutsch T et al,Utopia: A Consultation System for Visit-By-Visit Diabetes Management, Medical Informatica. Taylor and Francis.; Basingstoke. GB, 1996, vol. 21, No. 4, pp. 345-358.
Duckworth W. et al.Glucose Control and Vascular Complications in Veterans with Type 2 Diabetes, The new england journal o f medicine, 2009, vol. 360, pp. 129-139.
Gerstein H C et al. A randomized trial of adding insulin glargine vs.avoidance of insulin in people with Type 2 diabetes on either no

(56) References Cited

OTHER PUBLICATIONS oral glucose-lowering agents or submaximal doses of metformin and/or sulphonylureas. The Canadian Insight (Implementing New Strategies with Insulin Glargine for Hyperglycaemia treatment) Study, Diabetic Medicines, 2006, vol. 23, No. 7, pp. 736-742.
Holman RR et al.,10-Year Follow-up of Intensive Glucose Control in Type 2 Diabetes,The New England Journal of Medicine, 2008, vol. 359, pp. 1577-1589.
Holman RR et al.A practical guide to Basal and Prandial Insulin therapy, Diabetic Medicine, 1985, vol. 2, pp. 45-53.
International Diabetes Federation Clinical Guidelines Task Force. Global Guideline for Type 2 Diabetes. 2005. Available at: http://www.idf.org/webdata/docs/IDF%20GGT2D.pdf. Accessed Dec. 19, 2012.
Inzucchi SE et al.Management of Hyperglycemia in Type 2 Diabetes: A Patient-Centered Approach: Position Statement of the American Diabetes Association (ADA) and the European Association for the Study of Diabetes (EASD),Diabetes care, 2012, vol. 35, pp. 1364-1379.
Iwamoto Yasuhi Ko et al: Insulin degludec in Japanese patients with type 1 diabetes mellitus: A randomized controlled trial,Journal of Diabetes Investigation,2013,vol. 4, No. 1, pp. 62-68.
Janka Hans U et al, Combination of oral antidiabetic agents with basal insulin; versus premixed insulin alone in randomized elderly patients with type 2 diabetes mellitus, Journal of the American Geriatrics Society, 2007,vol. 55, No. 2, pp. 182-188.
Kulzer B, et al. Effects of self-management training in type 2 diabetes: a randomized, prospective trial. Diabetic Medicine. 2007, vol. 24, No. 4, pp. 415-423.
LANTUS® (insulin glargine [rDNA origin] injection). sanoti-aventis U.S. LLC, Bridgewater, NJ, USA; 2007. Health Care Professional. Dosing & Titration. Available at: http://www.lantus.com/hcp/titration.aspx. Accessed Nov. 13, 2012.
Liebl A, et al. Direct costs and health-related resource utilisation in the 6 months after insulin initiation in German patients with type 2 diabetes mellitus in 2006: INSTIGATE study. Current Medical Research Opinion 2008,vol. 24, No. 8, pp. 2349-2358.
Meneghini L et al., The usage of a simplified self-titration dosing guideline (303 Algorithm) for insulin detemir in patients with type 2 diabetes-results of the randomized, controlled Predictive TM 303 study. Diabetes Obesity and Metabolism. 2007, vol. 9, pp. 902-913.
Nathan DM et al,Intensive Diabetes Treatment and Cardiovascular Disease in Patients with Type 1 Diabetes,The new england journal of medicine, 2005, vol. 353, No. 25, pp. 2643-2653.
Nathan DM et al.Management of Hyperglycemia in Type 2 Diabetes: A Consensus Algorithm for the Initiation and Adjustment of Therapy: Update regarding thiazolidinediones: a consensus statement from the American Diabetes Association and the European Association for the Study of Diabetes. Diabetes Care, 2008, vol. 31, No. 1, pp. 173-175.
Nathan DM et al.The Effect of Intensive Treatment of Diabetes on the Development and Progression of Long-Term Complications in Insulin-Dependent Diabetes Mellitus,the Diabetes Control and Complications Trial Research Group,The New England Journal of medicine, 1993, vol. 329, No. 14, pp. 977-986.
Norris SL, et al. Self-management education for adults with type 2 diabetes: a meta-analysis on the effect of glycemic control. Diabetes Care, 2002, vol. 25, No. 7, pp. 1159-1171.
Ohkubo Y et al. Intensive insulin therapy prevents the progression of diabetic microvascular complications in Japanese patients with non-insulin-dependent diabetes mellitus: a randomized prospective 6-year study,Diabetes Research and Clinical Practice, 1995, vol. 28, No. 2 pp. 103-117.
Peyrot M, et al. Factors associated with injection omission/non-adherence in the Global Attitudes of Patients and Physicians in Insulin Therapy Study. Diabetes Obesity and Metabolism. 2012,vol. 14, pp. 1081-1087.
Peyrot M, et al.. Insulin adherence behaviours and barriers in the multinational Global Attitudes of Patients and Physicians in insulin therapy study. Diabetic Medcine. 2012,vol. 29, No. 5, pp. 682-689.

Philis-Tsimikas A et al.: Insulin degludec once-daily in type 2 diabetes:; Simple or step-wise titration (BEGIN: Once Simple Use), Advances in Therapy, 2013,vol. 30, No. 6, pp. 607-622.
Sakharova O V et al.Effects on post-prandial glucose and AGE precursors from two initial insulin strategies in patients with Type 2 diabetes uncontrolled by oral agents, Journal of Diabetes and Its Complications,2012,vol. 26, No. 4, pp. 333-338.
Schnell O, et al. Consensus statement on self-monitoring of blood glucose in diabetes. Diabetes, Stoffwechsel and Herz. 2009, vol. 4, pp. 285-289.
Selvin E et al,.Meta-Analysis: Glycosylated Hemoglobin and Cardiovascular Disease in; Diabetes Mellitus, Annals of internal medicine,2004, vol. 141, pp. 421-431.
The Advance Collaborative Group, Patel A et al.Intensive Blood Glucose Control and Vascular Outcomes in Patients with Type 2 Diabetes, The new England Journal of Medicine, 2008, vol. 358, pp. 2560-2572.
UK Prospective Diabetes Study (UKPDS) Group, Intensive blood-glucose control with sulphonylureas or insulin compared with conventional treatment and risk of complications in patients with type 2 diabetes (UKPDS 33)., Lancet, 1998, vol. 352 (9131), pp. 837-853.
Yeaw J, et al.Cost of self-monitoring of blood glucose in Canada among patients on an insulin regimen for diabetes. Diabetes Therapeutics . Epub ,2012 vol. 3, No. 7, pp. 1-17 doi: 10.1007/s13300-012-0007-6.
Yeaw J, et al. Self-monitoring blood glucose test strip utilization in Canada. Diabetes. 2012;vol. 61(Suppl 1)p. A35.
Yeaw J, et al.. Cost of self-monitoring of blood glucose in the United States among patients on an insulin regimen for diabetes. Journal of Managed Care Pharmacy 2012, vol. 18, No. 1, pp. 21-32.
American Diabetes Association. Insulin administration. Diabetes Care. 2002 vol. 25: pp. S112-S115.
Heise T, et al.. Insulin degludec: four times lower pharmacodynamic variability than insulin glargine under steady-state conditions in type 1 diabetes. Diabetes Obesity and Metabolism , 2012, vol. 14, pp. 859-864.
Heise T, et al. Insulin degludec 200 U/mL is ultra-long-acting and has a flat and stable glucose-lowering effect. Diabetes.2012;, vol. 61(Suppl.1) p. A91.
Korsatko S, et al. Ultra-long-acting insulin degludec: bio-equivalence and similar pharmacodynamics shown for two different formulations (U100 and U200). Diabetologia. 2011 , vol. 54(Suppl. 1) p. S427.
World Medical Association. World Medical Association Declaration of Helsinki: Ethical principles for medical research involving human subjects—Last amended by the 59th WMA General Assembly, Seoul. 2008. Available at: http://www.wma.net/en/30publications/10policies/b3/17c.pdf. Accessed Sep. 14, 2015.
International Conference on Harmonisation. ICH Harmonised Tripartite Guideline:Guideline for Good Clinical Practice. E6 (R1), Step 4. 1996. Available at: http://www.ich.org/fileadmin/Public_Web_Site/ICH_Products/Guidelines/Efficacy/E6_R1/Step4/E6_R1_Guideline.pdf. Accessed Sep. 14, 2015.
Niskanen L, et al. Randomized, multinational, open-label, 2-period, crossover comparison of biphasic insulin aspart 30 and biphasic insulin lispro 25 and pen devices in adult patients with type 2 diabetes mellitus. Clinical Therapeutics 2004, vol. 26 pp. 531-540.
Garg S, et al. Preference for a new prefilled insulin pen compared with the original pen. Current Medical Research & Opinion. 2011 vol. 27 pp. 2323-2333.
Garber AJ, et al; on behalf of the NN1250-3582 BEGINTM BB T2D trial investigators. Insulin degludec, an ultra-long acting basal insulin, versus insulin glargine in basal-bolus treatment with meal-time insulin aspart in type 2 diabetes (BEGINTM Basal-Bolus Type 2): a phase 3, randomised, open-label, treat-to-target non-inferiority trial. Lancet.2012, vol. 379, pp. 1498-1507.
Zinman B, et al; on behalf of the NN1250-3579 BEGIN tm Once Long trial investigators. Insulin degludec versus insulin glargine in insulin-naïve patients with type 2 diabetes: a 1-year, randomized, treat-to-target trial (BEGIN tm Once Long). Diabetes Care. 2012 vol. 35 pp. 2464-2471.

(56) References Cited

OTHER PUBLICATIONS

Bergenstal R, Bhargava A, Jain RK, et al; on behalf of the NN1250-3672 BEGIN TM Low Volume trial investigators. 200 U/ml insulin degludec improves glycemic control similar to insulin glargine with a low risk of hypoglycemia in insulin-naïve people with type 2 diabetes. Abstract 207. http://am.aace.com/2012/sites/all/files/abstract-061812.pdf. Accessed Jan. 19, 2013.
Onishi Y, et al. Superior glycaemic control with once daily insulin degludec/ insulin aspart versus insulin glargine in Japanese adults with type 2 diabetes inadequately controlled on oral drugs: a randomized, controlled phase 3 trial. Diabetes Obesity and Metabolism. 2013 vol. 15, pp. 826-832.
Rakel RE. Improving patient acceptance and adherence in diabetes management: a focus on insulin therapy. Advances in Therapy. 2009, vol. 26 pp. 838-846.
Talboys Catalog, 2008 Laboratory Equipment Catalog, Talboys by Troemner, 122 pages (2008).
Heise et al "Lower Within-Subject Variability of Insulin Detemir in Comparison to NPH Insulin an Insulin Glargine in People with Type 1 Diabetes" Diabetes, 2004, vol. 53, pp. 1614-1620.
Novo Nordisk, Levemir Product Information, Jun. 16, 2005. 42 pages.
"America Pink", http://america.pink/insulin-degludec_2091149.html, downloaded Aug. 24, 2016.
L. Heinemann and J. H. Anderson Jr. Diabetes Technol Ther 6 (5):698-728, 2004.
Living with Diabetes, available at http://www.diabetes.org/living-with-diabetes/treatment-and-care/medication/?loc=lwd-slabnav, accessed on Jan. 5, 2017.
WebMD "What is a unit of insulin," available at http://answers.webmd.com/answers/1196453/what-is-a-unit-of-insulin.
else et al., "Insulin Degludec 200 U/mL is Ultra-Long Acting and Has a Flat and Stable Glucose-Lowering Effect," Canadian Journal of Diabetes, 2012, vol. 36, No. 6, p. S13.
Springer et al., "Management of Type 2 Diabetes Mellitus in Children and Adolescents", Pediatrics, 2013, vol. 131, No. 2, pp. e648-e664.
Heise et al., "Ultra-Long-Acting Insulin Degludec has a Flat and Stable Glucose-Lowering Effect in Type 2 Diabetes," Diabetes, Obesity and Metabolism, 2012, vol. 14, pp. 944-950.
Heller et al., "Insulin Degludec, an Ultra-Longacting Basal Insulin, Versus Insulin Glargine . . . : a Phase 3, Randomized, Open-Label, Treat-to-Target Non-Inferiority Trial," The Lancet, 2012, vol. 379, pp. 1489-1497.
Tambascia et al., "Degludec: the new ultra-long insulin analogue," Diabetology Metabol. Synd., 2015, vol. 7, pp. 1-7.
Brange "Stability of Insulin", 1994, Kluwer Academic Publishers BV, pp. 30-31.
Birkeland et al."Insulin degludec in type 1 diabetes: a randomized controlled trial of a new-generation ultra-long-acting insulin compared with insulin glargine." Diabetes Care, Mar. 2011, vol. 34, No. 3, p. 661-665.
Briscoe et al.,"Hypoglycemia in type 1 and type 2 diabetes: physiology, pathophysiology, and management." Clinical diabetes, Jul. 2006, vol. 24, No. 3, pp. 115-121.
U.S. Appl. No. 16/463,594, filed May 23, 2019.

\* cited by examiner aspart 300 µM / LysB$^{29}$-N$^\varepsilon$-hexadecandioyl-γ-Glu desB30 human insulin 600 µM, 4.5 Zn/6acyl-ins Aspart 180 µM/LysB$^{29}$-N$^\varepsilon$-hexadecandioyl-γ-Glu desB30 human insulin 420 µM, 8.6 Zn/6acyl-ins

INSULIN COMPOSITIONS AND METHOD OF MAKING A COMPOSITION

CROSS-REFERENCE TO RELATED APPLICATIONS

This application is a continuation of application Ser. No. 12/096,476, filed Oct. 21, 2008, which is a 35 U.S.C. § 371 national stage application of International Patent Application PCT/EP2006/070104, filed Dec. 21, 2006, which claimed priority of European Patent Application 05113021.9, filed Dec. 28, 2005; this application further claims priority under 35 U.S.C. § 119 of U.S. Provisional Application 60/755,915, filed Jan. 3, 2006.

FIELD OF THE INVENTION

The present invention relates to pharmaceutical compositions of acylated insulin with a prolonged action profile and high zinc content. Further the invention relates to a method for producing a composition with a prolonged action profile and high zinc content and a method for manufacturing a composition for the treatment of diabetes.

BACKGROUND OF THE INVENTION

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of a long acting insulin to cover the basal insulin requirement supplemented by bolus injections of a rapid acting insulin to cover the insulin requirement related to meals.

Long acting insulin compositions are well known in the art. Thus, one main type of long acting insulin compositions comprises injectable aqueous suspensions of insulin crystals or amorphous insulin. In these compositions, the insulin compounds utilized typically are protamine insulin, zinc insulin or protamine zinc insulin.

Certain drawbacks are associated with the use of insulin suspensions. Thus, in order to secure an accurate dosing, the insulin particles must be suspended homogeneously by gentle shaking before a defined volume of the suspension is withdrawn from a vial or expelled from a cartridge. Also, for the storage of insulin suspensions, the temperature must be kept within more narrow limits than for insulin solutions in order to avoid lump formation or coagulation.

While it was earlier believed that protamines were non-immunogenic, it has now turned out that protamine insulin crystals can be immunogenic in man and that their use for medical purposes may lead to formation of antibodies. Also, evidence has been found that the protamine crystal is itself immunogenic. Therefore, with some patients the use of long acting insulin compositions containing protamines must be avoided.

Another type of long acting insulin compositions are solutions having a pH value below physiological pH from which the insulin will precipitate because of the rise in the pH value when the solution is injected. A drawback with these solutions is that the particle size distribution of the precipitate formed in the tissue on injection, and thus the release profile of the medication, depends on the blood flow at the injection site and other parameters in a somewhat unpredictable manner. A further drawback is that the solid particles of the insulin may act as a local irritant causing inflammation of the tissue at the site of injection.

Insulin is a 51 amino acid peptide hormone produced in the islets of Langerhans in the pancreas. Its primary function, acting as a monomer, is to facilitate the transport of glucose molecules across the cell membranes of adipose and muscle tissue by binding to and activating a transmembrane receptor.

A distinctive property of insulin is its ability to associate into hexamers, in which form the hormone is protected from chemical and physical degradation during biosynthesis and storage. X-ray crystallographic studies on insulin show that the hexamer consists of three dimers related by a 3-fold axis of rotation. These dimers are closely associated through the interaction of two zinc ions at its core positioned on the 3-fold axis.

When human insulin is injected into the subcutis in the form of a high-concentration pharmaceutical formulation it is self associated, and here dissociation into monomers is relatively slow. Hexamers and dimers of insulin are slower to penetrate capillary wall than monomers.

Zinc and phenolic additives are regularly used in therapeutic insulin preparations to promote hexamer formation as a precaution against degradation during storage. In this form, however, the action of injected insulin is delayed while the hexamers diffuse through the subcutis and dissociate into dimers and monomers.

Formulations of insulin are usually prepared by dissolving insulin in a small volume of water under acidic conditions. Zinc is then added to the formulation followed by a neutralisation and addition of preservatives like phenol and m-cresol. The pharmaceutical formulation of these insulins are given as about 2, 3 or 4 zinc atoms per hexamer insulin.

WO 2005/012347 discloses another group of acylated insulin derivatives comprising additional negatively charge compared to the acylated insulins disclosed in WO 95/07931. The pharmaceutical formulation of these acylated insulins are given as 2, 3 or 4 zinc atoms per hexamer insulin.

WO 2003/094956 disclose stable insulin formulations prepared by mixing a monomeric insulin and a soluble acylated insulin analogue. The formulations contains from about 2.3 to about 4.5 $Zn^{2+}$ per hexamer insulin. The acylated insulin analogue according to this invention is insulin detemir.

From WO 2003/094951 it is known to formulate a stable soluble insulin formulation having both fast and long action. The formulation has a content of zinc in the range from about 2.3 to about 4.5 $Zn^{2+}$ per hexamer insulin. The acylated insulin analogue according to this invention is insulin detemir.

WO 99/21888 concerns aggregates of human insulin derivatives, which contains up to 5 zinc atoms per 6 molecules of insulin derivate.

Human insulin has three primary amino groups: the N-terminal group of the A-chain and of the B-chain and the ε-amino group of $Lys^{B29}$. Several insulin derivatives which are substituted in one or more of these groups are known in the prior art. Thus, U.S. Pat. No. 3,528,960 (Eli Lilly) relates to N-carboxyaroyl insulins in which one, two or three primary amino groups of the insulin molecule has a carboxyaroyl group.

EP 894095 discloses insulin derivatives wherein the N-terminal group of the B-chain and/or the ε-amino group of Lys in position B28, B29 or B30 has a substituent of the formula —CO—W—COOH where W can be a long chain hydrocarbon group. These insulin derivatives have a prolonged profile of action and are soluble at physiological pH values.

WO 95/07931 discloses protracted insulin derivatives wherein a liphophilic side chain is attached either to the α-amino group of the N-terminal amino acid residue of the B chain or to the ε-amino group of a Lys residue present in the B chain of the parent insulin.

The mechanism behind slow absorption of insulin detemir has been studied by Havelund et al. (The mechanism of protraction of insulin detemir, a long-acting acylated analog of human insulin., Pharmaceutical Research, 21 (2004) 1498-1504). Insulin formulations are prepared by adding 2 zinc atoms per hexamer insulin followed by glycerol, phenol, m-cresol and sodium phosphate.

In Whittingham et al (Crystallographic and solution studies of N-Lithocholyl insulin: a new generation of prolonged-acting human insulin, Biochemistry 2004, 43, 5987-5995) a formulation of acylated insulin analogue is prepared. The insulin formulation is prepared by adding 2-2.5 zinc atoms per hexamer insulin followed by glycerol and phenol. The structures of the insulin is measured by size exclusion chromatography.

The present invention is related to certain pharmaceutical compositions of acylated insulins which solves the problems of the prior art.

SUMMARY OF THE INVENTION

The present invention is related to a soluble pharmaceutical composition comprising an acylated insulin comprising more than 4 zinc atoms per 6 molecules of the acylated insulin.

The zinc content may be up to about 12 zinc atoms per 6 molecules of acylated insulin. The upper limit for the zinc content is the content of zinc which would cause precipitation of the insulin and turning the solution into a suspension.

In one aspect of the invention the pharmaceutical composition comprises between about 4.3 and about 12 zinc atoms per 6 molecules of acylated insulin or between about 4.5 and about 12 zinc atoms per 6 molecules of acylated insulin. In a further aspect of the invention the pharmaceutical composition comprises between about 5 and about 11.4 zinc atoms per 6 molecules of acylated insulin or between about 5.5 and about 10 zinc atoms per 6 molecules of acylated insulin. In a further aspect the pharmaceutical composition comprises between about 6 and about 10.5 zinc atoms per 6 molecules of acylated insulin or the pharmaceutical composition comprises between about 6.5 and about 10 zinc atoms per 6 molecules of acylated insulin or the pharmaceutical composition comprises between about 7 and about 9 zinc atoms per 6 molecules of acylated insulin. In a further aspect the pharmaceutical composition comprises citrate from about one third to about 3 times the zinc concentration.

The insulin molecules of the present invention associate with each other to form complexes comprising zinc. These insulin-zinc complexes can be present in the pharmaceutical formulation as hexamers, dodecamers or complexes with a higher molecular weight than dodecamers. All kinds of insulin form complexes with zinc, eg. Human insulin, acylated insulin (insulin derivatives) and insulin analogues.

In one aspect of the invention at least 85% of the acylated insulin is present as complexes which are acylated insulin dodecamers or complexes with a higher molecular weight than acylated insulin dodecamer.

In one aspect of the invention at least 90, 92, 95, 96, 97, 98, 99 or 99.5% of the acylated insulin is present as complexes which are acylated insulin dodecamers or complexes with a higher molecular weight than acylated insulin dodecamer.

In one aspect of the invention, the pharmaceutical composition comprises a surfactant. The surfactant can be present in an amount of 0.0005-0.01% based on the weight of the pharmaceutical composition. In one aspect the surfactant can be present in an amount of 0.0005-0.007% based on the weight of the composition. An example of a surfactant could be polysorbate 20, which can be present in the composition in an amount of 0.001-0.003% based on the weight of the composition. Another example is poloxamer 188, which can be present in an amount of 0.002-0.006% based on the weight of the composition.

The insulin molecule may be acylated at various positions in the insulin molecule. In one aspect the insulin is acylated in the ε-amino group of a Lys residue in a position in the B-chain of the parent insulin molecule in particularly in the ε-amino group of the B29 lysine group in the human insulin molecule. However, according to other aspects of the invention the acylation may take place in another position in the insulin molecule, e.g. the α-amino group in position B1 or in position where the natural amino acid residue in the insulin molecule has been substituted with a lysine residue provided that B29 is changed from a lysine to another amino acid residue.

Thus in one aspect the acylated insulin is acylated either in the α-amino group in the B1 position or in a free ε-amino group of a lysine residue in the A- or B-chain of the insulin molecule.

In one aspect the insulin is acylated in the free ε-amino group of the lysine residue in position B29 of the insulin molecule.

The acyl group will be a liphophilic group and will typically be a fatty acid moiety having from about 6 to about 32 carbon atoms comprising at least one free carboxylic acid group or a group which is negatively charged at neutral pH. The fatty acid moiety will more typically have from 6 to 24, from 8 to 20, from 12 to 20, from 12-16, from 10-16, 10-20, from 14-18 or from 14-16 carbon atoms.

In one aspect the pharmaceutical composition comprises at least one free carboxylic acid or a group which is negatively charged at neutral pH. In one aspect the pharmaceutical composition comprises an acyl group which is derived from a dicarboxylic fatty acid with from 4 to 32 carbon atoms.

In a further aspect the fatty acid moiety is derived from a dicarboxylic fatty acid with from about 6 to about 32, from 6 to 24, from 8 to 20, from 12 to 20, from 12-16, from 10-16, from 10-20, from 14-18 or from 14-16 carbon atoms.

In one aspect the pharmaceutical composition comprises an acyl group which is attached to the insulin via a linker group through amide bonds.

The acyl group may be attached directly to the free amino group in question. However, the acyl group may also be attached via amide bonds by a linker which links the free amino group in the insulin molecule and the acyl group in question together.

The acylated insulin will typically have at least one, or two additional negative net charge compared to human insulin and more typically it will have two additional negative charges. The additional negative charge may be provided by the free carboxylic acid group in the fatty acid or by the linker group which may comprise one ore more amino acid residues of which at least one will contain a free carboxylic acid or a group which is negatively charged at neutral pH. In a further aspect the acyl group is derived from a dicarboxylic fatty acid.

In one aspect the pharmaceutical composition comprises an insulin wherein the insulin has a side chain attached either to the α-amino group of the N-terminal amino acid residue of the B chain or to an ε-amino group of a Lys residue present in the B chain of the parent insulin moiety via an amide bond, which side chain comprises at least one free carboxylic acid group or a group which is negatively charged at neutral pH, a fatty acid moiety with about 4 to about 32 carbon atoms in the carbon chain; and possible one or more linkers linking the individual components in the side chain together via amide bonds.

In one aspect the insulin molecule has a side chain attached to the ε-amino group of a Lys residue present in the B chain of the parent insulin, the side chain being of the general formula:

—W—X—Y—$Z_2$ wherein W is:
  an α-amino acid residue having a carboxylic acid group in the side chain which residue forms, with one of its carboxylic acid groups, an amide group together with ε-amino group of a Lys residue present in the B chain of the parent insulin;
  a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
  a covalent bond from X to an ε-amino group of a Lys residue present in the B chain of the parent insulin;

X is:
  —CO—;
  —CH(COOH)CO—;
  —CO—N(CH$_2$COOH)CH$_2$CO—;
  —CO—N(CH$_2$COOH)CH$_2$CON(CH$_2$COOH)CH$_2$CO—;
  —CO—N(CH$_2$CH$_2$COOH)CH$_2$CH$_2$CO—;
  —CO—N(CH$_2$CH$_2$COOH)CH$_2$CH$_2$CON(CH$_2$CH$_2$COOH)CH$_2$CH$_2$CO—;
  —CO—NHCH(COOH)(CH$_2$)$_4$NHCO—;
  —CO—N(CH$_2$CH$_2$COOH)CH$_2$CO—; or
  —CO—N(CH$_2$COOH)CH$_2$CH$_2$CO—.

that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an ε-amino group of a Lys residue present in the B chain of the parent insulin;

Y is:
  —(CH$_2$)$_m$— where m is an integer in the range of 6 to 32;
  a divalent hydrocarbon chain comprising 1, 2 or 3 —CH=CH— groups and a number of —CH$_2$— groups sufficient to give a total number of carbon atoms in the chain in the range of 10 to 32; and $Z_2$ is:
  —COOH;
  —CO-Asp;
  —CO-Glu;
  —CO-Gly;
  —CO-Sar;
  —CH(COOH)$_2$;
  —N(CH$_2$COOH)$_2$;
  —SO$_3$H; or
  —PO$_3$H and any Zn$^{2+}$ complexes thereof, provided that when W is a covalent bond and X is CO, then Z is different from —COOH.

In one aspect the B30 amino acid residue has been deleted and the acylated insulin is a desB30 insulin.

In one aspect W is an α-amino acid residue having from 4 to 10 carbon atoms and in a further aspect W is selected from the group consisting of α-Asp, β-Asp, α-Glu, γ-Glu, α-hGlu and δ-hGlu.

In one aspect X is —CO—.
In one aspect $Z_2$ is —COOH.

The substructure Y of the side chain —W—X—Y—$Z_2$ can be a group of the formula —(CH$_2$)$_m$— where m is an integer in the range of from 6 to 32, from 8 to 20, from 12 to 20, or from 12-16.

In one aspect, Y is a divalent hydrocarbon chain comprising 1, 2 or 3 —CH=CH— groups and a number of —CH$_2$— groups sufficient to give a total number of carbon atoms in the chain in the range of from 6 to 32, from 10 to 32, from 12 to 20, or from 12-16.

In one aspect, Y is a divalent hydrocarbon chain of the formula —(CH$_2$)$_v$C$_6$H$_4$(CH$_2$)$_w$— wherein v and w are integers or one of them is zero so that the sum of v and w is in the range of from 6 to 30, from 10 to 20, or from 12-16.

In a further aspect W is selected from the group consisting of α-Asp, β-Asp, α-Glu, and γ-Glu; X is —CO— or —CH(COOH)CO; Y is —(CH$_2$)$_m$— where m is an integer in the range of 12-18 and $Z_2$ is —COOH or —CH(COOH)$_2$.

Non limiting examples of acylated insulin compounds are N$^{εB29}$—(N$^α$—(HOOC(CH$_2$)$_{14}$CO)-γ-Glu) desB30 human insulin; N$^{εB29}$—(N$^α$—(HOOC(CH$_2$)$_{15}$CO)-γ-Glu) desB30 human insulin; N$^{εB29}$—(N$^α$—(HOOC(CH$_2$)$_{16}$CO)-γ-Glu) desB30 human insulin; N$^{εB29}$—(N$^α$—(HOOC(CH$_2$)$_{17}$CO)-γ-Glu) desB30 human insulin; N$^{εB29}$—(N$^α$—(HOOC(CH$_2$)$_{18}$CO)-γ-Glu) desB30 human insulin; N$^{εB29}$—(N$^α$—(HOOC(CH$_2$)$_{16}$CO)-γ-Glu-N-(γ-Glu)) desB30 human insulin; N$^{εB29}$—(N$^α$-(Asp-OC(CH$_2$)$_{16}$CO)-γ-Glu) desB30 human insulin; N$^{εB29}$—(N$^α$-(Glu-OC(CH$_2$)$_{14}$CO)-γ-Glu) desB30 human insulin; N$^{εB29}$—(N$^α$-(Glu-OC(CH$_2$)$_{14}$CO—) desB30 human insulin; N$^{εB29}$—(N$^α$-(Asp-OC(CH$_2$)$_{16}$CO—) desB30 human insulin; N$^{εB29}$—(N$^α$—(HOOC(CH$_2$)$_{16}$CO)-α-Glu-N-(8-Asp)) desB30 human insulin; N$^{εB29}$—(N$^α$-(Gly-OC(CH$_2$)$_{13}$CO)-γ-Glu) desB30 human insulin; N$^{εB29}$—(N$^α$-(Sar-OC(CH$_2$)$_{13}$CO)-γ-Glu) desB30 human insulin; N$^{εB29}$—(N$^α$—(HOOC(CH$_2$)$_{13}$CO)-γ-Glu) desB30 human insulin; (N$^{εB29}$—(N$^α$—(HOOC(CH$_2$)$_{13}$CO)$_{43}$-Asp) desB30 human insulin; N$^{εB29}$—(N$^α$—(HOOC(CH$_2$)$_{13}$CO)-α-Glu) desB30 human insulin; N$^{εB29}$—(N$^α$—(HOOC(CH$_2$)$_{16}$CO)-β-D-Glu) desB30 human insulin; N$^{εB29}$—(N$^α$—(HOOC(CH$_2$)$_{14}$CO)-β-D-Asp) desB30 human insulin N$^{εB29}$—(N$^α$—(HOOC(CH$_2$)$_{14}$CO)-β-D-Asp) desB30 human insulin; N$^{εB29}$(N—HOOC(CH$_2$)$_{16}$CO-β-D-Asp) desB30 human insulin; N$^{εB29}$(N—HOOC(CH$_2$)$_{14}$CO-IDA) desB30 human insulin; N$^{εB29}$—[N—(HOOC(CH$_2$)$_{16}$CO)—N-(carboxyethyl)-Gly] desB30 human insulin; N$^{εB29}$—[N—(HOOC(CH$_2$)$_{14}$CO)—N-(carboxyethyl)-Gly] desB30 human insulin; and N$^{εB29}$—[N—(HOOC(CH$_2$)$_{14}$CO)—N-(carboxymethyl)-β-Ala] desB30 human insulin.

In one aspect the side chain may comprise at least one aromatic group or at least one difunctionel PEG group. Hereinafter, the abbreviation "PEG" is used for polyethyleneglycol.

In one aspect of the invention the acylated insulin used in the pharmaceutical composition is having a formula

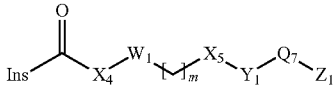

wherein Ins is the parent insulin moiety which via the α-amino group of the N-terminal amino acid residue of the B chain or an ε-amino group of a Lys residue present in the B chain of the insulin moiety is bound to the CO— group in the side chain via an amide bond;

$X_4$ is
- —$(CH_2)_n$— where n is 1, 2, 3, 4, 5 or 6;
- NR, where R is hydrogen or —$(CH_2)_p$—COOH; —$(CH_2)_p$—$SO_3H$; —$(CH_2)_p$—$PO_3H_2$, —$(CH_2)_p$—O—$SO_3H_2$; —$(CH_2)_p$—O—$PO_3H_2$; arylene substituted with 1 or 2 —$(CH_2)_p$—O—COOH groups; —$(CH_2)_p$-tetrazolyl, where p is an integer in the range of 1 to 6;
- —$(CR_1R_2)_q$—NR—CO—, where $R_1$ and $R_2$ independently of each other and independently for each value of q can be H, —COOH, or OH, q is 1-6 and R is defined as above;
- —$((CR_3R_4)_{q1}$—NR—CO$)_{2-4}$—, where $R_3$ and $R_4$ independently of each other and independently for each value of $q_1$ can be H, —COOH, or OH, $q_1$ is 1-6 and R is defined as above; or
- a bond $W_1$ is arylene or heteroarylene, which may be substituted with one or two groups selected from the group consisting of —COOH, —$SO_3H$, and —$PO_3H_2$ and tetrazolyl, or $W_1$ is a bond;

m is 0, 1, 2, 3, 4, 5 or 6;

$X_5$ is
—O—;

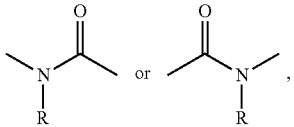

where R is defined as above; or
a bond;

$Y_1$ is
- —$(CR_1R_2)_q$—NR—CO—, where $R_1$ and $R_2$ independently of each other and independently for each value of q can be H, —COOH, a bond or OH, q is 1-6; and R is defined as above;
- NR where R is defined as above;
- —$((CR_3R_4)_{q1}$—NR—CO$)_{2-4}$—, where $R_3$ and $R_4$ independently of each other and independently for each value of $q_1$ can be H, —COOH, or OH, $q_1$ is 1-6 and R is defined as above; or
- a bond $Q_7$ is
- —$(CH_2)_r$— where r is an integer from 4 to 22;
- a divalent hydrocarbon chain comprising 1, 2 or 3 —CH=CH— groups and a number of —$CH_2$— groups sufficient to give a total number of carbon atoms in the chain in the range of 4 to 22; or
- a divalent hydrocarbon chain of the formula —$(CH_2)_s$-$Q_8$-$(C_6H_4)_{v1}$-$Q_9$-$(CH_2)_w$-$Q_{10}$-$(C_6H_4)_{v2}$-$Q_{11}$-$(CH_2)_t$-$Q_{12}$-$(C_6H_4)_{v3}$-$Q_{13}$-$(CH_2)_z$— wherein $Q_8$-$Q_{13}$ independently of each other can be O; S or a bond; where s, w, t and z independently of each other are zero or an integer from 1 to 10 so that the sum of s, w, t and z is in the range from 4 to 22, and $v_1$, $v_2$, and $v_3$ independently of each other can be zero or 1, provided that when $W_1$ is a bond then $Q_7$ is not a divalent hydrocarbon chain of the formula —$(CH_2)_{v4}C_6H_4(CH_2)_{W1}$— wherein $v_4$ and $w_1$ are integers or one of them is zero so that the sum of $v_4$ and $w_1$ is in the range of 6 to 22; and $Z_1$ is:
- —COOH;
- —CO-Asp;
- —CO-Glu;
- —CO-Gly;
- —CO-Sar;
- —CH(COOH)$_2$;
- —N(CH$_2$COOH)$_2$;
- —$SO_3H$
- —$PO_3H_2$;
- —O—$SO_3H$;
- —O—$PO_3H_2$;
- -tetrazolyl or
- —O—$W_2$, where $W_2$ is arylene or heteroarylene substituted with one or two groups selected from —COOH, —$SO_3H$, and —$PO_3H_2$ and tetrazolyl;

provided that if $W_1$ is a bond and $v_1$, $v_2$ and $v_3$ are all zero and $Q_{1-6}$ are all a bond, then $Z_1$ is O—$W_2$ and any $Zn^{2+}$ complex thereof.

In one aspect of the invention $W_1$ is phenylene. In one aspect $W_1$ is 5-7 membered heterocyclic ring system comprising nitrogen, oxygen or sulphur. In one aspect $W_1$ is a 5 membered heterocyclic ring system comprising at least one oxygen.

In one aspect of the invention $Q_7$ is —$(CH_2)_r$— where r is an integer in the range of from 4 to 22, from 8- to 20, from 12 to 20 or from 14-18. In one aspect $Q_8$, $Q_9$, $Q_{12}$ and $Q_{13}$ are all bonds, $v_2$ is 1 and $v_1$ and $v_3$ are zero. In one aspect $Q_{10}$ and $Q_{11}$ are oxygen.

In one aspect of the invention $X_4$ and $Y_1$ are a bonds and $X_5$ is

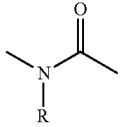

where R is —$(CH_2)_p$—COOH, where p is 1-4.

In one aspect $Z_1$ is —COOH.

In one aspect of the invention the acylated insulin of the pharmaceutical composition is selected from the group consisting of $N^{\varepsilon B29}$—[N—(HOOC(CH$_2$)$_{14}$CO)—N-(carboxyethyl)-CH$_2$—C$_6$H$_4$CO] desB30 human insulin; $N^{\varepsilon B29}$—[N—(HOOC(CH$_2$)$_{13}$CO)—N-(carboxyethyl)-CH$_2$—C$_6$H$_4$CO] desB30 human insulin; $N^{\varepsilon B29}$—[N—(HOOC(CH$_2$)$_{15}$CO)—N-(carboxyethyl)-CH$_2$—C$_6$H$_4$CO] desB30 human insulin; $N^{\varepsilon B29}$—[N—(HOOC(CH$_2$)$_{16}$CO)—N-(carboxyethyl)-CH$_2$—C$_6$H$_4$CO] desB30 human insulin; $N^{\varepsilon B29}$—[N—

(HOOC(CH$_2$)$_{14}$CO)—N-(carboxymethyl)-C$_6$H$_4$CO] desB30 human insulin, and N$^{\varepsilon B29}$—[N—(HOOC(CH$_2$)$_{14}$CO)—N-(carboxyethyl)-CH$_2$— (furanylene)CO] desB30 human insulin, N$^{\varepsilon B29}$-{4-Carboxy-4-[10-(4-carboxy-phenoxy)-decanoylamino]-butyryl}desB30 human insulin In one aspect of the invention the acylated insulin present in the pharmaceutical composition is having a formula

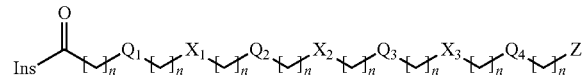

wherein Ins is the parent insulin moiety which via the α-amino group of the N-terminal amino acid residue of the B chain or an ε-amino group of a Lys residue present in the B chain of the insulin moiety is bound to the CO— group in the side chain via an amide bond;
each n is independently 0, 1, 2, 3, 4, 5 or 6;
$Q_1$, $Q_2$, $Q_3$, and $Q_4$ independently of each other can be (CH$_2$CH$_2$O)$_s$—; (CH$_2$CH$_2$CH$_2$O)$_s$—; (CH$_2$CH$_2$CH$_2$CH$_2$O)$_s$—; (CH$_2$CH$_2$OCH$_2$CH$_2$CH$_2$O)$_s$— or (CH$_2$CH$_2$CH$_2$OCH$_2$CH$_2$CH$_2$CH$_2$O)$_s$— where s is 1-20
—(CH$_2$)$_r$— where r is an integer from 4 to 22; or a divalent hydrocarbon chain comprising 1, 2 or 3 —CH=CH— groups and a number of —CH$_2$— groups sufficient to give a total number of carbon atoms in the chain in the range of 4 to 22;
—(CH$_2$)$_t$— or (CH$_2$OCH$_2$)$_t$—, where t is an integer from 1 to 6;
—(CR$_1$R$_2$)$_q$—, where R$_1$ and R$_2$ independently of each other can be H, —COOH, (CH$_2$)$_{1-6}$COOH and R$_1$ and R$_2$ can be different at each carbon, and q is 1-6,
—((CR$_3$R$_4$)$_{q1}$)$_1$—(NHCO—(CR$_3$R$_4$)$_{q1}$—NHCO)$_{1-2}$—((CR$_3$R$_4$)$_{q1}$)$_1$ or —((CR$_3$R$_4$)$_{q1}$)$_1$—(CONH—(CR$_3$R$_4$)$_{q1}$—CONH)$_{1-2}$—((CR$_3$R$_4$)$_{q1}$—)—,
—((CR$_3$R$_4$)$_{q1}$)$_1$—(NHCO—(CR$_3$R$_4$)$_{q1}$—CONH)$_{1-2}$—((CR$_3$R$_4$)$_{q1}$)$_1$ or —((CR$_3$R$_4$)$_{q1}$)$_1$—(CONH—(CR$_3$R$_4$)$_{q1}$—NHCO)$_{1-2}$—((CR$_3$R$_4$)$_{q1}$)$_1$ where R$_3$ and R$_4$ independently of each other can be H, —COOH, and R$_3$ and R$_4$ can be different at each carbon, and q$_1$ is 1-6, or
a bond;
with the proviso that Q$_1$-Q$_4$ are different;
X$_1$, X$_2$ and X$_3$ are independently
O;
a bond; or

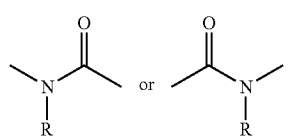

where R is hydrogen or —(CH$_2$)$_p$—COOH, —(CH$_2$)$_p$—SO$_3$H, —(CH$_2$)$_p$PO$_3$H$_2$, —(CH$_2$)$_p$—O—SO$_3$H; —(CH$_2$)$_p$—O—PO$_3$H$_2$; or (CH$_2$)$_p$-tetrazol-5-yl, where each p independently of the other p's is an integer in the range of 1 to 6; and
Z is:
—COOH;
—CO-Asp;
—CO-Glu;
—CO-Gly;
—CO-Sar;
—CH(COOH)$_2$,
—N(CH$_2$COOH)$_2$;
—SO$_3$H
—OSO$_3$H
—OPO$_3$H$_2$
—PO$_3$H$_2$ or
-tetrazol-5-yl
and any Zn$^{2+}$ complex thereof.

In one aspect of the invention s is in the range of 2-12, 2-4 or 2-3. In one aspect s is preferably 1.

In one aspect of the invention Z is —COOH.

In one aspect of the invention the acylated insulin of the pharmaceutical composition is selected from the group consisting of N$^{\varepsilon B29}$-(3-[2-{2-(2-[ω-carboxy-pentadecanoyl-γ-glutamyl-(2-amino-ethoxy)]-ethoxy)-ethoxy}-ethoxyl]-propinoyl) desB30 human insulin, N$^{\varepsilon B29}$-(3-{2-[2-(2-[ω-carboxy-heptadecanoyl-γ-glutamyl-(2-amino-ethoxy)]-ethoxy)-ethoxy]-propinoyl) desB30 human insulin, N$^{\varepsilon B29}$-{3-[2-(2-{2-(ω-carboxy-pentadecanoylamino) ethoxy]-ethoxy}-ethoxy}-ethoxyl)propionyl-γ-glutamyl desB30 human insulin, N$^{\varepsilon B29}$-(ω-[2-(2-{2-[2-(2-carboxy-ethoxy)-ethoxy]-ethoxy}-ethoxy)-ethylcarbamoyl]-heptadecanoyl-α-glutamyl) desB30 human insulin, N$^{\varepsilon B29}$-(ω-[2-(2-{2-[2-(2-carboxy-ethoxy)-ethoxy]-ethoxy}-ethoxy) ethylcarbamoyl]-heptadecanoyl-γ-glutamyl) desB30 human insulin, N$^{\varepsilon B29}$-3-[2-(2-{2-[2-(ω-carboxy-heptadecanoylamino)-ethoxy]-ethoxy}-ethoxy)-ethoxy]-propionyl-γ-glutamyl desB30 human insulin, N$^{\varepsilon B29}$-(3-(3-{2-[2-(3-[7-carboxyheptanoylamino]propoxy)ethoxy]-ethoxy}propylcarbamoyl)propionyl) desB30 human insulin, N$^{\varepsilon B29}$-(3-(3-{4-[3-(7-Carboxyheptanoylamino)propoxy]butoxy}propylcarbamoyl)-propionyl-γ-glutamyl) desB30 human insulin, N$^{\varepsilon B29}$-(3-(3-{2-[2-(3-[9-Carboxynonanoylamino]propoxy)ethoxy]-ethoxy}-propylcarbamoyl)propionyl) desB30 human insulin, N$^{\varepsilon B29}$-(3-(2-{2-[2-(9-carboxynonanoylamino)ethoxy]-ethoxy}ethylcarbamoyl) propionyl-γ-glutamyl) desB30 human insulin, N$^{\varepsilon B29}$-(3-(3-{4-[3-(9-Carboxynonanoylamino)propoxy]butoxy}-propylcarbamoyl)propionyl-γ-glutamyl) desB30 human insulin, N$^{\varepsilon B29}$-(2-[3-(2-(2-{2-(7-carboxyheptanoylamino) ethoxy}ethoxy)-ethylcarbamoyl]propionyl-γ-glutamyl) desB30 human insulin, N$^{\varepsilon B29}$-(3-[2-(2-{2-[2-(ω-carboxy-pentadecanoylamino)ethoxy]-ethoxy}ethoxy)ethoxy]-propionyl)) desB30 human insulin, N$^{\varepsilon B29}$-(3-(2-{2-[2-(2-{2-[2-(ω-carboxy-tridecanoylamino)- ethoxy]-ethoxy}-ethoxy]-ethoxy}-ethoxy)-ethoxy]-ethoxy}-ethoxy)-ethoxy]-ethoxy}-ethoxy)-propionoyl-γ-glutamyl) desB30 human insulin, N$^{\varepsilon B29}$-(3-[2-(2-{2-[2-(ω-Carboxy-tridecanoylamino)-ethoxy]-ethoxy}-ethoxy)-ethoxy]-propionoyl-γ-glutamyl) desB30 human insulin, N$^{\varepsilon B29}$-(3-[2-(2-{2-[2-(2-{2-[2-(ω-carboxy-tridecanoylamino)-ethoxy]-ethoxy}-ethoxy)-ethoxy]-ethoxy}-ethoxy)-ethoxy]-ethoxy}-propionoyl-γ-glutamyl) desB30 human insulin, N$^{\varepsilon B29}$-(3-(2-{2-[2-(ω-Carboxy-pentadecanoylamino)-ethoxy]-ethoxy}-ethylcarbamoyl)propionyl-γ-glutamyl) desB30 human insulin, N$^{\varepsilon B29}$-(3-(3-{2-[2-(3-[ω-Carboxypentadecanoylamino]propoxy)ethoxy]-ethoxy}propylcarbamoyl)propionyl-γ-glutamyl) desB30 human insulin, N$^{\varepsilon B29}$-(3-(3-{4-[3-(ω-Carboxyundecanoylamino)propoxy]butoxypropyl-carbamoyl)propionyl-γ-glutamyl) desB30 human insulin, N$^{\varepsilon B29}$-(3-(3-{4-[3-(ω-carboxytridecanoylamino)propoxy]butoxypropylcarbamoyl)propionyl-γ-glutamyl) desB30 human insulin, N$^{\varepsilon B29}$-(3-(2-{2-[2-(ω-Carboxyundecanoylamino)ethoxy]-ethoxy}ethylcarbamoyl)propionyl-γ-glutamyl) desB30 human insulin, N$^{\varepsilon B29}$-(3-(2-{2-[2-(ω-carboxytridecanoylamino)ethoxy]-ethoxy}ethylcarbamoyl)propionyl-γ-glutamyl) desB30 human insulin, $N^{\epsilon B29}$-{3-[2-(2-{2-[2-(ω-carboxy-pentadecanoylamino)ethoxy]-ethoxy}ethoxy)ethoxy] propionyl-gamma-γ-D-glutamyl) desB30 human insulin, $N^{\epsilon B29}$-{3-[2-(2-{2-[2-(7-carboxyheptanoylamino)ethoxy]-ethoxy}ethoxy)ethoxy]propionyl-γ-glutamyl} desB30 human insulin, $N^{\epsilon B29}$-{3-[2-(2-{2-[2-(9-carboxynonanoylamino)ethoxy]-ethoxy}ethoxy)ethoxy]propioniyl-γ-glutamyl} desB30 human insulin, $N^{\epsilon B29}$-{3-[2-(2-{2-[2-(ω-carboxyundecanoylamino)ethoxy]-ethoxy}ethoxy)ethoxy]-propionyl-γ-glutamyl} desB30 human insulin, $N^{\epsilon B29}$-{3-[2-(2-{2-[2-(ω-carboxytridecanoylamino)ethoxy]ethoxy}ethoxy)ethoxy]propionyl-γ-glutamyl} desB30 human insulin.

The parent insulin molecule is human insulin or an analogue thereof. Non limiting analogues of human insulin is desB30 analogue; insulin analogues where the amino acid residue in position B30 is Lys and the amino acid residue in position B29 is any codable amino acid except Cys, Met, Arg and Lys; insulin analogues where the amino acid residue at position A21 is Asn and insulin analogues where the amino acid residue at position B3 is Lys and the amino acid residue at position B29 is Glu.

In another group of parent insulin analogues, the amino acid residue at position B28 is Asp. A specific example from this group of parent insulin analogues is AspB28 human insulin disclosed in EP 214826.

In another group of parent insulin analogues, the amino acid residue at position B28 is Lys and the amino acid residue at position B29 is Pro. A specific example from this group of parent insulin analogues is $Lys^{B28}Pro^{B29}$ human insulin.

In another group of parent insulin analogues the amino acid residue in position B30 is Lys and the amino acid residue in position B29 is any codable amino acid except Cys, Met, Arg and Lys. An example is an insulin analogue where the amino acid residue at position B29 is Thr and the amino acid residue at position B30 is Lys. A specific example from this group of parent insulin analogues is $Thr^{B29}Lys^{B30}$ human insulin.

In another group of parent insulin analogues, the amino acid residue at position B3 is Lys and the amino acid residue at position B29 is Glu. A specific example from this group of parent insulin analogues is $Lys^{B3}Glu^{B29}$ human insulin.

The pharmaceutical composition according to the present invention will comprise a therapeutically effective amount of the acylated insulin together with a pharmaceutically acceptable carrier for the treatment of type 1 diabetes, type 2 diabetes and other states that cause hyperglycaemia in patients in need of such a treatment.

In a further aspect of the invention, there is provided a pharmaceutical composition for treating type 1 diabetes, type 2 diabetes and other states that cause hyperglycaemia in a patient in need of such a treatment, comprising a therapeutically effective amount of an acylated insulin derivative as defined above in mixture with an insulin or an insulin analogue which has a rapid onset of action, together with pharmaceutically acceptable carriers and additives.

Thus the pharmaceutical composition may comprise a mixture of two insulin components: one with a protracted insulin action, a basal insulin, and the other with a rapid onset of action, a bolus insulin. An example of such mixture is Insulin aspart, AspB28 human insulin in mixture with $N^{\epsilon B29}$—($N^{\alpha}$—(HOOC(CH$_2$)$_{14}$CO)-γ-Glu) desB30 human insulin corresponding to LysB29Nε-hexadecandioyl-γ-Glu desB30 human insulin disclosed in WO 2005/012347. Another example of such a mixture is Lispro, $Lys^{B28}Pro^{B29}$ human insulin, in mixture with LysB29Nε-hexadecandioyl-γ-Glu desB30 human insulin. A third example of such a mixture is Glulisine, $Lys^{B3}Glu^{B29}$-human insulin, in mixture with LysB29Nε-hexadecandioyl-γ-Glu desB30 human insulin.

In one aspect of the invention at least 85% of the rapid acting insulin is present as rapid acting insulin hexamer or complexes with a smaller molecular weight than rapid acting insulin hexamers.

In one aspect of the invention at least 90, 92, 95, 96, 97, 98, 99, 99.5% of the rapid acting insulin is present as rapid acting insulin hexamer or complexes with a smaller molecular weight than rapid acting insulin hexamers.

The acylated insulin derivative and the rapid acting insulin analogue can be mixed in a molar ratio about 90%/10%; about 75%125%, about 70%/30% about 50%/50%, about 25%/75%, about 30%170% or about 10%190%.

In one aspect the pharmaceutical composition according to the invention will have a pH between about 6.5 to about 8.5. In another aspect the pH is from about 7.0 to about 8.2, the pH is from about 7.2 to 8.0 or or from about 7.4 to about 8.0 or the pH is from about 7.4 to about 7.8.

The invention further comprises a method for producing a pharmaceutical composition comprising an acylated insulin wherein more than about 4 zinc atoms per 6 molecules of acylated insulin are added to the composition.

In a further aspect of the invention more than about 4.3 zinc atoms per 6 molecules of acylated insulin are added to the composition or more than about 4.5 zinc atoms per 6 molecules of acylated insulin are added to the composition or than about 5 zinc atoms per 6 molecules of acylated insulin are added to the composition. In a further aspect more than about 5.5 zinc atoms or more than about 6.5 zinc atoms, or more than about 7.0 zinc atoms or more than about 7.5 zinc atoms per 6 molecules of acylated insulin are added to the composition.

In one aspect of the invention the method comprises adding up to about 12 zinc atoms per 6 molecules of acylated insulin to the composition.

In one aspect of the invention the method comprises adding between about 4.3 and about 12 zinc atoms per 6 molecules of acylated insulin to the composition In a further aspect of the invention between about 4.5 and about 12 zinc atoms per 6 molecules of acylated insulin are added to the composition or about 5 and about 11.4 zinc atoms per 6 molecules of acylated insulin are added to the composition or between about 5.5 and about 10 zinc atoms per 6 molecules of acylated insulin are added to the composition.

In a further aspect between about 6 and about 10.5 zinc atoms per 6 molecules of acylated insulin or between about 6.5 and about 10 zinc atoms per 6 molecules of acylated insulin or between about 7 and about 9 zinc atoms per 6 molecules of acylated insulin are added to the composition.

In one aspect of the invention the method comprises adding zinc to the composition before the addition of a preservative. In a further aspect of the invention the number of zinc atoms added before addition of a preservative is more than 1 zinc atom per 6 molecules of acylated insulin, or the number of zinc atoms added before addition of a preservative is more than 2 zinc atom per 6 molecules of acylated insulin or the number of zinc atoms added before addition of a preservative is more than 3 zinc atom per 6 molecules of acylated insulin or the number of zinc atoms added before addition of a preservative is more than 4 zinc atom per 6 molecules of acylated insulin or the number of zinc atoms added before addition of a preservative is more than 5 zinc atom per 6 molecules of acylated insulin.

In a further aspect of the invention between about 4.5 and about 12 zinc atoms per 6 molecules of acylated insulin are added to the composition before the addition of a preservative or about 5 and about 11.4 zinc atoms per 6 molecules of acylated insulin are added to the composition before the addition of a preservative or even more preferred between about 5.5 and about 10 zinc atoms per 6 molecules of acylated insulin are added to the composition before the addition of a preservative. In a further aspect between about 6 and about 10.5 zinc atoms per 6 molecules of acylated insulin or between about 6.5 and about 10 zinc atoms per 6 molecules of acylated insulin or between about 7 and about 9 zinc atoms per 6 molecules of acylated insulin are added to the composition before the addition of a preservative.

In one aspect of the invention the method comprises adding zinc to the composition after addition of a preservative. In one aspect of the invention at least 0.5 zinc atom per 6 molecules of acylated insulin is added to the composition after addition of a preservative or at least 1 zinc atom per 6 molecules of acylated insulin is added to the composition after addition of a preservative.

In a further aspect of the invention more than about 2 zinc atoms per 6 molecules of acylated insulin are added to the composition after the addition of a preservative or more than about 3 zinc atoms per 6 molecules of acylated insulin are added to the composition after the addition of a preservative or more than about 4 zinc atoms per 6 molecules of acylated insulin are added to the composition after the addition of a preservative.

In a further aspect of the invention between about 0.5 and about 12, between about 1 and about 11.4, between about 1.5 and about 11, between about 2 and about 10.5, between about 3 and about 10 or between about 4 and about 9 zinc atoms per 6 molecules of acylated insulin are added to the composition after the addition of a preservative.

In a further aspect of the invention between about 4.5 and about 12 zinc atoms per 6 molecules of acylated insulin are added to the composition after the addition of a preservative or about 5 and about 11.4 zinc atoms per 6 molecules of acylated insulin are added to the composition after the addition of a preservative or between about 5.5 and about 10 zinc atoms per 6 molecules of acylated insulin are added to the composition after the addition of a preservative.

In a further aspect between about 6 and about 10.5 zinc atoms per 6 molecules of acylated insulin or between about 6.5 and about 10 zinc atoms per 6 molecules of acylated insulin or between about 7 and about 9 zinc atoms per 6 molecules of acylated insulin are added to the composition after the addition of a preservative.

In one aspect of the invention the method comprises adding part of the zinc before addition of a preservative and adding part of the zinc after addition of a preservative.

In one aspect the method comprises adding at least 0.5 zinc atom per 6 molecules of acylated insulin before addition of a preservative and adding at least 1 zinc atom per 6 molecules of acylated insulin after addition of a preservative. In one aspect the method comprises at least 0.5 zinc atom per 6 molecules of acylated insulin before addition of a preservative and adding at least 2, 3, 4, 5, 6, 7, 8, 9, 10 or 11 zinc atoms per 6 molecules of acylated insulin after addition of a preservative.

In one aspect the method comprises adding at least 1 zinc atom per 6 molecules of acylated insulin before addition of a preservative and adding at least 1 zinc atom per 6 molecules of acylated insulin after addition of a preservative or adding at least 1 zinc atom per 6 molecules of acylated insulin before addition of a preservative and adding at least 2 or 3 zinc atoms per 6 molecules of acylated insulin after addition of a preservative or adding at least 1 zinc atom per 6 molecules of acylated insulin before addition of a preservative and up to about 11 zinc atom per 6 molecules of acylated insulin after addition of a preservative. In one aspect the method comprises adding at least 1 zinc atom per 6 molecules of acylated insulin before addition of a preservative and adding at least 4, 5, 6, 7, 8, 9, 10 or 11 zinc atoms per 6 molecules of acylated insulin after addition of a preservative.

In one aspect the method comprises adding at least 2 zinc atoms per 6 molecules of acylated insulin before addition of a preservative and adding at least 1 zinc atom per 6 molecules of acylated insulin after addition of a preservative or adding at least 2 zinc atoms per 6 molecules of acylated insulin before addition of a preservative and adding at least 2 or 3 zinc atoms per 6 molecules of acylated insulin after addition of a preservative or adding at least 2 zinc atoms per 6 molecules of acylated insulin before addition of a preservative and up to about 10 zinc atoms per 6 molecules of acylated insulin after addition of a preservative In one aspect the method comprises adding at least 2 zinc atom per 6 molecules of acylated insulin before addition of a preservative and adding at least 4, 5, 6, 7, 8, 9 or 10 zinc atoms per 6 molecules of acylated insulin after addition of a preservative.

In one aspect the method comprises adding at least 3 zinc atoms per 6 molecules of acylated insulin before addition of a preservative and adding at least 1 zinc atom per 6 molecules of acylated insulin after addition of a preservative or adding at least 3 zinc atoms per 6 molecules of acylated insulin before addition of a preservative and adding at least 2 or 3 zinc atoms per 6 molecules of acylated insulin after addition of a preservative or adding at least 3 zinc atoms per 6 molecules of acylated insulin before addition of a preservative and up to about 9 zinc atoms per 6 molecules of acylated insulin after addition of a preservative In one aspect of the invention the number of zinc atoms added before addition of a preservative is at least 3 zinc atom per 6 molecules of acylated insulin and the number of zinc atoms added after addition of a preservative are at least 3 zinc atoms per 6 molecules of acylated insulin. In one aspect the method comprises adding at least 3 zinc atom per 6 molecules of acylated insulin before addition of a preservative and adding at least 4, 5, 6, 7, 8 or 9 zinc atoms per 6 molecules of acylated insulin after addition of a preservative.

In one aspect of the invention the preservative added is phenol and/or m-cresol.

In one aspect of the invention the method comprises adding the whole amount of zinc atoms to the pharmaceutical composition in one step.

In one aspect of the invention the method comprises adding the zinc atoms to the pharmaceutical composition in two or more steps. For example, zinc may be added to the composition in one, two, three, four or five steps, where each step includes addition of small amounts of max. 1 Zn/6ins. The zinc may be added to the composition in one, two, three, four or five steps, where each step includes addition of small amounts of 2 Zn/6ins, 3 Zn/6ins, 4 Zn/6ins, 5 Zn/6ins or 6 Zn/6ins.

In one aspect of the invention, the method comprises adding a surfactant to the pharmaceutical compostion. The surfactant can be mixed in the pharmaceutical composition in an amount of 0.0005-0.01% based on the weight of the pharmaceutical composition. In one aspect the surfactant can be mixed in the pharmaceutical composition in an amount of 0.0005-0.007% based on the weight of the composition. An example of a surfactant could be polysorbate 20, which can be mixed in the pharmaceutical composition in an amount of 0.001-0.003% based on the weight of the composition. Another example is poloxamer 188, which can be mixed in the pharmaceutical composition in an amount of 0.002-0.006% based on the weight of the composition.

In a further aspect of the invention the method comprises an acylated insulin which insulin has a side chain attached to the ε-amino group of a Lys residue present in the B chain of the parent insulin, the side chain being of the general formula:

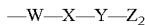

wherein W is:
  an α-amino acid residue having a carboxylic acid group in the side chain which residue forms, with one of its carboxylic acid groups, an amide group together with ε-amino group of a Lys residue present in the B chain of the parent insulin;
  a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
  a covalent bond from X to an ε-amino group of a Lys residue present in the B chain of the parent insulin;
X is:
  —$\underline{C}$O—;
  —CH(COOH)$\underline{C}$O—;
  —CO—N(CH$_2$COOH)CH$_2$$\underline{C}$O—;
  —CO—N(CH$_2$COOH)CH$_2$CON(CH$_2$COOH)CH$_2$$\underline{C}$O—;
  —CO—N(CH$_2$CH$_2$COOH)CH$_2$CH$_2$$\underline{C}$O—;
  —CO—N(CH$_2$CH$_2$COOH)CH$_2$CH$_2$CON(CH$_2$CH$_2$COOH)CH$_2$CH$_2$$\underline{C}$O—;
  —CO—NHCH(COOH)(CH$_2$)$_4$NH$\underline{C}$O—;
  —CO—N(CH$_2$CH$_2$COOH)CH$_2$$\underline{C}$O—; or
  —CO—N(CH$_2$COOH)CH$_2$CH$_2$$\underline{C}$O—.
that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an ε-amino group of a Lys residue present in the B chain of the parent insulin;
Y is:
  —(CH$_2$)$_m$— where m is an integer in the range of 6 to 32;
  a divalent hydrocarbon chain comprising 1, 2 or 3 —CH=CH— groups and a number of —CH$_2$— groups sufficient to give a total number of carbon atoms in the chain in the range of 10 to 32; and
Z$_2$ is:
  —COOH;
  —CO-Asp;
  —CO-Glu;
  —CO-Gly;
  —CO-Sar;
  —CH(COOH)$_2$;
  —N(CH$_2$COOH)$_2$;
  —SO$_3$H; or
  —PO$_3$H
and any Zn$^{2+}$ complexes thereof, provided that when W is a covalent bond and X is —CO—, then Z is different from —COOH.

In one aspect of the invention the acylated insulin is selected from the group consisting of N$^{εB29}$—(N$^α$—(HOOC(CH$_2$)$_{14}$CO)-γ-Glu) desB30 human insulin; N$^{εB29}$—(N$^α$—(HOOC(CH$_2$)$_{15}$CO)-γ-Glu) desB30 human insulin; N$^{εB29}$—(N$^α$—(HOOC(CH$_2$)$_{16}$CO)-γ-Glu) desB30 human insulin; —N$^{εB29}$—(N$^α$—(HOOC(CH$_2$)$_{17}$CO)-γ-Glu) desB30 human insulin; N$^{εB29}$—(N$^α$—(HOOC(CH$_2$)$_{18}$CO)-γ-Glu) desB30 human insulin; N$^{εB29}$—(N$^α$—(HOOC(CH$_2$)$_{16}$CO)-γ-Glu-N-(γ-Glu)) desB30 human insulin; N$^{εB29}$—(N$^α$-(Asp-OC(CH$_2$)$_{16}$CO)-γ-Glu) desB30 human insulin; N$^{εB29}$—(N$^α$-(Glu-OC(CH$_2$)$_{14}$CO)-γ-Glu) desB30 human insulin; N$^{εB29}$—(N$^α$-(Glu-OC(CH$_2$)$_{14}$CO—) desB30 human insulin; N$^{εB29}$—(N$^α$-(Asp-OC(CH$_2$)$_{16}$CO—) desB30 human insulin; N$^{εB29}$—(N$^α$—(HOOC(CH$_2$)$_{16}$CO)-α-Glu-N-(β-Asp)) desB30 human insulin; N$^{εB29}$—(N$^α$-(Gly-OC(CH$_2$)$_{13}$CO)-γ-Glu) desB30 human insulin; N$^{εB29}$—(N$^α$-(Sar-OC(CH$_2$)$_{13}$CO)-γ-Glu) desB30 human insulin; N$^{εB29}$—(N$^α$—(HOOC(CH$_2$)$_{13}$CO)-γ-Glu) desB30 human insulin; (N$^{εB29}$—(N$^α$—(HOOC(CH$_2$)$_{13}$CO)-β-Asp) desB30 human insulin; N$^{εB29}$—(N$^α$—(HOOC(CH$_2$)$_{13}$CO)-α-Glu) desB30 human insulin; N$^{εB29}$—(N$^α$—(HOOC(CH$_2$)$_{16}$CO)-γ-D-Glu) desB30 human insulin; N$^{εB29}$—(N$^α$—(HOOC(CH$_2$)$_{14}$CO)$_{43}$-D-Asp) desB30 human insulin N$^{εB29}$—(N$^α$—(HOOC(CH$_2$)$_{14}$CO)-β-D-Asp) desB30 human insulin; —N$^{εB29}$(N—HOOC(CH$_2$)$_{16}$CO(3-D-Asp) desB30 human insulin; N$^{εB29}$(N—HOOC(CH$_2$)$_{14}$CO-IDA) desB30 human insulin; N$^{εB29}$—[N—(HOOC(CH$_2$)$_{16}$CO)—N-(carboxyethyl)-Gly] desB30 human insulin; N$^{εB29}$—[N—(HOOC(CH$_2$)$_{14}$CO)—N-(carboxyethyl)-Gly] desB30 human insulin; and N$^{εB29}$—[N—(HOOC(CH$_2$)$_{14}$CO)—N-(carboxymethyl)-β-Ala] desB30 human insulin.

In one aspect of the invention the acylated insulin used in the method for preparing a pharmaceutical composition is having a formula

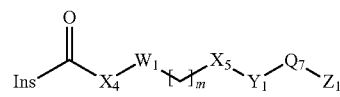

wherein Ins is the parent insulin moiety which via the α-amino group of the N-terminal amino acid residue of the B chain or an ε-amino group of a Lys residue present in the B chain of the insulin moiety is bound to the CO— group in the side chain via an amide bond;
X$_4$ is
  —(CH$_2$)$_n$ where n is 1, 2, 3, 4, 5 or 6;
  NR, where R is hydrogen or —(CH$_2$)$_p$—COOH; —(CH$_2$)$_p$—SO$_3$H; —(CH$_2$)$_p$—PO$_3$H$_2$, —(CH$_2$)$_p$—O—SO$_3$H$_2$; —(CH$_2$)$_p$—O—PO$_3$H$_2$; arylene substituted with 1 or 2 —(CH$_2$)$_p$—O—COOH groups; —(CH$_2$)$_p$— tetrazolyl, where p is an integer in the range of 1 to 6;
  —(CR$_1$R$_2$)$_q$—NR—CO—, where R$_1$ and R$_2$ independently of each other and independently for each value of q can be H, —COOH, or OH, q is 1-6 and R is defined as above;

—$((CR_3R_4)_{q1}$—NR—$CO)_{2-4}$—, where $R_3$ and $R_4$ independently of each other and independently for each value of $q_1$ can be H, —COOH, or OH, $q_1$ is 1-6 and R is defined as above; or a bond $W_1$ is arylene or heteroarylene, which may be substituted with one or two groups selected from the group consisting of —COOH, —$SO_3H$, and —$PO_3H_2$ and tetrazolyl, or $W_1$ is a bond;

m is 0, 1, 2, 3, 4, 5 or 6;

$X_5$ is

—O—;

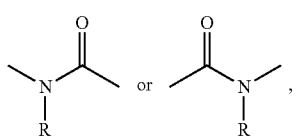

where R is defined as above; or a bond;

$Y_1$ is

—$(CR_1R_2)_q$—NR—CO—, where $R_1$ and $R_2$ independently of each other and independently for each value of q can be H, —COOH, a bond or OH, q is 1-6; and R is defined as above;

NR where R is defined as above;

—$((CR_3R_4)_{q1}$—NR—$CO)_{2-4}$—, where $R_3$ and $R_4$ independently of each other and independently for each value of $q_1$ can be H, —COOH, or OH, $q_1$ is 1-6 and R is defined as above; or a bond;

$Q_7$ is

—$(CH_2)_r$— where r is an integer from 4 to 22;

a divalent hydrocarbon chain comprising 1, 2 or 3 —CH=CH— groups and a number of —$CH_2$— groups sufficient to give a total number of carbon atoms in the chain in the range of 4 to 22; or a divalent hydrocarbon chain of the formula

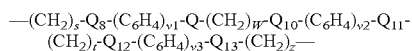

wherein $Q_8$-$Q_{13}$ independently of each other can be O; S or a bond; where s, w, t and z independently of each other are zero or an integer from 1 to 10 so that the sum of s, w, t and z is in the range from 4 to 22, and $v_1$, $v_2$, and $v_3$ independently of each other can be zero or 1, provided that when $W_1$ is a bond then $Q_7$ is not a divalent hydrocarbon chain of the formula —$(CH_2)_{v4}C_6H_4(CH_2)_{w1}$ wherein $v_4$ and $w_1$ are integers or one of them is zero so that the sum of $v_4$ and $w_1$ is in the range of 6 to 22; and $Z_1$ is:
—COOH;
—CO-Asp;
—CO-Glu;
—CO-Gly;
—CO-Sar;
—$CH(COOH)_2$;
—$N(CH_2COOH)_2$;
—$SO_3H$
—$PO_3H_2$;
—O—$SO_3H$;
—O—$PO_3H_2$;
-tetrazolyl or
—O—$W_2$, where $W_2$ is arylene or heteroarylene substituted with one or two groups selected from —COOH, —$SO_3H$, and —$PO_3H_2$ and tetrazolyl;

provided that if $W_1$ is a bond and $v_1$, $v_2$ and $v_3$ are all zero and $Q_{8-13}$ are all a bonds, then $Z_1$ is O—$W_2$ and any $Zn^{2+}$ complex thereof.

In one aspect of the invention $W_1$ is phenylene. In one aspect $W_1$ is 5-7 membered heterocyclic ring system comprising nitrogen, oxygen or sulphur. In one aspect $W_1$ is a 5 membered heterocyclic ring system comprising at least one oxygen.

In one aspect of the invention $Q_7$ is —$(CH_2)_r$— where r is an integer in the range of from 4 to 22, from 8- to 20, from 12 to 20 or from 14-18. In one aspect $Q_8$, $Q_9$, $Q_{12}$ and $Q_{13}$ are all bonds, $v_2$ is 1 and $v_1$ and $v_3$ are zero. In one aspect $Q_{10}$ and $Q_{11}$ are oxygen.

In one aspect of the invention $X_4$ and $Y_1$ are a bonds and $X_5$ is

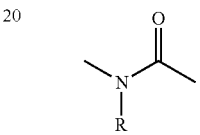

where R is —$(CH_2)_p$—COOH, where p is 1-4.

In one aspect $Z_1$ is —COOH.

In one aspect of the invention the acylated insulin of the method is selected from the group consisting of $N^{\varepsilon B29}$—[N—(HOOC$(CH_2)_{14}$CO)—N-(carboxyethyl)-$CH_2$—$C_6H_4$CO] desB30 human insulin; —$N^{\varepsilon B29}$—[N—(HOOC$(CH_2)_{13}$CO)—N-(carboxyethyl)-$CH_2$—$C_6H_4$CO] desB30 human insulin; $N^{\varepsilon B29}$—[N—(HOOC$(CH_2)_{15}$CO)—N-(carboxyethyl)-$CH_2$—$C_6H_4$CO] desB30 human insulin; $N^{\varepsilon B29}$—[N—(HOOC$(CH_2)_{16}$CO)—N-(carboxyethyl)-$CH_2$—$C_6H_4$CO] desB30 human insulin; $N^{\varepsilon B29}$-[N—(HOOC$(CH_2)_{14}$CO)—N-(carboxymethyl)-$C_6H_4$CO] desB30 human insulin, and $N^{\varepsilon B29}$—[N—(HOOC$(CH_2)_{14}$CO)—N-(carboxyethyl)-$CH_2$— (furanylene)CO] desB30 human insulin, $N^{\varepsilon B29}$-{4-Carboxy-4-[10-(4-carboxy-phenoxy)-decanoylamino]-butyryl}desB30 human insulin In one aspect of the invention the acylated insulin used in the method is having a formula

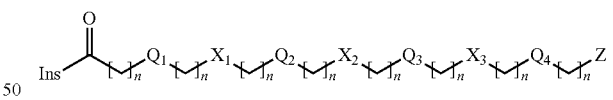

wherein Ins is the parent insulin moiety which via the α-amino group of the N-terminal amino acid residue of the B chain or an ε-amino group of a Lys residue present in the B chain of the insulin moiety is bound to the CO— group in the side chain via an amide bond;

each n is independently 0, 1, 2, 3, 4, 5 or 6;

$Q_1$, $Q_2$, $Q_3$, and $Q_4$ independently of each other can be $(CH_2CH_2O)_s$—; $(CH_2CH_2CH_2O)_s$—; $(CH_2CH_2CH_2CH_2O)_s$—; $(CH_2CH_2OCH_2CH_2CH_2CH_2O)_s$— or $(CH_2CH_2CH_2OCH_2CH_2CH_2CH_2O)_s$— where s is 1-20

—$(CH_2)_r$— where r is an integer from 4 to 22; or a divalent hydrocarbon chain comprising 1, 2 or 3 —CH=CH— groups and a number of —$CH_2$— groups sufficient to give a total number of carbon atoms in the chain in the range of 4 to 22;

—(CH$_2$)$_t$— or —(CH$_2$OCH$_2$)$_t$—, where t is an integer from 1 to 6;
—(CR$_1$R$_2$)$_q$—, where R$_1$ and R$_2$ independently of each other can be H, —COOH,
—(CH$_2$)$_{1-6}$COOH and R$_1$ and R$_2$ can be different at each carbon, and q is 1-6,
—((CR$_3$R$_4$)$_{q1}$)$_1$—(NHCO—(CR$_3$R$_4$)$_{q1}$—NHCO)$_{1-2}$—((CR$_3$R$_4$)$_{q1}$)$_1$ or —((CR$_3$R$_4$)$_{q1}$)$_1$—(CONH—(CR$_3$R$_4$)$_{q1}$—CONH)$_{1-2}$—((CR$_3$R$_4$)$_{q1}$—)—,
—((CR$_3$R$_4$)$_{q1}$)$_1$—(NHCO—(CR$_3$R$_4$)$_{q1}$—CONH)$_{1-2}$—((CR$_3$R$_4$)$_{q1}$)$_1$ or —((CR$_3$R$_4$)$_{q1}$)$_1$—(CONH—(CR$_3$R$_4$)$_{q1}$—NHCO)$_{1-2}$—((CR$_3$R$_4$)$_{q1}$)$_1$ where R$_3$ and R$_4$ independently of each other can be H, —COOH, and R$_3$ and R$_4$ can be different at each carbon, and q$_1$ is 1-6, or a bond;
with the proviso that Q$_1$-Q$_4$ are different;
X$_1$, X$_2$ and X$_3$ are independently
O;
a bond; or

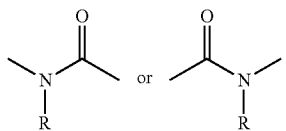

where R is hydrogen or —(CH$_2$)$_p$—COOH, —(CH$_2$)$_p$—SO$_3$H, —(CH$_2$)$_p$PO$_3$H$_2$, —(CH$_2$)$_p$—O—SO$_3$H; —(CH$_2$)$_p$—O—PO$_3$H$_2$; or —(CH$_2$)$_p$-tetrazol-5-yl, where each p independently of the other p's is an integer in the range of 1 to 6; and
Z is:
—COOH;
—CO-Asp;
—CO-Glu;
—CO-Gly;
—CO-Sar;
—CH(COOH)$_2$,
—N(CH$_2$COOH)$_2$;
—SO$_3$H
—OSO$_3$H
—OPO$_3$H$_2$
—PO$_3$H$_2$ or
-tetrazol-5-yl
and any Zn$^{2+}$ complex thereof.

In one aspect of the invention s is in the range of 2-12, 2-4 or 2-3. In one aspect s is preferably 1.

In one aspect of the invention Z is —COOH.

In one aspect of the invention the acylated insulin used in the method for preparing a pharmaceutical composition is selected from the group consisting of N$^{\varepsilon B29}$-(3-[2-{2-(2-[ω-carboxy-pentadecanoyl-γ-glutamyl-(2-amino-ethoxy)]-ethoxy)-ethoxy}-ethoxy]-propinoyl) desB30 human insulin, N$^{\varepsilon B29}$-(3-[2-{2-(2-[ω-carboxy-heptadecanoyl-γ-glutamyl-(2-aminoethoxy)]-ethoxy)-ethoxy}-ethoxy]-propinoyl) desB30 human insulin, N$^{\varepsilon B29}$-{3-[2-(2-{2-[2-(ω-carboxy-pentadecanoylamino)-ethoxy]-ethoxy}-ethoxy)-ethoxy]-propionyl-γ-glutamyl desB30 human insulin, N$^{\varepsilon B29}$-(ω-[2-(2-{2-[2-(2-carboxy-ethoxy)-ethoxy]-ethoxy}-ethoxy)ethylcarbamoyl]-heptadecanoyl-α-glutamyl) desB30 human insulin, N$^{\varepsilon B29}$-(ω-[2-(2-{2-[2-(2-carboxy-ethoxy)-ethoxy]-ethoxy}-ethoxy)-ethylcarbamoyl]-heptadecanoyl-γ-glutamyl) desB30 human insulin, N$^{\varepsilon B29}$-3-[2-(2-{2-[2-(ω-carboxy-heptadecanoylamino)-ethoxy]-ethoxy}-ethoxy)-ethoxy]-propionyl-γ-glutamyl desB30 human insulin, N$^{\varepsilon B29}$-(3-(3-{2-[2-(3-[7-carboxyheptanoylamino]propoxy) ethoxy]-ethoxy}propylcarbamoyl)propionyl) desB30 human insulin, N$^{\varepsilon B29}$-(3-(3-{4-[3-(7-Carboxyheptanoylamino)propoxy]butoxy}propylcarbamoyl)propionyl-γ-glutamyl) desB30 human insulin, N$^{\varepsilon B29}$-(3-(3-{2-[2-(3-[9-Carboxynonanoylamino]propoxy)ethoxy]-ethoxy}-propylcarbamoyl)propionyl) desB30 human insulin, N$^{\varepsilon B29}$-(3-(2-{2-[2-(9-carboxynonanoylamino)ethoxy]-ethoxy}ethylcarbamoyl) propionyl-γ-glutamyl) desB30 human insulin, N$^{\varepsilon B29}$-(3-(3-{4-[3-(9-Carboxynonanoylamino)propoxy]butoxy}-propylcarbamoyl)propionyl-γ-glutamyl) desB30 human insulin, N$^{\varepsilon B29}$-(2-[3-(2-(2-{2-(7-carboxyheptanoylamino)ethoxy}ethoxy)ethylcarbamoyl] propionyl-γ-glutamyl) desB30 human insulin, N$^{\varepsilon B29}$-(3-[2-(2-{2-[2-(ω-carboxypentadecanoylamino)ethoxy] ethoxy}ethoxy)ethoxy]propionyl)) desB30 human insulin, N$^{\varepsilon B29}$-(3-(2-{2-[2-(2-{2-[2-(2-{2-[2-(2-{2-[2-(ω-carboxytridecanoylamino)-ethoxy]-ethoxy}-ethoxy)-ethoxy]-ethoxy}-ethoxy)-ethoxy]-ethoxy}-ethoxy)-ethoxy]-ethoxy}-ethoxy)-propionoyl-γ-glutamyl) desB30 human insulin, N$^{\varepsilon B29}$-(3-[2-(2-{2-[2-(ω-Carboxy-tridecanoylamino)-ethoxy]-ethoxy}-ethoxy)-ethoxy]-propionoyl-γ-glutamyl) desB30 human insulin, N$^{\varepsilon B29}$-(3-[2-(2-{2-[2-(2-{2-[2-(ω-carboxy-tridecanoylamino)-ethoxy]-ethoxy}-ethoxy)-ethoxy]-ethoxy}-ethoxy)-ethoxy]-ethoxy}-ethoxy)-propionoyl-γ-glutamyl) desB30 human insulin, N$^{\varepsilon B29}$-(3-(2-{2-[2-(ω-Carboxy-pentadecanoylamino)-ethoxy]-ethoxy}-ethylcarbamoyl)-propionyl-γ-glutamyl) desB30 human insulin, N$^{\varepsilon B29}$-(3-(3-{2-[2-(3-(ω-Carboxypentadecanoylamino]propoxy)ethoxy]-ethoxy}propylcarbamoyl)propionyl-γ-glutamyl) desB30 human insulin, N$^{\varepsilon B29}$-(3-(3-{4-[3-(ω-Carboxyundecanoylamino)propoxy]butoxypropylcarbamoyl)propionyl-γ-glutamyl) desB30 human insulin, N$^{\varepsilon B29}$-(3-(3-{4-[3-(ω-carboxytridecanoylamino)propoxy]butoxypropyl-carbamoyl)propionyl-γ-glutamyl) desB30 human insulin, N$^{\varepsilon B29}$-(3-(2-{2-[2-(ω-Carboxyundecanoylamino)ethoxy]ethoxy}ethylcarbamoyl) propionyl-γ-glutamyl) desB30 human insulin, N$^{\varepsilon B29}$-(3-(2-{2-[2-(ω-carboxytridecanoylamino)ethoxy]-ethoxy}ethylcarbamoyl)propionyl-γ-glutamyl) desB30 human insulin, N$^{\varepsilon B29}$-{3-[2-(2-{2-[2-(ω-carboxy-pentadecanoylamino)ethoxy]ethoxy}ethoxy)ethoxy]propionyl-gamma-γ-D-glutamyl) desB30 human insulin, N$^{\varepsilon B29}$-{3-[2-(2-{2-[2-(7-carboxyheptanoylamino)ethoxy]-ethoxy}ethoxy)ethoxy]-propionyl-γ-glutamyl} desB30 human insulin, N$^{\varepsilon B29}$-{3-[2-(2-{2-[2-(9-carboxynonanoylamino)ethoxy]-ethoxy}ethoxy)ethoxy]propioniyl-γ-glutamyl} desB30 human insulin, N$^{\varepsilon B29}$-{3-[2-(2-{2-[2-(9-carboxyundecanoylamino)ethoxy]-ethoxy}ethoxy)ethoxy]-propionyl-γ-glutamyl} desB30 human insulin, N$^{\varepsilon B29}$-{3-[2-(2-{2-[2-(ω-carboxytridecanoylamino)ethoxy]ethoxy}ethoxy)ethoxy]propionyl-γ-glutamyl} desB30 human insulin.

In one aspect of the invention the method comprises adding a rapid acting insulin to the composition. The rapid acting insulin is AspB28human insulin, LysB28ProB29 human insulin and Lys$^{B3}$Glu$^{B29}$-human insulin or a mixture thereof.

In one aspect of the invention the pharmaceutical composition comprising acylated insulin is used for treatment of diabetes.

In one aspect of the invention, the pharmaceutical composition comprising acylated insulin is used for the manufacture of a medicament for the treatment of diabetes.

In one aspect the invention is related to a pharmaceutical composition according to the invention together with a pharmaceutically acceptable carrier and/or a pharmaceutically acceptable additive, which composition can be provided for the treatment of type 1 diabetes, type 2 diabetes and other states that cause hyperglycaemia in patients in need of such a treatment.

In one aspect of the invention, there is provided a method of treating type 1 diabetes, type 2 diabetes and other states that cause hyperglycaemia in a patient in need of such a treatment, comprising administering to the patient a therapeutically effective amount of an pharmaceutical composition together with a pharmaceutically acceptable carrier and/or pharmaceutical acceptable additives.

In one aspect of the invention, there is provided a method for the manufacture of a pharmaceutical composition for the use in the treatment of type 1 diabetes, type 2 diabetes and other states that cause hyperglycaemia.

In one aspect of the invention, there is provided a pharmaceutical composition for treating type 1 diabetes, type 2 diabetes and other states that cause hyperglycaemia in a patient in need of such a treatment.

In one aspect of the invention, there is provided a method of treating type 1 diabetes, type 2 diabetes and other states that cause hyperglycaemia in a patient in need of such a treatment, comprising administering to the patient a therapeutically effective amount of an pharmaceutical composition according to the invention.

In one aspect of the invention, there is provided a method for the manufacture of a pharmaceutical composition for the use in the treatment of type 1 diabetes, type 2 diabetes and other states that cause hyperglycaemia.

The pharmaceutical composition comprising an acylated insulin as defined in the present specification may be administered simultaneously or sequentially with OAD(s) or GLP-1. The factors may be supplied in single-dosage form wherein the single-dosage form contains both compounds, or in the form of a kit-of-parts comprising a preparation of a the pharmaceutical composition comprising a pharmaceutical composition comprising an acylated insulin and a pharmaceutical composition containing an OAD as a second unit dosage form. Whenever a first or second or third, etc., unit dose is mentioned throughout this specification this does not indicate the preferred order of administration, but is merely done for convenience purposes.

By "simultaneous" dosing of a preparation of a pharmaceutical composition comprising an acylated insulin and a preparation of OAD(s) or GLP-1 is meant administration of the compounds in single-dosage form, or administration of a first agent followed by administration of a second agent with a time separation of no more than 15 minutes, 10, 5 or 2 minutes. Either factor may be administered first.

By "sequential" dosing is meant administration of a first agent followed by administration of a second agent with a time separation of more than 15 minutes. Either of the two unit dosage form may be administered first. Preferably, both products are injected through the same intravenous access.

In a further aspect of the invention the pharmaceutical composition comprising an accylated insulin is administered once daily simultaneously or sequentially with OAD(s) or GLP-1. In a more preferred aspect the pharmaceutical composition comprising an acylated insulin further comprises a rapid acting insulin and is administered once daily together with OAD(s) or GLP-1. In one aspect of the invention the pharmaceutical composition comprising an acylated insulin can be a stand alone intensive treatment given up till 5 times daily. In an even more preferred aspect the pharmaceutical composition further comprises a rapid acting insulin, where the intensive treatment can be a stand alone treatment given up till 5 times daily.

The invention will be summarized in the following paragraphs:

1. A soluble pharmaceutical composition comprising an acylated insulin and further comprising more than 4 zinc atoms per 6 molecules of acylated insulin.
2. Pharmaceutical composition according to paragraph 1 comprising up to about 12 zinc atoms per 6 molecules of acylated insulin.
3. Pharmaceutical composition according to paragraphs 1 or 2 comprising between about 4.3 and about 12 zinc atoms per 6 molecules of acylated insulin.
4. Pharmaceutical composition according to any of paragraphs 1-3 comprising between about 4.5 and about 12 zinc atoms per 6 molecules of acylated insulin.
5. Pharmaceutical composition according to any of the preceding paragraphs, wherein at least 85% of the acylated insulin is present as complexes which are acylated insulin dodecamers or complexes with a higher molecular weight than acylated insulin dodecamer.
6. Pharmaceutical composition according to any of the preceding paragraphs, wherein at least 92% of the acylated insulin is present as complexes which are acylated insulin dodecamers or complexes with a higher molecular weight than acylated insulin dodecamer.
7. Pharmaceutical composition according to any of the preceding paragraphs, wherein at least 95% of the acylated insulin is present as complexes which are acylated insulin dodecamers or complexes with a higher molecular weight than acylated insulin dodecamer.
8. Pharmaceutical composition according to any of the preceding paragraphs, wherein at least 97% of the acylated insulin is present as complexes which are acylated insulin dodecamers or complexes with a higher molecular weight than acylated insulin dodecamer.
9. Pharmaceutical composition according to any of the preceding paragraphs, wherein the composition comprises a surfactant.
10. Pharmaceutical composition according to any of the preceding paragraphs, wherein the acylated insulin is an insulin acylated in the ε-amino group of a Lys residue in a position in the B-chain of the parent insulin molecule.
11. Pharmaceutical composition according to any of paragraphs 1-10, wherein the acyl group comprises at least one free carboxylic acid or a group which is negatively charged at neutral pH.
12. Pharmaceutical composition according to paragraph 1 or 10-11, wherein the acyl group is derived from a dicarboxylic fatty acid with from 4 to 32 carbon atoms.
13. Pharmaceutical composition according to paragraph 1 or 10-12, wherein the acyl group is attached to the insulin molecule via a linker group through amide bonds.
14. Pharmaceutical composition according to paragraph 1 or 13, wherein the linker group comprises at least one free carboxylic group or a group which is negatively charged at neutral pH.
15. Pharmaceutical composition according to any of paragraphs 1-14, wherein the insulin molecule has a side chain attached either to the α-amino group of the N-terminal amino acid residue of the B chain or to an ε-amino group of a Lys residue present in the B chain of the parent insulin moiety via an amide bond, which side chain comprises at least one free carboxylic acid group or a group which is negatively charged at neutral pH, a fatty acid moiety with about 4 to about 32 carbon atoms in the carbon chain; and possible one or more linkers linking the individual components in the side chain together via amide bonds.

16. Pharmaceutical composition according to paragraphs 1-15, wherein the side chain comprises at least one aromatic group.

17. Pharmaceutical composition according to paragraphs 1-15, wherein the side chain comprises at least one difunctionel PEG group.

18. Pharmaceutical composition according to any of paragraphs 1-15, wherein the insulin molecule has a side chain attached to the ε-amino group of a Lys residue present in the B chain of the parent insulin, the side chain being of the general formula:

—W—X—Y—$Z_2$ wherein W is:
an α-amino acid residue having a carboxylic acid group in the side chain which residue forms, with one of its carboxylic acid groups, an amide group together with ε-amino group of a Lys residue present in the B chain of the parent insulin;
a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or a covalent bond from X to an ε-amino group of a Lys residue present in the B chain of the parent insulin;

X is:
—CO—;
—CH(COOH)C̲O—;
—CO—N(CH$_2$COOH)CH$_2$C̲O—;
—CO—N(CH$_2$COOH)CH$_2$CON(CH$_2$COOH)CH$_2$C̲O—;
—CO—N(CH$_2$CH$_2$COOH)CH$_2$CH$_2$C̲O—;
—CO—N(CH$_2$CH$_2$COOH)CH$_2$CH$_2$CON(CH$_2$CH$_2$COOH)CH$_2$CH$_2$C̲O;
—CO—NHCH(COOH)(CH$_2$)$_4$NHC̲O—;
—CO—N(CH$_2$CH$_2$COOH)CH$_2$C̲O—; or
—CO—N(CH$_2$COOH)CH$_2$CH$_2$C̲O—.

that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an ε-amino group of a Lys residue present in the B chain of the parent insulin;

Y is:
—(CH$_2$)$_m$— where m is an integer in the range of 6 to 32;
a divalent hydrocarbon chain comprising 1, 2 or 3 —CH═CH— groups and a number of —CH$_2$— groups sufficient to give a total number of carbon atoms in the chain in the range of 10 to 32; and $Z_2$ is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H and any Zn$^{2+}$ complexes thereof, provided that when W is a covalent bond and X is —CO—, then Z is different from —COOH.

19. Pharmaceutical composition according to any of paragraphs 1-15 and 18, wherein $Z_2$ is COOH.

20. Pharmaceutical composition according to paragraphs 1-15 and 18-19 wherein the acylated insulin is selected from the group consisting of N$^{εB29}$—(N$^α$—(HOOC(CH$_2$)$_{14}$CO)-γ-Glu) desB30 human insulin; N$^{εB29}$—(N$^α$—(HOOC(CH$_2$)$_{15}$CO)-γ-Glu) desB30 human insulin; N$^{εB29}$—(N$^α$—(HOOC(CH$_2$)$_{16}$CO)-γ-Glu) desB30 human insulin; N$^{εB29}$—(N$^α$—(HOOC(CH$_2$)$_{17}$CO)-γ-Glu) desB30 human insulin; N$^{εB29}$—(N$^α$—(HOOC(CH$_2$)$_{18}$CO)-γ-Glu) desB30 human insulin; N$^{εB29}$—(N$^α$—(HOOC(CH$_2$)$_{16}$CO)-γ-Glu-N-(γ-Glu)) desB30 human insulin; N$^{εB29}$—(N$^α$-(Asp-OC(CH$_2$)$_{16}$CO)-γ-Glu) desB30 human insulin; N$^{εB29}$—(N$^α$-(Glu-OC(CH$_2$)$_{14}$CO)-γ-Glu) desB30 human insulin; N$^{εB29}$—(N$^α$-(Glu-OC(CH$_2$)$_{14}$CO—) desB30 human insulin; N$^{εB29}$—(N$^α$-(Asp-OC(CH$_2$)$_{16}$CO—) desB30 human insulin; N$^{εB29}$—(N$^α$—(HOOC(CH$_2$)$_{16}$CO)-α-Glu-N-(8-Asp)) desB30 human insulin; N$^{εB29}$—(N$^α$-(Gly-OC(CH$_2$)$_{13}$CO)-γ-Glu) desB30 human insulin; N$^{εB29}$—(N$^α$-(Sar-OC(CH$_2$)$_{13}$CO)-γ-Glu) desB30 human insulin; N$^{εB29}$—(N$^α$—(HOOC(CH$_2$)$_{13}$CO)-γ-Glu) desB30 human insulin; (N$^{εB29}$—(N$^α$—(HOOC(CH$_2$)$_{13}$CO)$_{13}$-Asp) desB30 human insulin; N$^{εB29}$—(N$^α$—(HOOC(CH$_2$)$_{13}$CO)-α-Glu) desB30 human insulin; N$^{εB29}$—(N$^α$—(HOOC(CH$_2$)$_{16}$CO)-γ-D-Glu) desB30 human insulin; N$^{εB29}$—(N$^α$—(HOOC(CH$_2$)$_{14}$CO)-β-D-Asp) desB30 human insulin N$^{εB29}$—(N$^α$—(HOOC(CH$_2$)$_{14}$CO)-β-D-Asp) desB30 human insulin; N$^{εB29}$(N—HOOC(CH$_2$)$_{16}$CO-β-D-Asp) desB30 human insulin; N$^{εB29}$—(N—HOOC(CH$_2$)$_{14}$CO-IDA) desB30 human insulin; N$^{εB29}$—[N(HOOC(CH$_2$)$_{16}$CO)—N-(carboxyethyl)-Gly] desB30 human insulin; N$^{εB29}$—[N—(HOOC(CH$_2$)$_{14}$CO)—N-(carboxyethyl)-Gly] desB30 human insulin; and N$^{εB29}$—[N—(HOOC(CH$_2$)$_{14}$CO)—N-(carboxymethyl)-β-Ala] desB30 human insulin.

21. Pharmaceutical composition according to paragraph 1-16, wherein the acylated insulin is having a formula

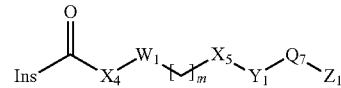

wherein Ins is the parent insulin moiety which via the α-amino group of the N-terminal amino acid residue of the B chain or an ε-amino group of a Lys residue present in the B chain of the insulin moiety is bound to the CO— group in the side chain via an amide bond;

$X_4$ is
—(CH$_2$)$_n$ where n is 1, 2, 3, 4, 5 or 6;
NR, where R is hydrogen or —(CH$_2$)$_p$—COOH; —(CH$_2$)$_p$—SO$_3$H; —(CH$_2$)$_p$—PO$_3$H$_2$; —(CH$_2$)$_p$—O—SO$_3$H$_2$; —(CH$_2$)$_p$—O—PO$_3$H$_2$; arylene substituted with 1 or 2 —(CH$_2$)$_p$—O—COOH groups; —(CH$_2$)$_p$— tetrazolyl, where p is an integer in the range of 1 to 6;

—(CR$_1$R$_2$)$_q$—NR—CO—, where R$_1$ and R$_2$ independently of each other and independently for each value of q can be H, —COOH, or OH, q is 1-6 and R is defined as above;

—((CR$_3$R$_4$)$_{q1}$—NR—CO)$_{2-4}$—, where R$_3$ and R$_4$ independently of each other and independently for each value of q$_1$ can be H, —COOH, or OH, q$_1$ is 1-6 and R is defined as above; or
a bond
W$_1$ is arylene or heteroarylene, which may be substituted with one or two groups selected from the group consisting of —COOH, —SO$_3$H, and —PO$_3$H$_2$ and tetrazolyl, or W$_1$ is a bond;
m is 0, 1, 2, 3, 4, 5 or 6;
X$_5$ is
—O—;

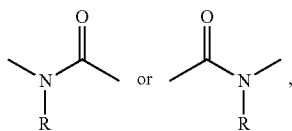

where R is defined as above; or
a bond;
Y$_1$ is
—(CR$_1$R$_2$)$_q$—NR—CO—, where R$_1$ and R$_2$ independently of each other and independently for each value of q can be H, —COOH, a bond or OH, q is 1-6; and R is defined as above;
NR where R is defined as above;
—((CR$_3$R$_4$)$_{q1}$—NR—CO)$_{2-4}$—, where R$_3$ and R$_4$ independently of each other and independently for each value of q$_1$ can be H, —COOH, or OH, q$_1$ is 1-6 and R is defined as above; or
a bond;
Q$_7$ is
—(CH$_2$)$_r$— where r is an integer from 4 to 22;
a divalent hydrocarbon chain comprising 1, 2 or 3 —CH=CH— groups and a number of —CH$_2$— groups sufficient to give a total number of carbon atoms in the chain in the range of 4 to 22; or
a divalent hydrocarbon chain of the formula

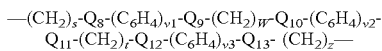

wherein Q$_8$-Q$_{13}$ independently of each other can be O; S or a bond; where s, w, t and z independently of each other are zero or an integer from 1 to 10 so that the sum of s, w, t and z is in the range of 4 to 22, and v$_1$, v$_2$, and v$_3$ independently of each other can be zero or 1, provided that when W$_1$ is a bond then Q$_7$ is not a divalent hydrocarbon chain of the formula (CH$_2$)$_{v4}$C$_6$H$_4$(CH$_2$)$_{w1}$ wherein v$_4$ and w$_1$ are integers or one of them is zero so that the sum of v$_4$ and w$_1$ is in the range of 6 to 22; and
Z$_1$ is:
—COOH;
—CO-Asp;
—CO-Glu;
—CO-Gly;
—CO-Sar;
—CH(COOH)$_2$;
—N(CH$_2$COOH)$_2$;
—SO$_3$H
—PO$_3$H$_2$;
—O—SO$_3$H;
—O—PO$_3$H$_2$;
-tetrazolyl or
—O—W$_2$, where W$_2$ is arylene or heteroarylene substituted with one or two groups selected from —COOH, —SO$_3$H, and —PO$_3$H$_2$ and tetrazolyl;
provided that if W$_1$ is a bond and v$_1$, v$_2$ and v$_3$ are all zero and Q$_{8-13}$ are all a bonds, then Z$_1$ is O—W$_2$
and any Zn$^{2+}$ complex thereof.
22. Pharmaceutical composition according to paragraph) or 21, wherein W$_1$ is phenylene.
23. Pharmaceutical composition according to paragraph 1 or 21, wherein W$_1$ is 5-7 membered heterocyclic ring system comprising nitrogen, oxygen or sulphur.
24. Pharmaceutical composition according to paragraph 1, 21 and 23, wherein W$_1$ is a 5 membered heterocyclic ring system comprising at least one oxygen.
25. Pharmaceutical composition according paragraphs 21-24, wherein Q$_7$ is —(CH$_2$)$_r$— where r is an integer in the range of from 4 to 22, from 8- to 20, from 12 to 20 or from 14-18.
26. Pharmaceutical composition according paragraph 21-24, wherein Q$_8$, Q$_9$, Q$_{12}$ and Q$_{13}$ are all bonds, v$_2$ is 1 and v$_1$ and v$_3$ are zero.
27. Pharmaceutical composition according paragraph 26, wherein Q$_{10}$ and Q$_{11}$ are oxygen.
28. Pharmaceutical composition according paragraphs 21-27, wherein X$_4$ and Y$_1$ are a bonds and X$_5$ is

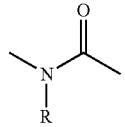

where R is —(CH$_2$)$_p$—COOH, where p is 1-4.
29. Pharmaceutical composition to paragraphs 21-28, wherein Z$_1$ is —COOH.
30. Pharmaceutical composition to paragraph 1-15 and 17, wherein the acylated insulin is having a formula

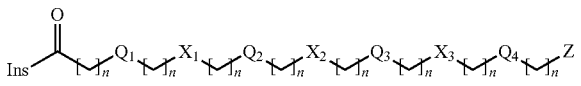

wherein Ins is the parent insulin moiety which via the α-amino group of the N-terminal amino acid residue of the B chain or an ε-amino group of a Lys residue present in the B chain of the insulin moiety is bound to the CO— group in the side chain via an amide bond;
each n is independently 0, 1, 2, 3, 4, 5 or 6;
Q$_1$, Q$_2$, Q$_3$, and Q$_4$ independently of each other can be (CH$_2$CH$_2$O)$_s$—; (CH$_2$CH$_2$CH$_2$O)$_s$—; (CH$_2$CH$_2$CH$_2$CH$_2$O)$_s$—; (CH$_2$CH$_2$OCH$_2$CH$_2$CH$_2$CH$_2$O)$_s$— or (CH$_2$CH$_2$CH$_2$OCH$_2$CH$_2$CH$_2$CH$_2$O)$_s$— where s is 1-20
—(CH$_2$)$_r$— where r is an integer from 4 to 22; or a divalent hydrocarbon chain comprising 1, 2 or 3 —CH=CH— groups and a number of —CH$_2$— groups sufficient to give a total number of carbon atoms in the chain in the range of 4 to 22;
—(CH$_2$)$_t$— or —(CH$_2$OCH$_2$)$_t$—, where t is an integer from 1 to 6;
—(CR$_1$R$_2$)$_q$—, where R$_1$ and R$_2$ independently of each other can be H, —COOH, (CH$_2$)$_{1-6}$COOH and R$_1$ and R$_2$ can be different at each carbon, and q is 1-6, —((CR$_3$R$_4$)$_{q1}$)$_1$—(NHCO—(CR$_3$R$_4$)$_{q1}$—NHCO)$_{1-2}$—((CR$_3$R$_4$)$_{q1}$)$_1$ or —((CR$_3$R$_4$)$_{q1}$)$_1$—(CONH—(CR$_3$R$_4$)$_{q1}$—CONH)$_{1-2}$ —((CR$_3$R$_4$)$_{q1}$—)—, —((CR$_3$R$_4$)$_{q1}$)$_1$—(NHCO—(CR$_3$R$_4$)$_{q1}$—CONH)$_{1-2}$—((CR$_3$R$_4$)$_{q1}$)$_1$ or —((CR$_3$R$_4$)$_{q1}$)$_1$—(CONH—(CR$_3$R$_4$)$_{q1}$—NHCO)$_{1-2}$—((CR$_3$R$_4$)$_{q1}$)$_1$ where R$_3$ and R$_4$ independently of each other can be H, —COOH, and R$_3$ and R$_4$ can be different at each carbon, and q$_1$ is 1-6-, or a bond;

with the proviso that Q$_1$-Q$_4$ are different;

X$_1$, X$_2$ and X$_3$ are independently

O;

a bond; or where R is hydrogen or —(CH$_2$)$_p$—COOH, —(CH$_2$)$_p$—SO$_3$H, —(CH$_2$)$_p$—PO$_3$H$_2$, —(CH$_2$)$_p$—O—SO$_3$H; —(CH$_2$)$_p$—O—PO$_3$H$_2$; or —(CH$_2$)$_p$— tetrazol-5-yl, where each p independently of the other p's is an integer in the range of 1 to 6; and Z is:
—COOH;
—CO-Asp;
—CO-Glu;
—CO-Gly;
—CO-Sar;
—CH(COOH)$_2$,
—N(CH$_2$COOH)$_2$;
—SO$_3$H
—OSO$_3$H
—OPO3H$_2$
—PO$_3$H$_2$ or
-tetrazol-5-yl and any Zn$^{2+}$ complex thereof.

31. Pharmaceutical composition according to paragraphs 1 or 30, wherein s is in the range of 2-12, 2-4 or 2-3

32. Pharmaceutical composition according to paragraphs 1 or 30, wherein s is preferably 1.

33. Pharmaceutical composition according to paragraph 30-32, wherein Z is —COOH.

34. Pharmaceutical composition according to any of the preceeding paragraphs, wherein the parent insulin is a desB30 human insulin analogue.

35. Pharmaceutical composition according to any of the preceding paragraphs, wherein the parent insulin is selected from the group consisting of human insulin; desB1 human insulin; desB30 human insulin; GlyA21 human insulin; GlyA21 desB30 human insulin; AspB28 human insulin; porcine insulin; LysB28 ProB29 human insulin; GlyA21 ArgB31 ArgB32 human insulin; and LysB3 GluB29 human insulin or AspB28 desB30 human insulin.

36. Pharmaceutical composition according to paragraphs 1-16, 21-29 and 34-35, wherein the acylated insulin is selected from the group consisting of
N$^{\varepsilon B29}$—[N—(HOOC(CH$_2$)$_{14}$CO)—N-(carboxyethyl)-CH$_2$—C$_6$H$_4$CO] desB30 human insulin; —N$^{\varepsilon B29}$—[N—(HOOC(CH$_2$)$_{13}$CO)—N-(carboxyethyl)-CH$_2$—C$_6$H$_4$CO] desB30 human insulin; N$^{\varepsilon B29}$[N—(HOOC(CH$_2$)$_{15}$CO)—N-(carboxyethyl)-CH$_2$—C$_6$H$_4$CO] desB30 human insulin; N$^{\varepsilon B29}$—[N—(HOOC(CH$_2$)$_{16}$CO)—N-(carboxyethyl)-CH$_2$—C$_6$H$_4$CO] desB30 human insulin; N$^{\varepsilon B29}$—[N—(HOOC(CH$_2$)$_{14}$CO)—N-(carboxymethyl)-C$_6$H$_4$CO] desB30 human insulin, and N$^{\varepsilon B29}$—[N—(HOOC(CH$_2$)$_{14}$CO)—N-(carboxyethyl)-CH$_2$— (furanylene)CO] desB30 human insulin, N$^{\varepsilon B29}$-{4-Carboxy-4-[10-(4-carboxy-phenoxy)-decanoylamino]-butyryl}desB30 human insulin 37. Pharmaceutical composition according to paragraphs 1-15, 17 and 30-35, wherein the acylated insulin is selected from the group consisting of N$^{\varepsilon B29}$-(3-[2-{2-(2-[(ω-carboxy-pentadecanoyl-γ-glutamyl-(2-amino-ethoxy)]-ethoxy)-ethoxy}ethoxy]-propinoyl) desB30 human insulin, N$^{\varepsilon B29}$-(3-[2-{2-(2-[ω-carboxy-heptadecanoyl-γ-glutamyl-(2-amino-ethoxy)]-ethoxy)]-ethoxy}-ethoxy)-propinoyl) desB30 human insulin, N$^{\varepsilon B29}$-{3-[2-(2-{2-[2-(ω-carboxy-pentadecanoylamino)-ethoxy]-ethoxy}-ethoxy)-ethoxy]-propionyl-γ-glutamyl desB30 human insulin, N$^{\varepsilon B29}$-(ω-[2-(2-{2-[2-(2-carboxy-ethoxy)-ethoxy]-ethoxy}-ethoxy)-ethylcarbamoyl]-heptadecanoyl-α-glutamyl) desB30 human insulin, N$^{\varepsilon B29}$-(ω-[2-(2-{2-[2-(2-carboxy-ethoxy)-ethoxy]-ethoxy}-ethoxy)-ethylcarbamoyl-heptadecanoyl-γ-glutamyl) desB30 human insulin, N$^{\varepsilon B29}$-3-[2-(2-{2-[2-(ω-carboxy-heptadecanoylamino)-ethoxy]-ethoxy}-ethoxy) ethoxy]-propionyl-γ-glutamyl desB30 human insulin, N$^{\varepsilon B29}$-(3-(3-{2-[2-(3-[7-carboxyheptanoylamino]propoxy) ethoxy]-ethoxy}propylcarbamoyl)propionyl) desB30 human insulin, N$^{\varepsilon B29}$-(3-(3-{4-[3-(7-Carboxyheptanoylamino)propoxy]butoxy}propylcarbamoyl)-propionyl-γ-glutamyl) desB30 human insulin, N$^{\varepsilon B29}$-(3-(3-{2-[2-(3-[9-Carboxynonanoylamino]propoxy)ethoxy]-ethoxy}-propylcarbamoyl)propionyl) desB30 human insulin, N$^{\varepsilon B29}$-(3-(2-{2-[2-(9-carboxynonanoylamino)ethoxy]-ethoxy}ethylcarbamoyl) propionyl-γ-glutamyl) desB30 human insulin, N$^{\varepsilon B29}$-(3-(3-{4-[3-(9-Carboxynonanoylamino)propoxy]butoxy}-propylcarbamoyl)propionyl-γ-glutamyl) desB30 human insulin, N$^{\varepsilon B29}$-(2-[3-(2-(2-{2-(7-carboxyheptanoylamino)ethoxy}ethoxy)-ethylcarbamoyl] propionyl-γ-glutamyl) desB30 human insulin, N$^{\varepsilon B29}$-(3-[2-(2-{2-[2-(ω-carboxypentadecanoylamino)ethoxy]ethoxy}ethoxy)ethoxy]propionyl)) desB30 human insulin, N$^{\varepsilon B29}$-(3-(2-{2-[2-(2-{2-[2-(2-{2-[2-(2-{2-[2-(ω-carboxy-tridecanoylamino)-ethoxy]-ethoxy}-ethoxy)-ethoxy]-ethoxy}-ethoxy)-ethoxy]-ethoxy}-ethoxy)-ethoxy]-ethoxy}-ethoxy)-propionoyl-γ-glutamyl) desB30 human insulin, N$^{\varepsilon B29}$-(3-[2-(2-{2-[2-(ω-Carboxy-tridecanoylamino)-ethoxy]-ethoxy}-ethoxy)-ethoxy]-propionoyl-γ-glutamyl) desB30 human insulin, N$^{\varepsilon B29}$-(3-[2-(2-{2-[2-(2-{2-[2-(ω-carboxy-tridecanoylamino)-ethoxy]-ethoxy}-ethoxy)-ethoxy]-ethoxy}-ethoxy)-ethoxy]-ethoxy}-propionoyl-γ-glutamyl) desB30 human insulin, N$^{\varepsilon B29}$-(3-(2-{2-[2-(ω-Carboxy-pentadecanoylamino)-ethoxy]-ethoxy}-ethylcarbamoyl)-propionyl-γ-glutamyl) desB30 human insulin, N$^{\varepsilon B29}$-(3-(3-{2-[2-(3-[ω-Carboxypentadecanoylamino]propoxy)ethoxy]-ethoxy}propylcarbamoyl)propionyl-γ-glutamyl) desB30 human insulin, N$^{\varepsilon B29}$-(3-(3-{4-[3-(ω-Carboxyundecanoylamino)propoxy]butoxypropylcarbamoyl)propionyl-γ-glutamyl) desB30 human insulin, N$^{\varepsilon B29}$-(3-(3-{4-[3-(ω-carboxytridecanoylamino)propoxy]butoxypropylcarbamoyl)propionyl-γ-glutamyl) desB30 human insulin, N$^{\varepsilon B29}$-(3-(2-{2-[2-(ω-Carboxyundecanoylamino)ethoxy]ethoxy}ethylcarbamoyl) propionyl-γ-glutamyl) desB30 human insulin, N$^{\varepsilon B29}$-(3-(2-{2-[2-(ω-carboxytridecanoylamino)ethoxy]-ethoxy}ethylcarbamoyl)propionyl-γ-glutamyl) desB30 human insulin, N$^{\varepsilon B29}$-{3-[2-(2-{2-[2-(ω-carboxypentadecanoylamino)ethoxy]ethoxy}ethoxy)ethoxy]propionylgamma-γ-D-glutamyl} desB30 human insulin, $N^{εB29}$-{3-[2-(2-{2-[2-(7-carboxyheptanoylamino)ethoxy]-ethoxy}ethoxy)ethoxy]-propionyl-γ-glutamyl} desB30 human insulin, $N^{εB29}$-{3-[2-(2-{2-[2-(9-carboxynonanoy-lamino)ethoxy]-ethoxy}ethoxy)ethoxy]propioniyl-γ-gluta-myl} desB30 human insulin, $N^{εB29}$-{3-[2-(2-{2-[2-(ω-car-boxyundecanoylamino)ethoxy]-ethoxy}ethoxy)ethoxy]-propionyl-γ-glutamyl} desB30 human insulin, $N^{εB29}$-{3-[2-(2-{2-[2-(ωcarboxytridecanoylamino)ethoxy]ethoxy}ethoxy)ethoxy]propionyl-γ-glutamyl} desB30 human insulin.

38. Pharmaceutical composition according to any of the preceeding paragraphs, having a pH between about 6.5 and 8.5

39. Pharmaceutical composition according to any of the preceding paragraphs further comprising a rapid acting insulin 40. Pharmaceutical composition according to paragraphs 1 and 39, wherein at least 85% of the rapid acting insulin is present as rapid acting insulin hexamer or complexes with a smaller molecular weight than rapid acting insulin hexamers.

41. Pharmaceutical composition according to paragraphs 1 and 39-40, wherein at least 92% of the rapid acting insulin is present as rapid acting insulin hexamer or complexes with a smaller molecular weight than rapid acting insulin hexamers.

42. Pharmaceutical composition according to paragraphs 1 and 39-41, wherein at least 95% of the rapid acting insulin is present as rapid acting insulin hexamer or complexes with a smaller molecular weight than rapid acting insulin hexamers.

43. Pharmaceutical composition according to paragraphs 1 and 39-42, wherein at least 97% of the rapid acting insulin is present as rapid acting insulin hexamer or complexes with a smaller molecular weight than rapid acting insulin hexamers.

44. Pharmaceutical composition according to paragraphs 1 and 39-43, wherein at least 99% of the rapid acting insulin is present as rapid acting insulin hexamer or complexes with a smaller molecular weight than rapid acting insulin hexamers.

45. Pharmaceutical composition according to paragraphs 39-44, wherein the rapid acting insulin is AspB28 human insulin, LysB3 GluB29 human insulin and/or LysB28 ProB29 human insulin.

46. Method for producing a pharmaceutical composition comprising an acylated insulin wherein more than about 4 zinc atoms per 6 molecules of acylated insulin are added to the composition.

47. Method according to paragraph 46 wherein up to about 12 zinc atoms per 6 molecules of acylated insulin are added to the composition.

48. Method according to any of paragraphs 46-47 wherein between about 4.3 and about 12 zinc atoms per 6 molecules of acylated insulin are added to the composition.

49. Method according to paragraph 46-48 wherein the zinc is added to the composition before addition of a preservative.

50. Method according to any of the paragraphs 46-49 wherein the number of zinc atoms added before addition of a preservative is more than 1 zinc atom per 6 molecules of acylated insulin.

51. Method according to any of the paragraphs 46-50 wherein the number of zinc atoms added before addition of a preservative is more than 2 zinc atom per 6 molecules of acylated insulin.

52. Method according to any of the paragraphs 46-51 wherein the number of zinc atoms added before addition of a preservative is more than 3 zinc atom per 6 molecules of acylated insulin.

53. Method according to any of the paragraphs 46-52 wherein the number of zinc atoms added before addition of a preservative is more than 4 zinc atom per 6 molecules of acylated insulin.

54. Method according to any of the paragraphs 46-53 wherein the number of zinc atoms added before addition of a preservative is more than 5 zinc atom per 6 molecules of acylated insulin.

55. Method according to any of the paragraphs 46-48 wherein the zinc is added to the composition after addition of a preservative.

56. Method according to paragraph 46-48 and 55 wherein at least 0.5 zinc atom per 6 molecules of acylated insulin is added to the composition after addition of a preservative.

57. Method according to any of the paragraphs 46-48 and 55-56 wherein at least 1 zinc atom per 6 molecules of acylated insulin is added to the composition after addition of a preservative.

58. Method according to any of the preceding method paragraphs, wherein part of the zinc is added before addition of a preservative and part of the zinc is added after addition of a preservative 59. Method according to any of the preceding method paragraphs, wherein the number of zinc atoms added before addition of a preservative is at least 3 zinc atom per 6 molecules of acylated insulin and the number of zinc atoms added after addition of a preservative are at least 3 zinc atoms per 6 molecules of acylated insulin.

60. Method according to any of the preceding method paragraphs, wherein the preservative is phenol and/or m-cresol.

61. Method according to any of the preceding method paragraphs, wherein a surfactant is mixed with the pharmaceutical composition.

62. Method according to any of the preceding method paragraphs, wherein acylated insulin has a side chain attached to the ε-amino group of a Lys residue present in the B chain of the parent insulin, the side chain being of the general formula:

—W—X—Y—$Z_2$ wherein W is:
an α-amino acid residue having a carboxylic acid group in the side chain which residue forms, with one of its carboxylic acid groups, an amide group together with ε-amino group of a Lys residue present in the B chain of the parent insulin;
a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
a covalent bond from X to an ε-amino group of a Lys residue present in the B chain of the parent insulin;
X is:
—CO—;
—CH(COOH)CO—;
—CO—N(CH$_2$COOH)CH$_2$CO—;

—CO—N(CH$_2$COOH)CH$_2$CON(CH$_2$COOH)CH$_2$C̲O—;
—CO—N(CH$_2$CH$_2$COOH)CH$_2$CH$_2$C̲O—;
—CO—N(CH$_2$CH$_2$COOH)CH$_2$CH$_2$CON (CH$_2$CH$_2$COOH)CH$_2$CH$_2$C̲O—;
—CO—NHCH(COOH)(CH$_2$)$_4$NHC̲O—;
—CO—N(CH$_2$CH$_2$COOH)CH$_2$C̲O—; or
—CO—N(CH$_2$COOH)CH$_2$CH$_2$C̲O—.

that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an ε-amino group of a Lys residue present in the B chain of the parent insulin;
Y is:
—(CH$_2$)$_m$— where m is an integer in the range of 6 to 32;
a divalent hydrocarbon chain comprising 1, 2 or 3 —CH=CH— groups and a number of —CH$_2$— groups sufficient to give a total number of carbon atoms in the chain in the range of 10 to 32; and
Z$_2$ is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H
and any Zn$^{2+}$ complexes thereof, provided that when W is a covalent bond and X is —CO—, then Z is different from —COOH.
63. Method according to any of the preceding method paragraphs, wherein the acylated insulin is selected from the group consisting of N$^{εB29}$—(N$^α$—(HOOC(CH$_2$)$_{14}$CO)-γ-Glu) desB30 human insulin; N$^{εB29}$—(N$^α$—(HOOC(CH$_2$)$_{15}$CO)-γ-Glu) desB30 human insulin; N$^{εB29}$—(N$^α$—(HOOC(CH$_2$)$_{16}$CO)-γ-Glu) desB30 human insulin; N$^{εB29}$—(N$^α$—(HOOC(CH$_2$)$_{17}$CO)-γ-Glu) desB30 human insulin; N$^{εB29}$—(N$^α$—(HOOC(CH$_2$)$_{18}$CO)-γ-Glu) desB30 human insulin; N$^{εB29}$—(N$^α$—(HOOC(CH$_2$)$_{16}$CO)-γ-Glu-N-(γ-Glu)) desB30 human insulin; N$^{εB29}$—(N$^α$-(Asp-OC(CH$_2$)$_{16}$CO)-γ-Glu) desB30 human insulin; N$^{εB29}$—(N$^α$-(Glu-OC(CH$_2$)$_{14}$CO)-γ-Glu) desB30 human insulin; N$^{εB29}$—(N$^α$-(Glu-OC(CH$_2$)$_{14}$CO—) desB30 human insulin; N$^{εB29}$—(N$^α$-(Asp-OC(CH$_2$)$_{16}$CO—) desB30 human insulin; N$^{εB29}$—(N$^α$—(HOOC(CH$_2$)$_{16}$CO)-α-Glu-N-(β-Asp)) desB30 human insulin; N$^{εB29}$—(N$^α$-(Gly-OC(CH$_2$)$_{13}$CO)-γ-Glu) desB30 human insulin; N$^{εB29}$—(N$^α$-(Sar-OC(CH$_2$)$_{13}$CO)-γ-Glu) desB30 human insulin; N$^{εB29}$—(N$^α$—(HOOC(CH$_2$)$_{13}$CO)-γ-Glu) desB30 human insulin; (N$^{εB29}$—(N$^α$—(HOOC(CH$_2$)$_{13}$CO)$_{43}$-Asp) desB30 human insulin; N$^{εB29}$—(N$^α$—(HOOC(CH$_2$)$_{13}$CO)-α-Glu) desB30 human insulin; N$^{εB29}$—(N$^α$—(HOOC(CH$_2$)$_{16}$CO)-γ-D-Glu) desB30 human insulin; N$^{εB29}$—(N$^α$—(HOOC(CH$_2$)$_{14}$CO)$_{43}$-D-Asp) desB30 human insulin N$^{εB29}$—(N$^α$—(HOOC(CH$_2$)$_{14}$CO)-β-D-Asp) desB30 human insulin; N$^{εB29}$(N—HOOC(CH$_2$)$_{16}$CO$_{43}$-D-Asp) desB30 human insulin; N$^{εB29}$(N—HOOC(CH$_2$)$_{14}$CO-IDA) desB30 human insulin; N$^{εB29}$—[N—(HOOC(CH$_2$)$_{16}$CO)—N-(carboxyethyl)-Gly] desB30 human insulin; N$^{εB29}$—[N—(HOOC(CH$_2$)$_{14}$CO)—N-(carboxyethyl)-Gly] desB30 human insulin; and N$^{εB29}$—[N—(HOOC(CH$_2$)$_{14}$CO)—N-(carboxymethyl)-β-Ala] desB30 human insulin.

64. Method according to paragraphs 46-61, wherein the acylated insulin is having a formula

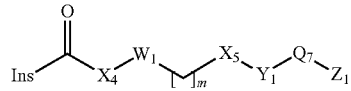

wherein Ins is the parent insulin moiety which via the α-amino group of the N-terminal amino acid residue of the B chain or an ε-amino group of a Lys residue present in the B chain of the insulin moiety is bound to the CO— group in the side chain via an amide bond;
X$_4$ is
—(CH$_2$)$_n$ where n is 1, 2, 3, 4, 5 or 6;
—NR, where R is hydrogen or —(CH$_2$)$_p$—COOH—; —(CH$_2$)$_p$—SO$_3$H; —(CH$_2$)$_p$—PO$_3$H$_2$, —(CH$_2$)$_p$—O—SO$_3$H$_2$; —(CH$_2$)$_p$—O—PO$_3$H$_2$; arylene substituted with 1 or 2 —(CH$_2$)$_p$—O—COOH groups; —(CH$_2$)$_p$— tetrazolyl, where p is an integer in the range of 1 to 6;
—(CR$_1$R$_2$)$_q$—NR—CO—, where R$_1$ and R$_4$ independently of each other and independently for each value of q can be H, —COOH, or OH, q is 1-6 and R is defined as above;
—((CR$_3$R$_4$)$_{q1}$—NR—CO)$_{2-4}$—, where R$_3$ and R$_4$ independently of each other and independently for each value of q$_1$ can be H, —COOH, or OH, q$_1$ is 1-6 and R is defined as above; or
a bond
W$_1$ is arylene or heteroarylene, which may be substituted with one or two groups selected from the group consisting of —COOH, —SO$_3$H, and —PO$_3$H$_2$ and tetrazolyl, or W$_1$ is a bond;
m is 0, 1, 2, 3, 4, 5 or 6;
X$_5$ is
—O—;

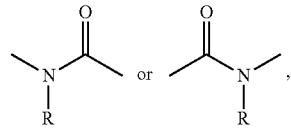

where R is defined as above; or
a bond;
Y$_1$ is
—(CR$_1$R$_2$)$_q$—NR—CO—, where R$_1$ and R$_2$ independently of each other and independently for each value of q can be H, —COOH, a bond or OH, q is 1-6; and R is defined as above;
NR where R is defined as above;
—((CR$_3$R$_4$)$_{q1}$—NR—CO)$_{2-4}$—, where R$_3$ and R$_4$ independently of each other and independently for each value of q$_1$ can be H, —COOH, or OH, q$_1$ is 1-6 and R is defined as above; or
a bond;
Q$_7$ is
—(CH$_2$)$_r$— where r is an integer from 4 to 22;
a divalent hydrocarbon chain comprising 1, 2 or 3 —CH=CH— groups and a number of —CH$_2$— groups sufficient to give a total number of carbon atoms in the chain in the range of 4 to 22; or a divalent hydrocarbon chain of the formula

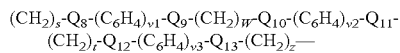

wherein $Q_8$-$Q_{13}$ independently of each other can be O; S or a bond; where s, w, t and z independently of each other are zero or an integer from 1 to 10 so that the sum of s, w, t and z is in the range from 4 to 22, and $v_1$, $v_2$, and $v_3$ independently of each other can be zero or 1, provided that when $W_1$ is a bond then $Q_7$ is not a divalent hydrocarbon chain of the formula $(CH_2)_{v4}C_6H_4(CH_2)_{W1}$— wherein $v_4$ and $w_1$ are integers or one of them is zero so that the sum of $v_4$ and $w_1$ is in the range of 6 to 22; and $Z_1$ is:
—COOH;
—CO-Asp;
—CO-Glu;
—CO-Gly;
—CO-Sar;
—CH(COOH)$_2$;
—N(CH$_2$COOH)$_2$;
—SO$_3$H
—PO$_3$H$_2$;
O—SO$_3$H;
O—PO$_3$H$_2$;
-tetrazolyl or
—O—W$_2$,
where W$_2$ is arylene or heteroarylene substituted with one or two groups selected from —COOH, —SO$_3$H, and —PO$_3$H$_2$ and tetrazolyl;
provided that if W$_1$ is a bond and $v_1$, $v_2$ and $v_3$ are all zero and $Q_8$-$Q_{13}$ are all a bonds, then $Z_1$ is O—W$_2$
and any Zn$^{2+}$ complex thereof.

65. Method according to paragraphs 46 and 64, wherein W$_1$ is phenylene.

66. Method according to paragraphs 46 and 64, wherein W$_1$ is 5-7 membered heterocyclic ring system comprising nitrogen, oxygen or sulphur.

67. Method according to paragraph 66, wherein W$_1$ is a 5 membered heterocyclic ring system comprising at least one oxygen.

68. Method according to paragraphs 46 and 64-67, wherein Q$_7$ is —(CH$_2$)$_r$— where r is an integer in the range of from 4 to 22, from 8- to 20, from 12 to 20 or from 14-18.

69. Method according to paragraphs 46 and 64-68, wherein Q$_8$, Q$_9$, Q$_{12}$ and Q$_{13}$ are all a bonds, $v_2$ is 1 and $v_1$ and $v_3$ are zero.

70. Method according paragraph 69, wherein Q$_{10}$ and Q$_{11}$ are oxygen.

71. Method according paragraph 64, wherein X$_4$ and Y$_1$ are a bond and X$_5$ is

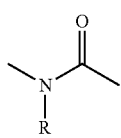

where R is —(CH$_2$)$_p$—COOH, where p is 1-4.

72. Method according to paragraph 64-71, wherein Z$_1$ is —COOH.

73. Method according to paragraphs 46-61, wherein the acylated insulin is having a formula

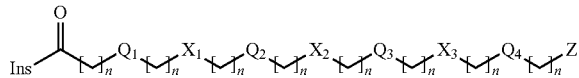

wherein Ins is the parent insulin moiety which via the α-amino group of the N-terminal amino acid residue of the B chain or an ε-amino group of a Lys residue present in the B chain of the insulin moiety is bound to the CO— group in the side chain via an amide bond;
each n is independently 0, 1, 2, 3, 4, 5 or 6;
Q$_1$, Q$_2$, Q$_3$, and Q$_4$ independently of each other can be
$(CH_2CH_2O)_s$—; $(CH_2CH_2CH_2O)_s$—;
$(CH_2CH_2CH_2CH_2O)_s$—;
$(CH_2CH_2OCH_2CH_2CH_2CH_2O)_s$— or
$(CH_2CH_2CH_2OCH_2CH_2CH_2CH_2O)_s$— where s is 1-20
—(CH$_2$)$_r$— where r is an integer from 4 to 22; or a divalent hydrocarbon chain comprising 1, 2 or 3 —CH=CH— groups and a number of —CH$_2$— groups sufficient to give a total number of carbon atoms in the chain in the range of 4 to 22;
—(CH$_2$)$_t$— or —(CH$_2$OCH$_2$)$_t$—, where t is an integer from 1 to 6;
—(CR$_1$R$_2$)$_q$—, where R$_1$ and R$_2$ independently of each other can be H, —COOH, (CH$_2$)$_{1-6}$COOH and R$_1$ and R$_2$ can be different at each carbon, and q is 1-6,
—((CR$_3$R$_4$)$_{q1}$)$_1$—(NHCO—(CR$_3$R$_4$)$_{q1}$—NHCO)$_{1-2}$—((CR$_3$R$_4$)$_{q1}$)$_1$ or —((CR$_3$R$_4$)$_{q1}$)$_1$—(CONH—(CR$_3$R$_4$)$_{q1}$—CONH)$_{1-2}$ —((CR$_3$R$_4$)$_{q1}$—)—,
—((CR$_3$R$_4$)$_{q1}$)$_1$—(NHCO—(CR$_3$R$_4$)$_{q1}$—CONH)$_{1-2}$ ((CR$_3$R$_4$)$_{q1}$)$_1$ or —((CR$_3$R$_4$)$_{q1}$)$_1$—(CONH—(CR$_3$R$_4$)$_{q1}$—NHCO)$_{1-2}$—((CR$_3$R$_4$)$_{q1}$)$_1$ where R$_3$ and R$_4$ independently of each other can be H, —COOH, and R$_3$ and R$_4$ can be different at each carbon, and q$_1$ is 1-6-, or
a bond;
with the proviso that Q$_1$-Q$_4$ are different;
X$_1$, X$_2$ and X$_3$ are independently
O;
a bond; or

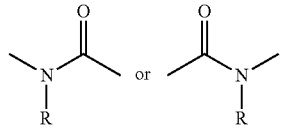

where R is hydrogen or —(CH$_2$)$_p$COOH, —(CH$_2$)$_p$—SO$_3$H, —(CH$_2$)$_p$—PO$_3$H$_2$, —(CH$_2$)$_p$—O—SO$_3$H; —(CH$_2$)$_p$—O—PO$_3$H$_2$; or —(CH$_2$)$_p$-tetrazol-5-yl, where each p independently of the other p's is an integer in the range of 1 to 6; and Z is:
—COOH;
—CO-Asp;
—CO-Glu;
—CO-Gly;
—CO-Sar;
—CH(COOH)$_2$,
—N(CH$_2$COOH)$_2$;
—SO$_3$H
—OSO$_3$H
—OPO$_3$H$_2$
—PO$_3$H$_2$ or
-tetrazol-5-yl
and any Zn$^{2+}$ complex thereof.

74. Method according to paragraph 73, wherein s is in the range of 2-12, 2-4 or 2-3

75. Method according to paragraph 73, wherein s is preferably 1.

76. Method according to paragraph 73-75, wherein Z is COOH.

77. Method according to any of the preceding method paragraphs, wherein the parent insulin is a desB30 human insulin analogue.

78. Method according to any of the preceding method paragraphs, wherein the parent insulin is selected from the group consisting of human insulin; desB1 human insulin; desB30 human insulin; GlyA21 human insulin; GlyA21 desB30 human insulin; AspB28 human insulin; porcine insulin; LysB28 ProB29 human insulin; GlyA21 ArgB31 ArgB32 human insulin; and LysB3 GluB29 human insulin or AspB28 desB30 human insulin.

79. Method according to paragraphs 46-61, 64-72 or 77-78, wherein the acylated insulin is selected from the group consisting of
$N^{\epsilon B29}$—[N—(HOOC(CH$_2$)$_{14}$CO)—N-(carboxyethyl)-CH$_2$—C$_6$H$_4$CO] desB30 human insulin; —$N^{\epsilon B29}$—[N—(HOOC(CH$_2$)$_{13}$CO)—N-(carboxyethyl)-CH$_2$—C$_6$H$_4$CO] desB30 human insulin; $N^{\epsilon B29}$—[N—(HOOC(CH$_2$)$_{15}$CO)—N-(carboxyethyl)-CH$_2$—C$_6$H$_4$CO] desB30 human insulin; $N^{\epsilon B29}$—[N—(HOOC(CH$_2$)$_{16}$CO)—N-(carboxyethyl)-CH$_2$—C$_6$H$_4$CO] desB30 human insulin; $N^{\epsilon B29}$—[N—(HOOC(CH$_2$)$_{14}$CO)—N-(carboxymethyl)-C$_6$H$_4$CO] desB30 human insulin, and $N^{\epsilon B29}$—[N—(HOOC(CH$_2$)$_{14}$CO)—N-(carboxyethyl)-CH$_2$— (furanylene)CO] desB30 human insulin, $N^{\epsilon B29}$-{4-Carboxy-4-[10-(4-carboxy-phenoxy)-decanoylamino]-butyryl} desB30 human insulin 80. Method according to any of paragraphs 46-61 or 73-78, wherein the acylated insulin is selected from the group consisting of $N^{\epsilon B29}$-(3-[2-{2-(2-[(ω-carboxy-pentadecanoyl-γ-glutamyl-(2-amino-ethoxy)]-ethoxy)-ethoxy}-ethoxy]-propionyl) desB30 human insulin, $N^{\epsilon B29}$-(3-[2-{2-(2-[ω-carboxy-heptadecanoyl-γ-glutamyl-(2-amino-ethoxy)]-ethoxy)-ethoxy}-ethoxy]-propinoyl) desB30 human insulin, $N^{\epsilon B29}$-{3-[2-(2-{2-[2-[ω-carboxy-pentadecanoylamino)ethoxy]-ethoxy}-ethoxy)-ethoxy]-propionyl-γ-glutamyl desB30 human insulin, $N^{\epsilon B29}$-(ω-[2-(2-{2-[2-(2-carboxy-ethoxy)-ethoxy]-ethoxy}-ethoxy)-ethylcarbamoyl]-heptadecanoyl-α-glutamyl) desB30 human insulin, $N^{\epsilon B29}$-(ω-[2-(2-{2-[2-(2-carboxy-ethoxy)-ethoxy]-ethoxy}-ethoxy)ethylcarbamoyl]-heptadecanoyl-γ-glutamyl) desB30 human insulin, $N^{\epsilon B29}$-3-[2-(2-{2-[2-(ω-carboxy-heptadecanoylamino)-ethoxy]-ethoxy}-ethoxy)-ethoxy]-propionyl-γ-glutamyl desB30 human insulin, $N^{\epsilon B29}$-(3-(3-{2-[2-(3-[7-carboxyheptanoylamino]propoxy)ethoxy]-ethoxy}propylcarbamoyl)propionyl) desB30 human insulin, $N^{\epsilon B29}$-(3-(3-{4-[3-(7-Carboxyheptanoylamino)propoxy]butoxy}propylcarbamoyl)-propionyl-γ-glutamyl) desB30 human insulin, $N^{\epsilon B29}$-(3-(3-{2-[2-(3-[9-Carboxynonanoylamino]propoxy)ethoxy]-ethoxy}-propylcarbamoyl)propionyl) desB30 human insulin, $N^{\epsilon B29}$-(3-(2-{2-[2-(9-carboxynonanoylamino)ethoxy]-ethoxy}ethylcarbamoyl) propionyl-γ-glutamyl) desB30 human insulin, $N^{\epsilon B29}$-(3-(3-{4-[3-(9-Carboxynonanoylamino)propoxy]butoxy}-propylcarbamoyl)propionyl-γ-glutamyl) desB30 human insulin, $N^{\epsilon B29}$-(2-[3-(2-(2-{2-(7-carboxyheptanoylamino)ethoxy}ethoxy)-ethylcarbamoyl] propionyl-γ-glutamyl) desB30 human insulin, $N^{\epsilon B29}$-(3-[2-(2-{2-[2-(ω-carboxypentadecanoylamino)ethoxy]-ethoxy}ethoxy)ethoxy]-propionyl)) desB30 human insulin, $N^{\epsilon B29}$-(3-(2-{2-[2-(2-{2-[2-(2-{2-[2-(2-{2-[2-(ω-carboxytridecanoylamino)- ethoxy]-ethoxy}-ethoxy)-ethoxy]-ethoxy}-ethoxy]-ethoxy}-ethoxy]-ethoxy)ethoxy]-ethoxy}-ethoxy)-propionoyl-γ-glutamyl) desB30 human insulin, $N^{\epsilon B29}$-(3-[2-(2-{2-[2-(ω-Carboxy-tridecanoylamino)-ethoxy]-ethoxy}-ethoxy)-ethoxy]-propionoyl-γ-glutamyl) desB30 human insulin, $N^{\epsilon B29}$-(3-[2-(2-{2-[2-(2-{2-[2-(ω-carboxy-tridecanoylamino)-ethoxy]-ethoxy}-ethoxy)-ethoxy]-ethoxy}-ethoxy)-ethoxy]-ethoxy}-propionoyl-γ-glutamyl) desB30 human insulin, $N^{\epsilon B29}$-(3-(2-{2-[2-(ω-Carboxy-pentadecanoylamino)-ethoxy]-ethoxy}-ethylcarbamoyl)propionyl-γ-glutamyl) desB30 human insulin, $N^{\epsilon B29}$-(3-(3-{2-[2-(3-[ω-Carboxypentadecanoylamino]propoxy)ethoxy]-ethoxy}propylcarbamoyl)propionyl-γ-glutamyl) desB30 human insulin, $N^{\epsilon B29}$-(3-(3-{4-[3-(ω-Carboxyundecanoylamino)propoxy]butoxypropylcarbamoyl)propionyl-γ-glutamyl) desB30 human insulin, $N^{\epsilon B29}$-(3-(3-{4-[3-(ω-carboxytridecanoylamino)propoxy]butoxypropylcarbamoyl)propionyl-γ-glutamyl) desB30 human insulin, $N^{\epsilon B29}$-(3-(2-{2-[2-(ω-Carboxyundecanoylamino)ethoxy]-ethoxy}ethylcarbamoyl) propionyl-γ-glutamyl) desB30 human insulin, $N^{\epsilon B29}$-(3-(2-{2-[2-(ω-carboxytridecanoylamino)ethoxy] ethoxy}ethylcarbamoyl)propionyl-γ-glutamyl) desB30 human insulin, $N^{\epsilon B29}$-{3-[2-(2-{2-[2-(ω-carboxy-pentadecanoylamino)ethoxy]-ethoxy}ethoxy)ethoxy]propionyl-gamma-γ-D-glutamyl) desB30 human insulin, $N^{\epsilon B29}$-{3-[2-(2-{2-[2-(7-carboxyheptanoylamino)ethoxy]-ethoxy}ethoxy)ethoxy]propionyl-γ-glutamyl} desB30 human insulin, $N^{\epsilon B29}$-{3-[2-(2-{2-[2-(9-carboxynonanoylamino)ethoxy]-ethoxy}ethoxy)ethoxy]propioniyl-γ-glutamyl} desB30 human insulin, $N^{\epsilon B29}$-{3-[2-(2-{2-[2-(ω-carboxyundecanoylamino)ethoxy]-ethoxy}ethoxy)ethoxy]-propionyl-γ-glutamyl} desB30 human insulin, $N^{\epsilon B29}$-{3-[2-(2-{2-[2-(ω-carboxytridecanoylamino)ethoxy]-ethoxy}ethoxy)ethoxy]propionyl-γ-glutamyl} desB30 human insulin.

81. Method according to any of the preceding method paragraphs, wherein a rapid acting insulin is mixed with the composition.

82. Method according to paragraphs 46 and 80, wherein the rapid acting insulin is AspB28 human insulin, LysB3 GluB29 human insulin and/or LysB28 ProB29 human insulin.

83. Use of a composition according to any of the paragraphs 1-45 for the manufacture of a medicament for the treatment of diabetes.

84. A pharmaceutical composition for the treatment of diabetes in a patient in need of such treatment, comprising a therapeutically effective amount of a pharmaceutical composition according to paragraphs 1-45 together with a pharmaceutically acceptable carrier.

85. A method of treating diabetes in a patient in need of such a treatment, comprising administering to the patient a therapeutically effective amount of a pharmaceutical compostion according to paragraphs 1-45 together with a pharmaceutically acceptable carrier.

86. A method according to paragraph 85 for pulmonary treatment of diabetes.

87. Use of a pharmaceutical composition according to paragraph 1-45 for the manufacture of a pharmaceutical composition for the use in the treatment of type 1 diabetes, type 2 diabetes and other states that cause hyperglycaemia.

88. Composition as described in the examples.

Another aspect of the invention is summarised in the following paragraphs.

91. A soluble pharmaceutical composition comprising an acylated insulin and further comprising more than 4 zinc atoms per 6 molecules of acylated insulin.

92. A soluble pharmaceutical composition according to paragraph 91 comprising an acylated insulin and further comprising more than 5 zinc atoms per 6 molecules of acylated insulin.

93. Pharmaceutical composition according to paragraphs 91-92 comprising up to about 14 zinc atoms per 6 molecules of acylated insulin.

94. Pharmaceutical composition according to paragraphs 91-93 comprising between about 5 and about 14 zinc atoms per 6 molecules of acylated insulin.

95. Pharmaceutical composition according to any of paragraphs 91-94 comprising between about 5 and about 13 zinc atoms per 6 molecules of acylated insulin.

96. Pharmaceutical composition according to any of paragraphs 91-95 comprising between about 5 and about 12 zinc atoms per 6 molecules of acylated insulin.

97. Pharmaceutical composition according to any of paragraphs 91-96 comprising between about 5.3 and about 12 zinc atoms per 6 molecules of acylated insulin.

98. Pharmaceutical composition according to any of paragraphs 91-97 comprising between about 5.5 and about 11.4 zinc atoms per 6 molecules of acylated insulin.

99. Pharmaceutical composition according to any of paragraphs 91-98 comprising between about 5.5 and about 10 zinc atoms per 6 molecules of acylated insulin.

100. Pharmaceutical composition according to any of paragraphs 91-99 wherein the acylated insulin is LysB29(Nε-tetradecanoyl)desB30 human insulin or Lys$^{B29}$N$^ε$-lithocholoyl-γ-Glu desB30 human insulin 101. Pharmaceutical composition according to any of paragraphs 91-100 provided that the acylated insulin does not have a side chain attached to the ε-amino group of a Lys residue present in the B chain of the parent insulin, the side chain being of the general formula:

—W—X—Y—Z wherein W is:
  an α-amino acid residue having a carboxylic acid group in the side chain which residue forms, with one of its carboxylic acid groups, an amide group together with ε-amino group of a Lys residue present in the B chain of the parent insulin;
  a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
  a covalent bond from X to an ε-amino group of a Lys residue present in the B chain of the parent insulin;

X is:
  —<u>C</u>O—;
  —CH(COOH)<u>C</u>O—;
  —CO—N(CH$_2$COOH)CH$_2$<u>C</u>O;
  —CO—N(CH$_2$COOH)CH$_2$CON(CH$_2$COOH)CH$_2$<u>C</u>O—;
  —CO—N(CH$_2$CH$_2$COOH)CH$_2$CH$_2$<u>C</u>O—;
  —CO—N(CH$_2$CH$_2$COOH)CH$_2$CH$_2$CON(CH$_2$CH$_2$COOH)CH$_2$CH$_2$<u>C</u>O—;
  —CO—NHCH(COOH)(CH$_2$)$_4$NH<u>C</u>O—;
  —CO—N(CH$_2$CH$_2$COOH)CH$_2$<u>C</u>O—; or
  —CO—N(CH$_2$COOH)CH$_2$CH$_2$<u>C</u>O—.

that
  a) when W is an amino acid residue or a chain of amino acid residues, via a bond from the underscored carbon forms an amide bond with an amino group in W, or
  b) when W is a covalent bond, via a bond from the underscored carbonyl carbon forms an amide bond with an ε-amino group of a Lys residue present in the B chain of the parent insulin;

Y is:
  —(CH$_2$)$_m$— where m is an integer in the range of 6 to 32;
  a divalent hydrocarbon chain comprising 1, 2 or 3 —CH=CH— groups and a number of —CH$_2$— groups sufficient to give a total number of carbon atoms in the chain in the range of 10 to 32; and Z is:
  —COOH;
  —CO-Asp;
  —CO-Glu;
  —CO-Gly;
  —CO-Sar;
  —CH(COOH)$_2$;
  —N(CH$_2$COOH)$_2$;
  —SO$_3$H; or
  —PO$_3$H.

101. Pharmaceutical composition according to any of paragraphs 91-101 provided that the acylated insulin is not Lys$^{B29}$N$^ε$-hexadecandioyl-γ-Glu desB30 human insulin.

102. Pharmaceutical composition according to any of the preceeding paragraphs, having a pH between about 6.5 and 8.5

103. Pharmaceutical composition according to any of the preceding paragraphs further comprising a rapid acting insulin 104. Pharmaceutical composition according to paragraph 103, wherein the rapid acting insulin is AspB28 human insulin and/or LysB28ProB29 human insulin.

109. Method for producing a pharmaceutical composition comprising an acylated insulin wherein more than about 4 zinc atoms per 6 molecules of acylated insulin are added to the composition.

In a further aspect of the invention more than about 4.3 zinc atoms per 6 molecules of acylated insulin are added to the composition or more than about 4.5 zinc atoms per 6 molecules of acylated insulin are added to the composition or than about 5 zinc atoms per 6 molecules of acylated insulin are added to the composition 110. Method according to paragraph 109 wherein up to about 14 zinc atoms per 6 molecules of acylated insulin are added to the composition.

111. Method according to any of paragraphs 109-110 wherein between about 4.3 and about 14 zinc atoms per 6 molecules of acylated insulin are added to the composition.

In a further aspect of the invention between about 4.5 and about 12 zinc atoms per 6 molecules of acylated insulin are added to the composition or more preferred about 5 and about 11.4 zinc atoms per 6 molecules of acylated insulin are added to the composition or even more preferred between about 5.5 and about 10 zinc atoms per 6 molecules of acylated insulin are added to the composition 112. Method according to paragraph 109-111 wherein the zinc is added to the composition before addition of a preservative.

113. Method according to any of the paragraphs 109-112 wherein the number of zinc atoms added before addition of a preservative is more than 1 zinc atom per 6 molecules of acylated insulin.

114. Method according to any of the paragraphs 109-113 wherein the number of zinc atoms added before addition of a preservative is more than 2 zinc atoms per 6 molecules of acylated insulin.
115. Method according to any of the paragraphs 109-114 wherein the number of zinc atoms added before addition of a preservative is more than 3 zinc atoms per 6 molecules of acylated insulin.
116. Method according to any of the paragraphs 109-115 wherein the number of zinc atoms added before addition of a preservative is more than 4 zinc atoms per 6 molecules of acylated insulin.
117. Method according to any of the paragraphs 109-116 wherein the number of zinc atoms added before addition of a preservative is more than 5 zinc atoms per 6 molecules of acylated insulin.

In a further aspect of the invention between about 4.5 and about 12 zinc atoms per 6 molecules of acylated insulin are added to the composition before the addition of a preservative or more preferred about 5 and about 11.4 zinc atoms per 6 molecules of acylated insulin are added to the composition before the addition of a preservative or even more preferred between about 5.5 and about 10 zinc atoms per 6 molecules of acylated insulin are added to the composition before the addition of a preservative 118. Method according to any of the paragraphs 109-111 wherein the zinc is added to the composition after addition of a preservative.
119. Method according to paragraph 118 wherein at least 0.5 zinc atom per 6 molecules of acylated insulin is added to the composition after addition of a preservative.
120. Method according to any of the paragraphs 118-119 wherein at least 1 zinc atom per 6 molecules of acylated insulin is added to the composition after addition of a preservative.

In a further aspect of the invention more than about 2 zinc atoms per 6 molecules of acylated insulin are added to the composition after the addition of a preservative or more than about 3 zinc atoms per 6 molecules of acylated insulin are added to the composition after the addition of a preservative or more than about 4 zinc atoms per 6 molecules of acylated insulin are added to the composition after the addition of a preservative In a further aspect of the invention between about 4.5 and about 12 zinc atoms per 6 molecules of acylated insulin are added to the composition after the addition of a preservative or more preferred about 5 and about 11.4 zinc atoms per 6 molecules of acylated insulin are added to the composition after the addition of a preservative or even more preferred between about 5.5 and about 10 zinc atoms per 6 molecules of acylated insulin are added to the composition after the addition of a preservative 121. Method according to any of the paragraphs 109-120 wherein part of the zinc is added before addition of a preservative and part of the zinc is added after addition of a preservative In one aspect the method comprises adding at least 1 zinc atom per 6 molecules of acylated insulin before addition of a preservative and adding at least 1 zinc atom per 6 molecules of acylated insulin after addition of a preservative or adding at least 1 zinc atom per 6 molecules of acylated insulin before addition of a preservative and adding at least 2-3 zinc atoms per 6 molecules of acylated insulin after addition of a preservative or adding at least 1 zinc atom per 6 molecules of acylated insulin before addition of a preservative and up to about 11 zinc atom per 6 molecules of acylated insulin and after addition of a preservative In one aspect the method comprises adding at least 2 zinc atoms per 6 molecules of acylated insulin before addition of a preservative and adding at least 1 zinc atom per 6 molecules of acylated insulin after addition of a preservative or adding at least 2 zinc atoms per 6 molecules of acylated insulin before addition of a preservative and adding at least 2-3 zinc atoms per 6 molecules of acylated insulin after addition of a preservative or adding at least 2 zinc atoms per 6 molecules of acylated insulin before addition of a preservative and up to about 10 zinc atoms per 6 molecules of acylated insulin after addition of a preservative In one aspect the method comprises adding at least 3 zinc atoms per 6 molecules of acylated insulin before addition of a preservative and adding at least 1 zinc atom per 6 molecules of acylated insulin after addition of a preservative or adding at least 3 zinc atoms per 6 molecules of acylated insulin before addition of a preservative and adding at least 2-3 zinc atoms per 6 molecules of acylated insulin after addition of a preservative or adding at least 3 zinc atoms per 6 molecules of acylated insulin before addition of a preservative and up to about 9 zinc atoms per 6 molecules of acylated insulin after addition of a preservative 122. Method according to any of the paragraph 121 wherein the number of zinc atoms added before addition of a preservative is at least 3 zinc atom per 6 molecules of acylated insulin and the number of zinc atoms added after addition of a preservative are at least 3 zinc atoms per 6 molecules of acylated insulin.
123. Method according to any of the paragraphs 112-122 wherein the preservative is phenol and/or m-cresol.
124. Method according to any of the paragraphs 109-123 wherein the acylated insulin is LysB29(Nε-tetradecanoyl)desB30 human insulin or Lys$^{B29}$N$^{ε}$-lithocholoyl-γ-Glu desB30 human insulin
125. Method according to any of the paragraphs 109-124 provided that the acylated insulin does not have a side chain attached to the ε-amino group of a Lys residue present in the B chain of the parent insulin, the side chain being of the general formula:

—W—X—Y—Z wherein W is:
an α-amino acid residue having a carboxylic acid group in the side chain which residue forms, with one of its carboxylic acid groups, an amide group together with ε-amino group of a Lys residue present in the B chain of the parent insulin;
a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
a covalent bond from X to an ε-amino group of a Lys residue present in the B chain of the parent insulin;

X is:
—CO—;
—CH(COOH)CO—;
—N(CH$_2$COOH)CH$_2$CO—;
—N(CH$_2$COOH)CH$_2$CON(CH$_2$COOH)CH$_2$CO—;
—N(CH$_2$CH$_2$COOH)CH$_2$CH$_2$CO—;
—N(CH$_2$CH$_2$COOH)CH$_2$CH$_2$CON(CH$_2$CH$_2$COOH)CH$_2$CH$_2$CO—;

—NHCH(COOH)(CH$_2$)$_4$NH$\underline{C}$O—;
—N(CH$_2$CH$_2$COOH)CH$_2$$\underline{C}$O—; or
—N(CH$_2$COOH)CH$_2$CH$_2$$\underline{C}$O—.
that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an ε-amino group of a Lys residue present in the B chain of the parent insulin;
Y is:
  —(CH$_2$)$_m$— where m is an integer in the range of 6 to 32;
  a divalent hydrocarbon chain comprising 1, 2 or 3 —CH=CH— groups and a number of —CH$_2$— groups sufficient to give a total number of carbon atoms in the chain in the range of 10 to 32; and
Z is:
  —COOH;
  —CO-Asp;
  —CO-Glu;
  —CO-Gly;
  —CO-Sar;
  —CH(COOH)$_2$;
  —N(CH$_2$COOH)$_2$;
  —SO$_3$H; or
  —PO$_3$H.

126. Method according to any of the paragraphs 125 provided that the acylated insulin is not Lys$^{B29}$N$^ε$-hexadecandioyl-γ-Glu desB30 human insulin.

127. Method according to any of the paragraphs 109-126 wherein a rapid acting insulin is added to the composition.

128. Method according to paragraph 127 wherein the rapid acting insulin is AspB28 human insulin and/or LysB28ProB29 human insulin 129. Use of a composition according to any of the paragraphs 91-104 for the manufacture of a medicament for the treatment of diabetes.

BRIEF DESCRIPTION OF THE DRAWINGS

All figures are the result of size exclusion chromatography of a formulation of Lys$^{B29}$N$^ε$-hexadecandioyl-γ-Glu desB30 human insulin and/or insulin aspart on Superose 6HR eluted by isotonic saline at 37° C. in the upper panels and the content of the respective 14 fractions covering from the high molecular weight fractions to low molecular weight fractions or insulin monomer fractions in the lower panel.

In the figures the following abbreviations are used:
Aspart: insulin aspart
Zn/6Ins: zinc atoms per 6 molecules of insulin
Zn/Acyl-ins: zinc atoms per 6 molecules of acylated insulin
Acyl-ins acylated insulin

DETAILED DESCRIPTION OF THE INVENTION

Figure 1:
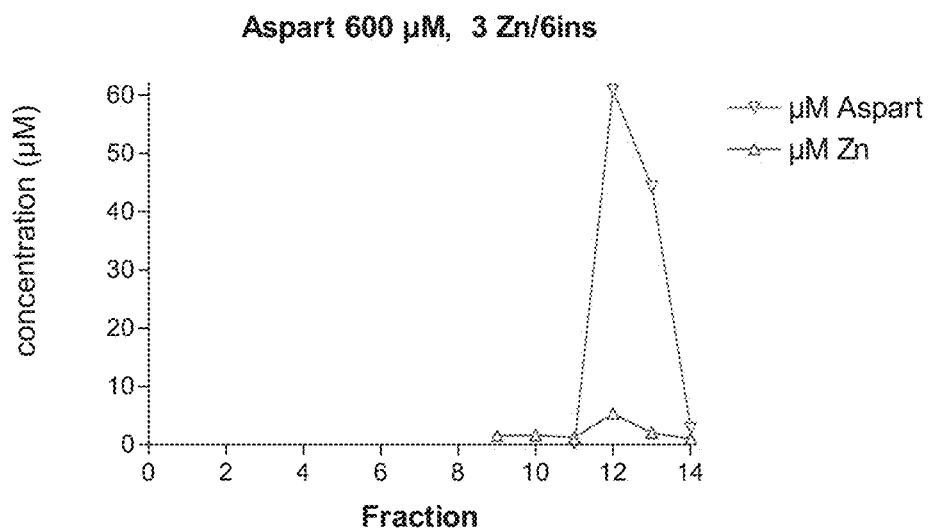
FIG. 1: Insulin aspart 600 μM with 3 zinc atoms per 6 molecules of insulin aspart

The present invention is based on the surprising recognition that an increase in the content of zinc above the usual level (between 2 and 4 zinc atoms per six molecules of acylated insulin) increases the proportion of medium and high molecular weight insulin complexes of certain acylated insulin derivatives, in particular the acylated insulin Lys$^{B29}$N$^ε$-hexadecandioyl-γ-Glu desB30 human insulin.

According to the present invention it is possible to design the insulin formulation containing the insulin with desired degree of association.

Furthermore, when mixing the acylated insulin with rapid acting insulin analogues a true biphasic action profile is obtained as no blunting occurs. Thus the invention provides soluble compositions that are mixtures of a rapid-acting insulin analogue and a prolonged-acting acylated insulin in which the rate of disappearance of the rapid acting insulin and the acylated insulin from the site of injection are the same as when injected in separate compositions. By administering insulin as a biphasic pharmaceutical composition, the number of injections can be reduced resulting in a more convenient and safe therapy.

The present invention is further based on the surprisingly recognition that, when preparing an insulin formulation, zinc can be added to the formulation after addition of preservatives. The zinc is typically provided by adding zinc acetate, zinc chloride or zinc citrate to the insulin formulation.

According to the invention, an acylated insulin composition of this invention may be delivered by inhalation to achieve rapid absorption thereof. Administration by inhalation can result in pharmacokinetics comparable to subcutaneous administration of insulins. Inhalation of an acylated insulin composition of this invention leads to a rapid rise in the level of circulating insulin followed by a rapid fall in blood glucose levels. Different inhalation devices typically provide similar pharmacokinetics when similar particle sizes and similar levels of lung deposition are compared.

According to the invention, an acylated insulin composition of this invention may be delivered by any of a variety of inhalation devices known in the art for administration of a therapeutic agent by inhalation. These devices include metered dose inhalers, nebulizers, dry powder generators, sprayers, and the like. Preferably, an acylated insulin composition of this invention is delivered by a dry powder inhaler or a sprayer. There are a several desirable features of an inhalation device for administering an acylated insulin composition of this invention. For example, delivery by the inhalation device is advantageously reliable, reproducible, and accurate. The inhalation device should deliver small particles, for example, less than about 10 µm, for example about 1-5 µm, for good respirability. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), the C-haler© (Microdrug), the E-flex© (Microdrug) or the like.

As those skilled in the art will recognize, the formulation of an acylated insulin composition of this invention, the quantity of the formulation delivered, and the duration of administration of a single dose depend on the type of inhalation device employed. For some aerosol delivery systems, such as nebulizers, the frequency of administration and length of time for which the system is activated will depend mainly on the concentration of insulin conjugate in the aerosol. For example, shorter periods of administration can be used at higher concentrations of insulin conjugate in the nebulizer solution. Devices such as metered dose inhalers can produce higher aerosol concentrations, and can be operated for shorter periods to deliver the desired amount of insulin conjugate. Devices such as powder inhalers deliver active agent until a given charge of agent is expelled from the device. In this type of inhaler, the amount of insulin derivative of this invention in a given quantity of the powder determines the dose delivered in a single administration.

The particle size of insulin derivative of this invention in the formulation delivered by the inhalation device is critical with respect to the ability of insulin to make it into the lungs, and preferably into the lower airways or alveoli. Preferably, an acylated insulin composition of this invention is formulated so that at least about 10% of the insulin conjugate delivered is deposited in the lung, preferably about 10 to about 20%, or more. It is known that the maximum efficiency of pulmonary deposition for mouth breathing humans is obtained with particle sizes of about 2 µm to about 3 µm. When particle sizes are above about 5 µm pulmonary deposition decreases substantially. Particle sizes below about 1 µm cause pulmonary deposition to decrease, and it becomes difficult to deliver particles with sufficient mass to be therapeutically effective. Thus, particles of an acylated insulin composition delivered by inhalation have a particle size preferably less than about 10 µm, more preferably in the range of about 1 µm to about 5 µm. The formulation of the insulin derivative is selected to yield the desired particle size in the chosen inhalation device.

Advantageously for administration as a dry powder, an acylated insulin composition of this invention is prepared in a particulate form with a particle size of less than about 10 µm, preferably about 1 to about 5 µm. The preferred particle size is effective for delivery to the alveoli of the patient's lung. Preferably, the dry powder is largely composed of particles produced so that a majority of the particles have a size in the desired range. Advantageously, at least about 50% of the dry powder is made of particles having a diameter less than about 10 µm. Such formulations can be achieved by spray drying, milling, or critical point condensation of a solution containing insulin conjugate and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Formulations of acylated insulin of this invention for administration from a dry powder inhaler typically include a finely divided dry powder containing the acylated insulin, but the powder can also include a bulking agent, carrier, excipient, another additive, or the like. Additives can be included in a dry powder formulation of insulin conjugate, for example, to dilute the powder as required for delivery from the particular powder inhaler, to facilitate processing of the formulation, to provide advantageous powder properties to the formulation, to facilitate dispersion of the powder from the inhalation device, to stabilize the formulation (for example, antioxidants or buffers), to provide taste to the formulation, or the like. Advantageously, the additive does not adversely affect the patient's airways. The an acylated insulin can be mixed with an additive at a molecular level or the solid formulation can include particles of the insulin conjugate mixed with or coated on particles of the additive. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulation of a protein such as insulin analogue protein can also be included in the formulation.

A spray including the acylated insulin composition of this invention can be produced by forcing a suspension or solution of insulin conjugate through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of insulin conjugate delivered by a sprayer have a particle size less than about 10 µm, preferably in the range of about 1 µm to about 5 µm.

Formulations of acylated insulin of this invention suitable for use with a sprayer will typically include the insulin derivative in an aqueous solution at a concentration of about 1 mg to about 20 mg of insulin conjugate per ml of solution. The formulation can include agents such as an excipient, a buffer, an isotonicity agent, a preservative, a surfactant, and, preferably, zinc. The formulation can also include an excipient or agent for stabilization of the insulin derivative, such as a buffer, a reducing agent, a bulk protein, or a carbohydrate. Bulk proteins useful in formulating insulin conjugates include albumin, protamine, or the like. Typical carbohydrates useful in formulating insulin conjugates include sucrose, mannitol, lactose, trehalose, glucose, or the like. The insulin derivative formulation can also include a surfactant, which can reduce or prevent surface-induced aggregation of the insulin conjugate caused by atomization of the solution in forming an aerosol. Various conventional surfactants can be employed, such as polyoxyethylene fatty acid esters and alcohols, and polyoxyethylene sorbitol fatty acid esters. Amounts will generally range between about 0.001 and about 4% by weight of the formulation.

The pharmaceutical compositions according to the present invention may be administered parenterally to patients in need of such a treatment. Parenteral administration may be performed by subcutaneous, intramuscular or intravenous injection by means of a syringe, optionally a pen-like syringe or another convenient dosing equipment. Alternatively, parenteral administration can be performed by means of an infusion pump.

One aspect of the invention is related to a pharmaceutical composition according to the invention together with a pharmaceutically acceptable carrier and/or a pharmaceutically acceptable additive, which can be provided for pulmonary treatment of type 1 diabetes, type 2 diabetes and other states that cause hyperglycaemia in patients in need of such a treatment.

In one aspect of the invention, there is provided a method for the manufacture of a pharmaceutical composition for the use in the treatment of type 1 diabetes, type 2 diabetes and other states that cause hyperglycaemia, the composition being used pulmonary and comprising a therapeutically effective amount of a pharmaceutical composition according to the invention together with a pharmaceutically acceptable carrier and/or pharmaceutical acceptable additives.

Injectable compositions of the acylated insulin derivatives can be prepared using the conventional techniques of the pharmaceutical industry which involve dissolving and mixing the ingredients as appropriate to give the desired end product. Thus, according to one procedure, the insulin derivative is dissolved in an amount of water which is somewhat less than the final volume of the composition to be prepared. An isotonic agent, a preservative or a mixture of preservatives, zinc as acetate, citrate or chloride or a mixture thereof, and a buffer can be added as required, furthermore a surfactant might be added and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

The buffer may be selected from the group consisting of sodium acetate, sodium carbonate, citrate, glycine, lysine, arginine, sodium dihydrogen phosphate, disodium hydrogen phosphate, sodium phosphate, ADA (N-[2-acetamido]-2-iminodiacetic acid), ACES (N-[2-acetamido]-2-aminoethanesulfonic acid), BES (N,N-bis[2-hydroxyethyl]-2-aminoethanesulfonic acid), bicine (N,N-bis-[2-hydroxyethyl] glycine), BIS-TRIS (bis[2-hydroxyethyl]iminotris [hydroxymethyl]-methane), DIPSO (3[N,N-bis(2-hydroxethyl]amin]-2-hydroxypropanesulfonic acid), ethylenediamine dihydrochloride, glycylglycine, HEPES (N-[2-hydroxyethyl]piperazine-N'-[2-ethanesulfonic acid]), HEPPSO(N-[2-hydroxyethyl]piperazine-N'-[2-hydroxypropanesulfonic acid]), imidazole, MOBS (4-[N-morpholino] butanesulfonic acid), MOPS (3-[N-morpholino]propanesulfonic acid), PIPES (piperazine-N,N'-bis[2-ethanesulfonic acid]), TAPSO (3-[N-tris(hydroxymethyl)methylamino]-2-hydroxypropanesulfonic acid, THAM (tris[hydroxymethyl]-aminomethan), TES (N-tris[hydroxymethyl]methyl-2-aminoethanesulfonic acid, tricine (N-tris[hydroxymethyl] methylglycine), adipic acid, aspartic acid, glutaric acid, malic acid, malonic acid, succinic acid, and/or salts thereof and/or mixtures thereof.

In a further aspect of the invention the formulation further comprises a pharmaceutically acceptable preservative which may be selected from the group consisting of phenol, o-cresol, m-cresol, p-cresol, methyl p-hydroxybenzoate, propyl phydroxybenzoate, 2-phenoxyethanol, butyl p-hydroxybenzoate, 2-phenylethanol, benzyl alcohol, chlorobutanol, and bronopol, benzoic acid, imidurea, chlorohexidine, sodium dehydroacetate, chlorocresol, ethyl p-hydroxybenzoate, benzethonium chloride, chlorphenesine (3-(4-chlorophenoxy)propane-1,2-diol) or mixtures thereof. In a further aspect of the invention the preservative is present in a concentration from 0.1 mg/ml to 20 mg/ml. In a further aspect of the invention the preservative is present in a concentration from 0.1 mg/ml to 5 mg/ml. In a further aspect of the invention the preservative is present in a concentration from 5 mg/ml to 10 mg/ml. In a further aspect of the invention the preservative is present in a concentration from 10 mg/ml to 20 mg/ml. Each one of these specific preservatives constitutes an alternative aspect of the invention. The use of a preservative in pharmaceutical compositions is well-known to the skilled person. For convenience reference is made to Remington: *The Science and Practice of Pharmacy,* 19$^{th}$ edition, 1995.

In a further aspect of the invention the formulation further comprises an isotonic agent which may be selected from the group consisting of a salt (e.g. sodium chloride), a sugar or sugar alcohol, an amino acid (e.g. 1-glycine, 1-histidine, arginine, lysine, isoleucine, aspartic acid, tryptophan, threonine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one aspect the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one aspect the sugar alcohol additive is mannitol. The sugars or sugar alcohols mentioned above may be used individually or in combination. There is no fixed limit to the amount used, as long as the sugar or sugar alcohol is soluble in the liquid composition and does not adversely effect the stabilizing effects achieved using the methods of the invention. In one aspect, the sugar or sugar alcohol concentration is between about 1 mg/ml and about 150 mg/ml. In a further aspect of the invention the isotonic agent is present in a concentration from 1 mg/ml to 50 mg/ml. In a further aspect of the invention the isotonic agent is present in a concentration from 1 mg/ml to 7 mg/ml. In a further aspect of the invention the isotonic agent is present in a concentration from 8 mg/ml to 24 mg/ml. In a further aspect of the invention the isotonic agent is present in a concentration from 25 mg/ml to 50 mg/ml. Each one of these specific isotonic agents constitutes an alternative aspect of the invention. The use of an isotonic agent in pharmaceutical compositions is well-known to the skilled person. For convenience reference is made to Remington: *The Science and Practice of Pharmacy*, 19$^{th}$ edition, 1995.

In a further aspect of the invention the formulation comprises a surfactant to prevent fibrillation especially when mixing the insulin derivative with a rapid acting insulin as insulin aspart. Various conventional surfactants can be employed, such as polyoxyethylene fatty acid esters and alcohols, and polyoxyethylene sorbitol fatty acid esters. Amounts will generally range between about 0.001 and about 0.1% by weight of the formulation.

Typical isotonic agents are sodium chloride, mannitol, dimethyl sulfone, 1,2 propandiol, and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid), tris-hydroxymethyl-aminomethan, ethylenediamine dihydrochloride, and sodium phosphate.

The pharmaceutical compositions according to the present invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific acylated insulin or mixture of the acylated insulin with a rapid acting insulin employed, the age, body weight, physical activity, and diet of the patient, on a possible combination with other drugs, and on the severity of the state to be treated. It is recommended that the daily dosage of the insulin derivative of this invention be determined for each individual patient by those skilled in the art in a similar way as for known insulin compositions.

The starting product for preparing the acylated insulin or insulin analogue contained in the composition according to the invention can be produced by either well-known peptide synthesis or by well known recombinant production in suitable transformed microorganisms. Thus the insulin starting product can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the insulin polypeptide may suitably be of genomic or cDNA origin, for instance obtained by preparing a genomic or cDNA library and screening for DNA sequences coding for all or part of the polypeptide by hybridisation using synthetic oligonucleotide probes in accordance with standard techniques (see, for example, Sambrook, J, Fritsch, EF and Maniatis, T, *Molecular Cloning: A Laboratory Manual*, Cold Spring Harbor Laboratory Press, New York, 1989). The DNA sequence encoding the polypeptide may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., *Molecular Cloning—a laboratory manual*, second edition 1989.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate.

To direct the insulin peptide into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, E. coli, Saccharomyces cerevisiae, or mammalian BHK or CHO cell lines.

Definitions

The term "effective amount" as used herein means a dosage which is sufficient in order for the treatment of the patient to be effective compared with no treatment.

The term "pharmaceutical composition" as used herein means a product comprising an active compound or a salt thereof together with pharmaceutical excipients such as buffer, preservative and tonicity modifier, said pharmaceutical composition being useful for treating, preventing or reducing the severity of a disease or disorder by administration of said pharmaceutical composition to a person. Thus a pharmaceutical composition is also known in the art as a pharmaceutical formulation. It is to be understood that pH of a pharmaceutical composition which is to be reconstituted is the pH value which is measured on the reconstituted composition produced by reconstitution in the prescribed reconstitution liquid at room temperature.

The term "pharmaceutically acceptable" as used herein means suited for normal pharmaceutical applications, i.e. giving rise to no adverse events in patients etc.

The term "buffer" as used herein refers to a chemical compound in a pharmaceutical composition that reduces the tendency of pH of the composition to change over time as would otherwise occur due to chemical reactions. Buffers include chemicals such as sodium phosphate, TRIS, glycyl glycine and sodium citrate.

The term "preservative" as used herein refers to a chemical compound which is added to a pharmaceutical composition to prevent or delay microbial activity (growth and metabolism). Examples of pharmaceutically acceptable preservatives are phenol, m-cresol and a mixture of phenol and m-cresol.

The term "isotonicity agent" as used refers to a chemical compound in a pharmaceutical composition that serves to modify the osmotic pressure of the pharmaceutical composition so that the osmotic pressure becomes closer to that of human plasma. Isotonicity agents include NaCl, glycerol, mannitol etc.

The term "stabilizer" as used herein refers to chemicals added to peptide containing pharmaceutical compositions in order to stabilize the peptide, i.e. to increase the shelf life and/or in-use time of such compositions. Examples of stabilizers used in pharmaceutical formulations are L-glycine, L-histidine, arginine, polyethylene glycol, and carboxymethylcellulose. Further phenols, zinc ions and sodium chloride can act as stabilizers.

The term "surfactant" as used herein refers to a chemical compound in a pharmaceutical composition that serves to modify the interface to air and hydrophobic surfaces in a way that displaces or partly displaces insulin, insulin analogues and insulin derivatives from the interfaces. Various conventional surfactants can be employed, such as polyoxyethylene fatty acid esters and alcohols, and polyoxyethylene sorbitol fatty acid esters. An example is polysorbate 20.

The term "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The term "prevention of a disease" as used herein is defined as the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders.

The term "human insulin" as used herein means the human hormone whose structure and properties are well known. Human insulin has two polypeptide chains that are connected by disulphide bridges between cysteine residues, namely the A-chain and the B-chain. The A-chain is a 21 amino acid peptide and the B-chain is a 30 amino acid peptide, the two chains being connected by three disulphide bridges: one between the cysteines in position 6 and 11 of the A-chain, the second between the cysteine in position 7 of the A-chain and the cysteine in position 7 of the B-chain, and the third between the cysteine in position 20 of the A-chain and the cysteine in position 19 of the B-chain.

The term "basal insulin" as used herein means an formulation of insulin peptide which has a time-action of more than 15 hours in standard models of diabetes and is suited to cover the need for insulin during the night and in-between meals. Preferably, the basal insulin has a time-action of at least 20 hours. Preferably, the basal insulin has a time-action of at least 10 hours. Preferably, the basal insulin has a time-action in the range from 15 to 48 hours. Preferably, the basal insulin has a time-action similar to that observed for commercial pharmaceutical compositions of NPH insulin or $N^{\varepsilon B29}$-tetradecanoyl desB30 human insulin.

The term "bolus insulin", "meal-related insulin" or "rapid acting insulin" as used herein means an insulin peptide which is rapid-acting and suited to cover the need for insulin during and after the meal.

The term "biphasic insulin" as used herein means a pharmaceutical composition comprising a mixture of "bolus insulin" and "basal insulin".

With "desB30" or "B(1-29)" is meant an insulin B chain or an analogue thereof lacking the B30 amino acid residue and "A(1-21)" means the natural insulin A chain or an analogue thereof. The C-peptide and its amino acid sequence are indicated in the three letter amino acid code. DesB30, desB29 human insulin is a human insulin lacking B29 and B30.

With "B1", "A1" etc. is meant the amino acid residue in position 1 in the B chain of insulin (counted from the N-terminal end) and the amino acid residue in position 1 in the A chain of insulin (counted from the N-terminal end), respectively. The amino acid residue in a specific position may also be denoted as e.g. $Phe^{B1}$ which means that the amino acid residue in position B1 is a phenylalanine residue.

By "insulin analogue" as used herein is meant a polypeptide which has a molecular structure which formally can be derived from the structure of a naturally occurring insulin, for example that of human insulin by deleting and/or exchanging at least one amino acid residue in the naturally occurring insulin and/or adding at least one amino acid residue.

The added and/or exchanged amino acid residues can either be codable amino acid residues or other naturally occurring residues or purely synthetic amino acid residues The insulin analogues may be such wherein position 28 of the B chain may be modified from the natural Pro residue to one of Asp, Lys, or Ile. In another aspect Lys at position B29 is modified to Pro. In one aspect B30 may be Lys and then B29 can be any codable amino acid except Cys, Met, Arg and Lys.

Also, Asn at position A21 may be modified to Ala, Gln, Glu, Gly, H is, Ile, Leu, Met, Ser, Thr, Trp, Tyr or Val, in particular to Gly, Ala, Ser, or Thr and preferably to Gly. Furthermore, Asn at position B3 may be modified to Lys or Asp. Further examples of insulin analogues are desB30 human insulin; desB30 human insulin analogues; insulin analogues wherein PheB1 has been deleted; insulin analogues wherein the A-chain and/or the B-chain have an N-terminal extension and insulin analogues wherein the A-chain and/or the B-chain have a C-terminal extension. Thus one or two Arg may be added to position B1 or to position B30.

In one aspect an insulin analogue comprises less than 6 modifications (substitutions, deletions, additions) relative to the native peptide. In another aspect an analogue comprises less than 5 modifications (substitutions, deletions, additions) relative to the native peptide. In another aspect an analogue comprises less than 4 modifications (substitutions, deletions, additions) relative to the native peptide. In another aspect an analogue comprises less than 3 modifications (substitutions, deletions, additions) relative to the native peptide. In another aspect an analogue comprises less than 2 modifications (substitutions, deletions, additions) relative to the native peptide. In another aspect an analogue comprises only a single modification (substitutions, deletions, additions) relative to the native peptide.

By "insulin derivative" as used herein is meant a naturally occurring insulin or an insulin analogue which has been chemically modified, e.g. by introducing a side chain in one or more positions of the insulin backbone or by oxidizing or reducing groups of the amino acid residues in the insulin or by converting a free carboxylic group to an ester group or acylating a free amino group or a hydroxy group.

By "acylated insulin" as used herein is meant a naturally occurring insulin, for example that of human insulin, an insulin molecule, an insulin derivative or an insulin analogue which has been chemically modified, by acylating a free amino group or a hydroxy group.

The term "no blunting" as used herein means that when formulated in one formulation both the rapid acting insulin and the acylated insulin has profile of action which is identical or substantially identical with the profile of action, when administering the rapid acting insulin and the acylated insulin in separate formulations.

The term "OAD" or "OAD(s)" as used herein means oral antidiabetic drug or oral antidiabetic drugs. An unlimited list of OAD(s) can be sulfonylurea (SU), biguanides e.g. Melformin or thiozolidindiones (TZD).

The expression "a codable amino acid" or "a codable amino acid residue" is used to indicate an amino acid or amino acid residue which can be coded for by a triplet ("codon") of nucleotides.

hGlu is homoglutamic acid.
α-Asp is the L-form of —HNCH(CO—)CH$_2$COOH.
β-Asp is the L-form of —HNCH(COOH)CH$_2$CO—.
α-Glu is the L-form of —HNCH(CO—)CH$_2$CH$_2$COOH.
γ-Glu is the L-form of —HNCH(COOH)CH$_2$CH$_2$CO—.
α-hGlu is the L-form of —HNCH(CO—)CH$_2$CH$_2$CH$_2$COOH.
δ-hGlu is the L-form of —HNCH(COOH)CH$_2$CH$_2$CH$_2$CO—.
β-Ala is —NH—CH$_2$—CH$_2$—COOH.
Sar is sarcosine (N-methylglycine).

The expression "an amino acid residue having a carboxylic acid group in the side chain" designates amino acid residues like Asp, Glu and hGlu. The amino acids can be in either the L- or D-configuration. If nothing is specified it is understood that the amino acid residue is in the L configuration.

The expression "an amino acid residue having a neutral side chain" designates amino acid residues like Gly, Ala, Val, Leu, Ile, Phe, Pro, Ser, Thr, Cys, Met, Tyr, Asn and Gln.

When an insulin derivative according to the invention is stated to be "soluble at physiological pH values" it means that the insulin derivative can be used for preparing injectable insulin compositions that are fully dissolved at physiological pH values. Such favourable solubility may either be due to the inherent properties of the insulin derivative alone or a result of a favourable interaction between the insulin derivative and one or more ingredients contained in the vehicle.

The expression "high molecular weight insulin" or "hmw" means that the molecular weight of a complex of human insulin, of an insulin analogue or of an insulin derivative is above human serum albumin, above a dodecameric complex of an insulin analogue or of an insulin derivative or more than about 72 kDalton.

The expression "medium molecular weight insulin" or "mmw" means that the molecular weight of a complex of human insulin, of an insulin analogue or of an insulin derivative is from about an insulin hexamer to about an insulin dodecamer between 24 and 80 kDalton The expression "low molecular weight insulin" or "lmw" means that the molecular weight of a human insulin, an insulin analogue or an insulin derivative is below 24 kDalton The expression "net charge" means the overall charge of the molecule. At pH 7.4, human insulin has a negative net charge about −3 or when forming a hexamer about −2.5 per insulin monomer.

The following abbreviations have been used in the specification and examples:
hGlu homoglutamic acid
Sar: Sarcosine (N-methyl-glycine)
S.c. subcutaneous
Acyl ins Acylated insulin
Ins insulin All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

Example 1

A: Insulin aspart 600 µM, 3 Zn/6 insulin, 1.6% glycerol, 16 mM phenol and 16 mM m-cresol, 7 mM trishydroxymethylaminomethan, 10 mM NaCl, pH 7.5 and volume of 8 mL: 31 mg insulin aspart was suspended in 2 ml water and 30 µL 1 N HCl added to obtain a solution. 240 µL 10 mM Zn(AcO)$_2$ was then added followed by 3200 µL 4% glycerol, 400 µL 0.32 M phenol, 800 µL m-cresol, 560 µL 0.1 M trishydroxymethylaminomethan, 160 µL 0.5 M NaCl and pH was then adjusted to 7.5 by 1N NaOH and finally the volume to adjusted to 8 mL by water. The solution was filtered through a 0.22 µm sterile filter.

B: LysB29Nε-hexadecandioyl-γ-Glu desB30 human insulin 1200 µM, 3 Zn/6ins, 1.6% glycerol, 16 mM phenol and 16 mM m-cresol, 7 mM trishydroxymethylaminomethan, 10 mM NaCl, pH 7.5 and volume of 7 mL:

58 mg LysB29Nε-hexadecandioyl-γ-Glu desB30 human insulin was suspended and dissolved in 2 mL water and subsequent added 420 µL 10 mM Zn(AcO)$_2$, 2800 µL 4% glycerol, 350 µL 0.32 M phenol, 700 µL m-cresol, 490 µL 0.1 M trishydroxymethylaminomethan, 140 µL 0.5 M NaCl and finally addition of 1 N NaOH adjusting to pH 7.5 and water to obtain 7 mL. The solution was filtered through a 0.22 µm sterile filter.

C: Insulin aspart 600 µM, 4 Zn/6ins, 1.6% glycerol, 16 mM phenol and 16 mM m-cresol, 7 mM trishydroxymethylaminomethan, 10 mM NaCl, pH 7.5 and volume of 15 mL:

The formulation was prepared analogous to formulation A.

D: LysB29Nε-hexadecandioyl-γ-Glu desB30 human insulin 1200 µM, 4 Zn/6ins, 1.6% glycerol, 16 mM phenol and 16 mM m-cresol, 7 mM trishydroxymethylaminomethan, 10 mM NaCl, pH 7.5 and volume of 20 mL: The formulation was prepared analogous to formulation B.

E: Insulin aspart 600 µM, 6 Zn/6ins, 1.6% glycerol, 16 mM phenol and 16 mM m-cresol, 7 mM trishydroxymethylaminomethan, 10 mM NaCl, pH 7.5:

The formulation was prepared as C and finally adding 20 µL 10 mM Zn(AcO)$_2$ per mL and adjusting pH to 7.5.

F: LysB29Nε-hexadecandioyl-γ-Glu desB30 human insulin 1200 µM, 6 Zn/6ins, 1.6% glycerol, 16 mM phenol and 16 mM m-cresol, 7 mM trishydroxymethylaminomethan, 10 mM NaCl, pH 7.5:

The formulation was prepared as D and finally adding 40 µL 10 mM Zn(AcO)$_2$ per mL and adjusting pH to 7.5.

G: Insulin aspart 600 µM, 8 Zn/6ins, 1.6% glycerol, 16 mM phenol and 16 mM m-cresol, 7 mM trishydroxymethylaminomethan, 10 mM NaCl, pH 7.5:

The formulation was prepared as C and finally adding 40 µL 10 mM Zn(AcO)$_2$ per mL and adjusting pH to 7.5

H: LysB29Nε-hexadecandioyl-γ-Glu desB30 human insulin 1200 µM, 8 Zn/6ins, 1.6% glycerol, 16 mM phenol and 16 mM m-cresol, 7 mM trishydroxymethylaminomethan, 10 mM NaCl, pH 7.5:

The formulation was prepared as D and finally adding 80 µL 10 mM Zn(AcO)$_2$ per mL and adjusting pH to 7.5.

Medium: 1.6% glycerol, 16 mM phenol and 16 mM m-cresol, 7 mM tris-hydroxymethylaminomethan, 10 mM NaCl, pH 7.5.

Formulations of LysB29Nε-hexadecandioyl-γ-Glu desB30 human insulin 600 µM and Zn/6 acyl-ins varied at 3, 4, 6, and 8 were obtained by dilution of the above mentioned formulation B, D, F, and H with an equal amount of medium. The formulations were tested by size exclusion chromatography for the ability to form high molecular weight insulin on a Superose 6HR column eluted with 140 mM NaCl, 10 mM trishydroxymethylaminomethan pH 7.4, and 0.01% NaN$_3$ at 37° C. and 0.25 mL/min. Fractions were collected for every 4 minutes starting at the high molecular weight exclusion limit and ending with the last of the monomer peak, in total 14 fractions. The fraction concentration of insulin analogue was quantified specifically by reverse phase chromatography and the concentration of zinc after addition of the chromophoric zinc chelator terpy at an pH 2.5 excursion (FIGS. 3,4,5 and 6). The relative amount of LysB29Nε-hexadecandioyl-γ-Glu desB30 human insulin with a size larger than albumin (fraction [1-8]) was measured at 3, 4, 6, and 8 Zn/6 insulin to 67.4, 88.9, 98.0, and 97.9% respectively. Furthermore the zinc concentration was following LysB29Nεhexadecandioyl-γ-Glu desB30 human insulin especially in the high molecular size fractions.

Figure 2:
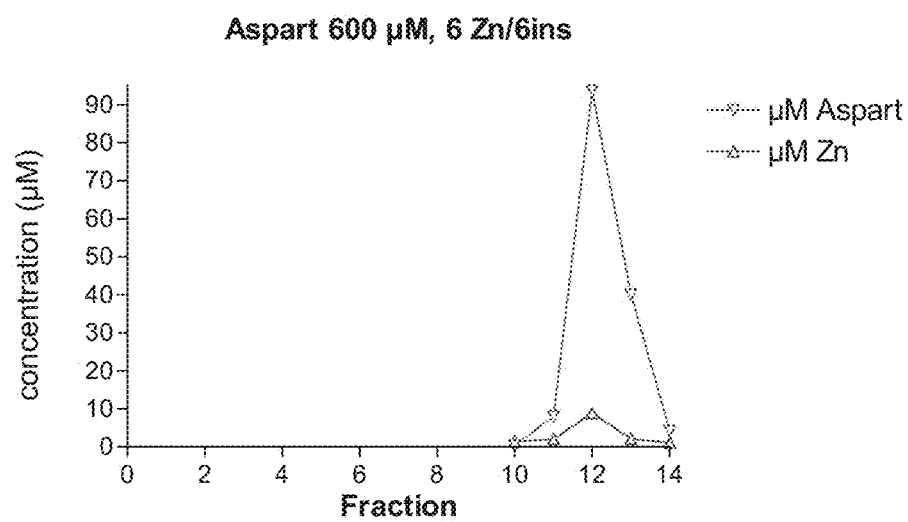
FIG. 2: Insulin aspart 600 μM with 6 zinc atoms per 6 molecules of insulin aspart
Figure 3:
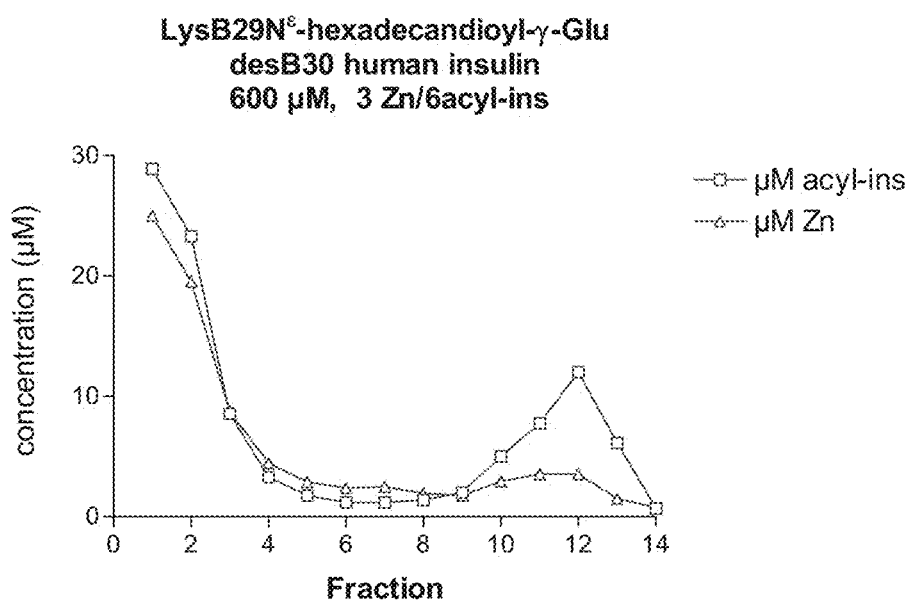
FIG. 3: Lys$^{B29}$N$^ε$-hexadecandioyl-γ-Glu desB30 human insulin 600 μM with 3 zinc atoms per 6 molecules of acylated insulin
Figure 4:
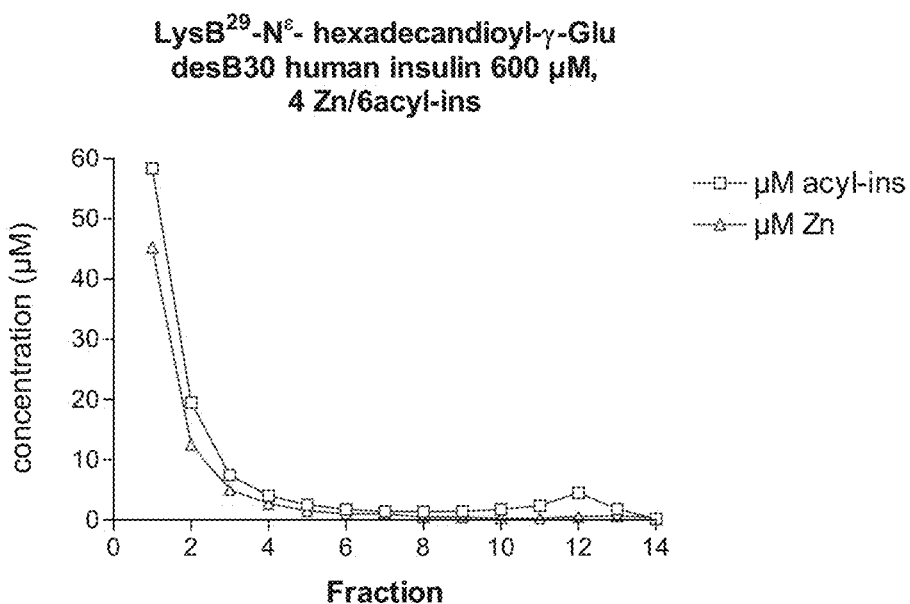
FIG. 4: Lys$^{B29}$N$^ε$-hexadecandioyl-γ-Glu desB30 human insulin 600 μM with 4 zinc atoms per 6 molecules of acylated insulin

Formulation consisting of insulin aspart 600 µM (A and E) varied at 3 and 6 zinc/insulin eluted as monomer (fraction [12-13]) only followed by minor part of the added zinc, see FIGS. 1-2.

Mixing of an Insulin Analogue and an Acylated Insulin

Figure 5:
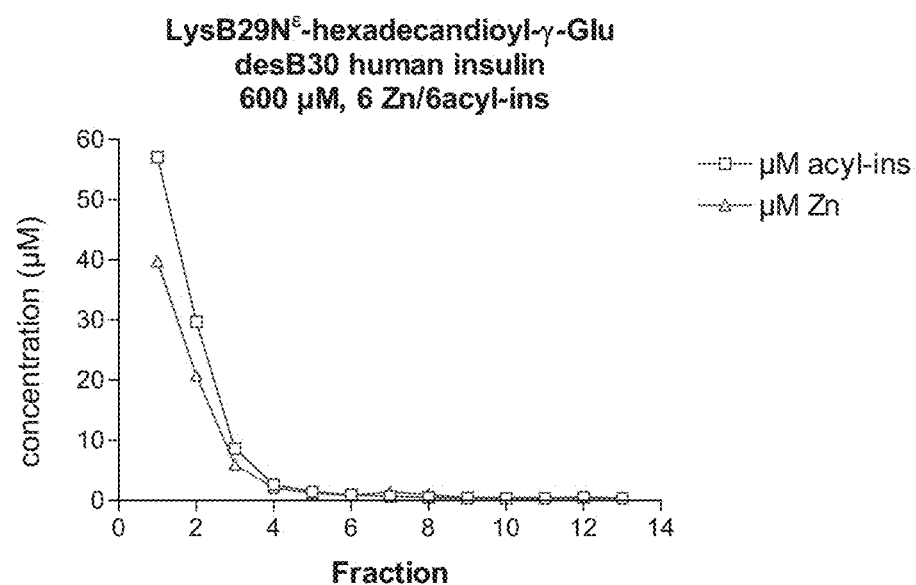
FIG. 5: Lys$^{B29}$N$^ε$-hexadecandioyl-γ-Glu desB30 human insulin 600 μM with 6 zinc atoms per 6 molecules of acylated insulin
Figure 6:
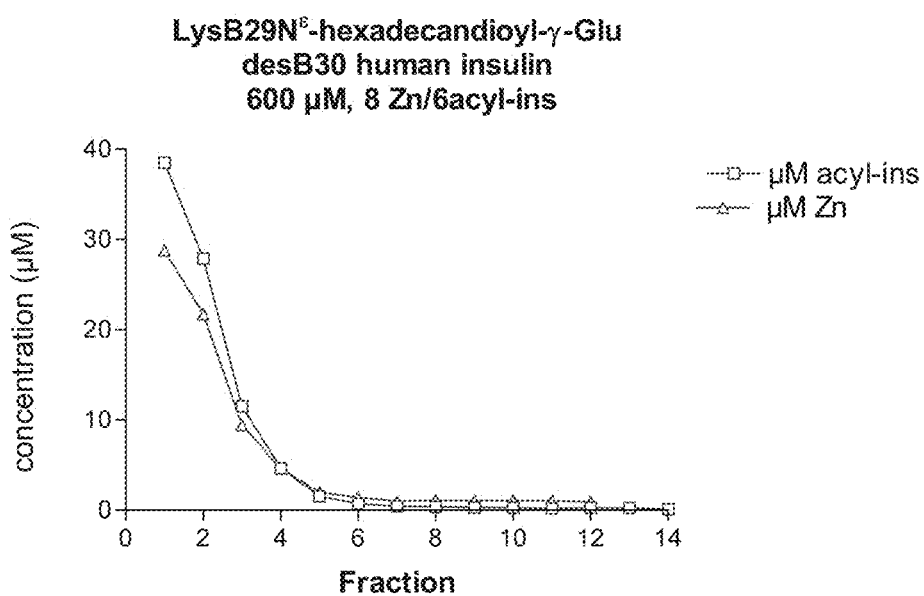
FIG. 6: Lys$^{B29}$N$^ε$-hexadecandioyl-γ-Glu desB30 human insulin 600 μM with 8 zinc atoms per 6 molecules of acylated insulin
Figure 7:
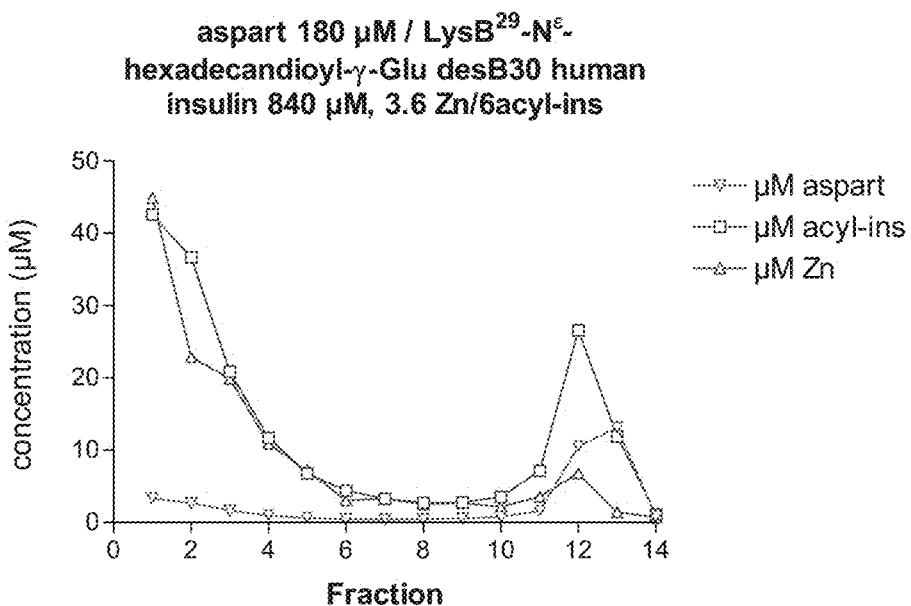
FIG. 7: Mixture of Insulin aspart 180 μM and Lys$^{B29}$N$^ε$-hexadecandioyl-γ-Glu desB30 human insulin 840 μM with a total zinc content of 3.6 zinc atoms per 6 molecules of acylated insulin
Figure 8:
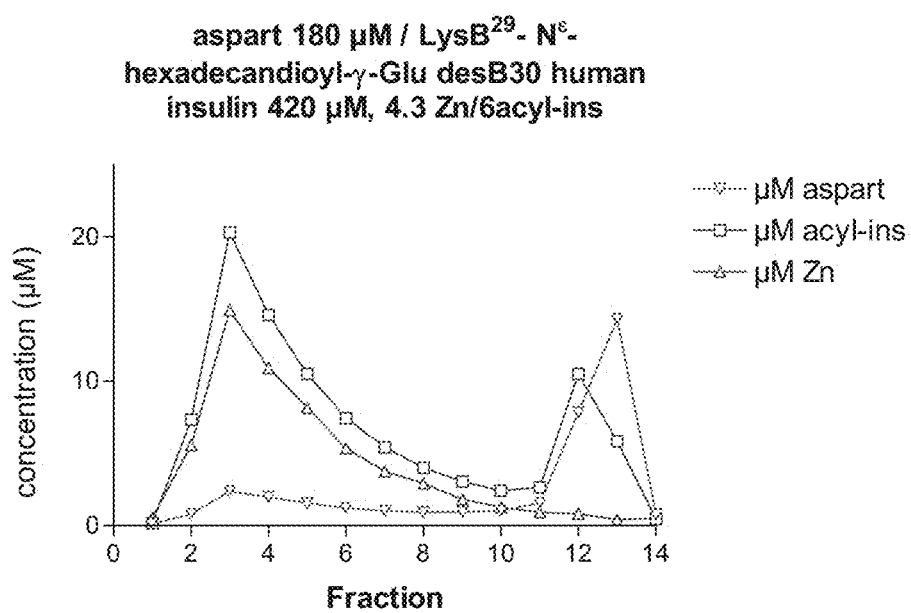
FIG. 8: Mixture of Insulin aspart 180 μM and Lys$^{B29}$N$^ε$-hexadecandioyl-γ-Glu desB30 human insulin 420 μM with a total zinc content of 4.3 zinc atoms per 6 molecules of acylated insulin
Figure 9:
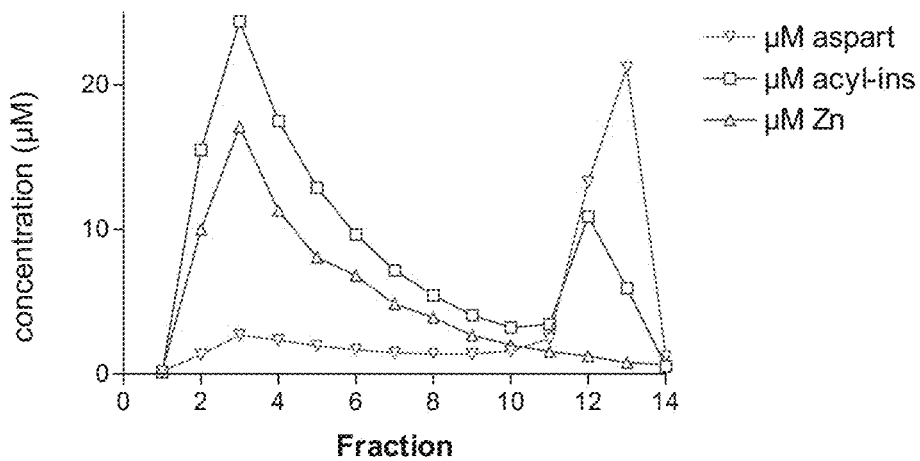
FIG. 9: Mixture of Insulin aspart 300 μM and Lys$^{B29}$N$^ε$-hexadecandioyl-γ-Glu desB30 human insulin 600 μM with a total zinc content of 4.5 zinc atoms per 6 molecules of acylated insulin
Figure 10:
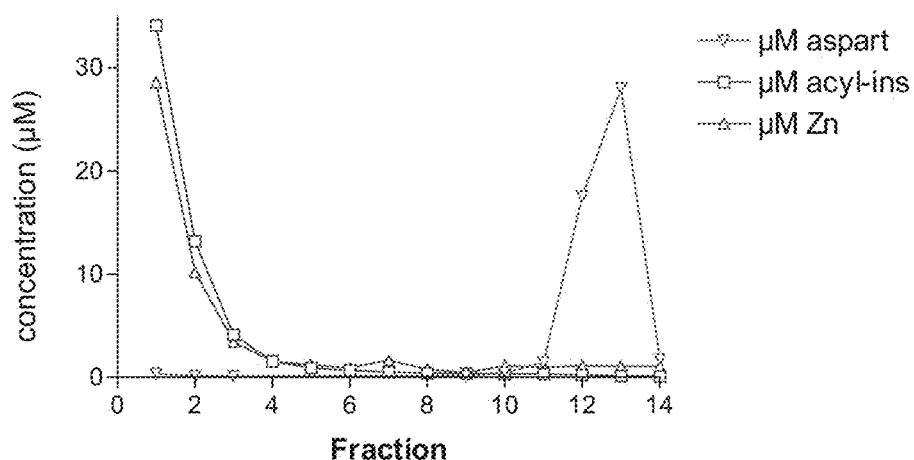
FIG. 10: Mixture of Insulin aspart 180 μM and Lys$^{B29}$N$^ε$-hexadecandioyl-γ-Glu desB30 human insulin 420 μM with a total zinc content of 8.6 zinc atoms per 6 molecules of acylated insulin
Figure 11:
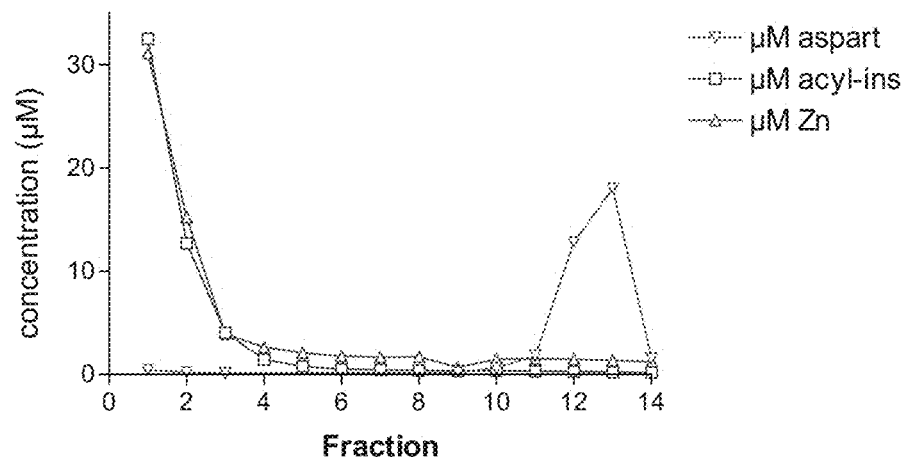
FIG. 11: Mixture of Insulin aspart 180 μM and Lys$^{B29}$N$^ε$-hexadecandioyl-γ-Glu desB30 human insulin 420 μM with a total zinc content of 11.4 zinc atoms per 6 molecules of acylated insulin
Figure 12:
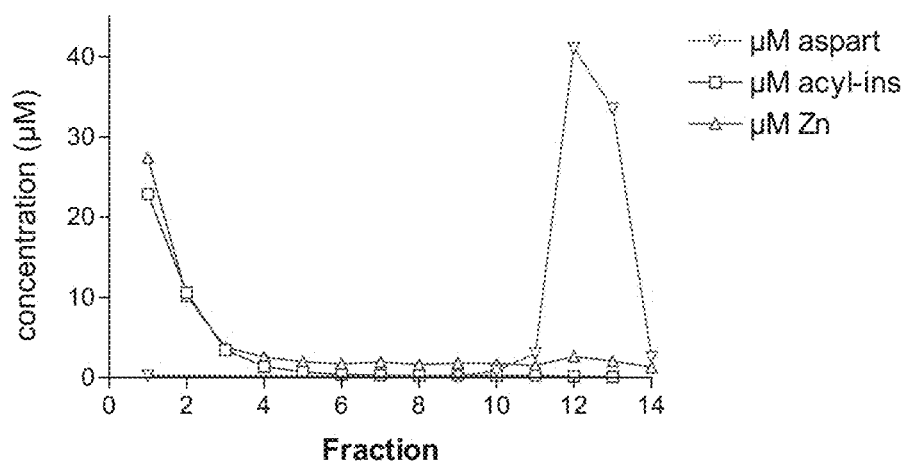
FIG. 12: Mixture of Insulin aspart 300 μM and Lys$^{B29}$N$^ε$-hexadecandioyl-γ-Glu desB30 human insulin 300 μM with a total zinc content of 12 zinc atoms per 6 molecules of acylated insulin FIG. 13. Plasma profile of insulin Aspart given separately (IV, dashed line, N=8) and given in mix with B29Nε-hexadecandioyl-γ-Glu desB30 insulin at low zinc concentration (I, 3.38 Zn/6ins.deriv., full line, N=8) and at high zinc concentration (II, 6 Zn/6ins.deriv., dotted line, N=7).

Formulations consisting of insulin 180 µM aspart and 420 µM LysB29Nεhexadecandioyl-γ-Glu desB30 human insulin and zinc concentration varied at 3, 6, and 8 Zn/6insulin were obtained by mixing the above stock solution A to H and the mentioned medium in an analogous manner. An example of calculating the concentration of zinc/6 acylated insulin is mixing 180 µM aspart with 3 Zn/6insulin and 420 µM LysB29Nε-hexadecandioyl-γ-Glu desB30 human insulin with 3 Zn/6acyl-ins makes 4.3 Zn/6 acylated insulin [(180*3+420*3)/420=4.3 Zn/acyl-ins]. The formulations were tested by size exclusion chromatography for the ability to form high molecular weight insulin on a Superose 6HR column, and fractions were similarly collected for quantification of both insulin analogues and zinc. As seen from FIG. 8 the analogues mixing with 3 Zn/6insulin corresponding to a formulation of 4.3 Zn/6 acyl-insulin showed predominantly LysB29Nε-hexadecandioyl-γ-Glu desB30 human insulin (72.5% of LysB29Nε-hexadecandioyl-γ-Glu desB30 human insulin) and zinc in the high molecular weight fractions [1-8], but also insulin aspart, whereas an equal amount of insulin aspart and LysB29Nε-hexadecandioyl-γ-Glu desB30 human insulin was measured as mean in the rest of the fractions [9-14](FIG. 8). The testing of insulin aspart and LysB29Nεhexadecandioyl-γ-Glu desB30 human insulin consisting of 6 Zn/6ins are shown in FIG. 2 and FIG. 5 respectively. Mixing the two formulations of 6 Zn/6ins (FIG. 2. and FIG. 5) to aspart 180 µM+LysB29Nε-hexadecandioyl-γ-Glu desB30 human insulin 420 µM corresponding to 8.6 Zn/6acyl-ins showed a completely separated fraction of LysB29Nε-hexadecandioyl-γ-Glu desB30 human insulin at the high molecular weight and insulin aspart at low molecular weight (FIG. 10). Mixing at equal concentration of insulin aspart and LysB29Nεhexadecandioyl-γ-Glu desB30 human insulin to 12 Zn/6acyl-ins showed separated fractions as well (FIG. 12). Further increased concentration of zinc to 8 Zn/6ins in the individual formulations is shown in for LysB29Nε-hexadecandioyl-γ-Glu desB30 human insulin in FIG. 6 and the mix of aspart 180 µM+LysB29Nε-hexadecandioyl-γ-Glu desB30 human insulin 420 µM in FIG. 11.

As is clear from the figures, the increased amount of zinc surpricingly induced a separation of insulin aspart and LysB29Nε-hexadecandioyl-γ-Glu desB30 human insulin in the pharmaceutical preparation, resulting in no significant blunting between the analogues.

an increased amount of zinc induced a separation of insulin aspart and LysB29Nεhexadecandioyl-γ-Glu desB30 human insulin in the pharmaceutical preparation in a way that the analogues showed actually no blunting.

Example 2

2A: 3 Zn/6 Acylated Insulin Added Before Phenol and m-Cresol

LysB29Nε-hexadecandioyl-γ-Glu desB30 human insulin 600 μM, 3 Zn/6insulin, 1.6% glycerol, 16 mM phenol and 16 mM m-cresol, 20 mM NaCl, 7 mM phosphate, pH 7.5, 1.5 μCi $^{125}$I-Tyr$^{414}$-LysB29Nε-hexadecandioyl-γ-Glu desB30 human insulin tracer, and volume of 2 mL. 8.2 mg LysB29Nε-hexadecandioyl-γ-Glu desB30 human insulin was dissolved in 400 μL water and 3 μCi $^{125}$I-Tyr$^{414}$-LysB29Nε-hexadecandioyl-γ-Glu desB30 human insulin tracer was added, followed by 800 μL 4% glycerol and treated for 10-15 min in a vacuum centrifuge to remove added ethanol included in the tracer solution. 60 μL 10 mM Zn(AcO)$_2$ was added and with 2 minutes interval followed by 100 μL 0.32 M phenol, 200 μL 0.16 M m-cresol, 80 μL 0.5 M NaCl, and 140 μL 0.1 M sodium phosphate and pH adjusted to pH 7.5 mM and a total volume of 2 mL. The solution was filtered through a sterile 0.22 μm filter and used for a disappearance study after subcutaneous injection in pig. $T_{50\%}$±SEM (h) was determined to 9.6±0.7 h as described under assay in a cross over study of formulation examples 2A to 2D.

2B: 3 Zn/6 Acylated Insulin Added Before and 3 Zn/6 Acylated Insulin Added after Phenol and m-Cresol LysB29Nε-hexadecandioyl-γ-Glu desB30 human insulin 600 μM, 3 Zn/6 acylated insulin added before and 3 Zn/6 acylated insulin added after, 1.6% glycerol, 16 mM phenol and 16 mM m-cresol, 20 mM NaCl, 7 mM phosphate, pH 7.5, 1.5 μCi Iodine-I$^{125}$-Tyr$^{414}$-LysB29Nεhexadecandioyl-γ-Glu desB30 human insulin tracer, and volume of 2 mL. 8.2 mg LysB29Nε-hexadecandioyl-γ-Glu desB30 human insulin was dissolved in 400 μL water and 3 μCi $^{125}$I-Tyr$^{414}$-LysB29Nε-hexadecandioyl-γ-Glu desB30 human insulin tracer was added, followed by 800 μL 4% glycerol and treated for 10-15 min in a vacumcentrifuge to remove added ethanol included in the tracer solution. 60 μL 10 mM Zn(AcO)$_2$ was added and with 2 minutes interval followed by 100 μL 0.32 M phenol, 200 μL 0.16 M m-cresol, 60 μL 10 mM Zn(AcO)$_2$, 80 μL 0.5 M NaCl, and 140 μL 0.1 M sodium phosphate and adjusted to pH 7.5 mM and a total volume of 2 mL. The solution was filtered through a sterile 0.22 μm filter and used for a disappearance study after subcutaneous injection in pig. $T_{50\%}$±SEM (h) was determined to 11.9±1.0 h as described under assay in a cross over study of formulation examples 2A to 2D.

2C: 3 Zn/6 Acylated Insulin Added Before and 3 Zn/6 Acylated Insulin after Phenol and m-Cresol and not Included Buffer LysB29Nε-hexadecandioyl-γ-Glu desB30 human insulin 600 μM, 3 Zn/6 acylated insulin added before and 3 Zn/6 acylated insulin added after, 1.6% glycerol, 16 mM phenol and 16 mM m-cresol, 20 mM NaCl, pH 7.5, 1.5 μCi $^{125}$I-Tyr$^{414}$-LysB29Nε-hexadecandioyl-γ-Glu desB30 human insulin tracer, and volume of 2 mL.

8.2 mg LysB29Nε-hexadecandioyl-γ-Glu desB30 human insulin was dissolved in 400 μL water and 3 μCi $^{125}$I-Tyr$^{414}$-LysB29Nε-hexadecandioyl-γ-Glu desB30 human insulin tracer was added, followed by 800 μL 4% glycerol and treated for 10-15 min in a vacumcentrifuge to remove added ethanol included in the tracer solution. 60 μL 10 mM Zn(AcO)$_2$ was added and with 2 minutes interval followed by 100 μL 0.32 M phenol, 200 μL 0.16 M m-cresol, 60 μL 10 mM Zn(AcO)$_2$, 80 μL 0.5 M NaCl, and adjusted to pH 7.5 mM. The solution was filtered through a sterile 0.22 μm filter and used for a disappearance study after subcutaneous injection in pig. $T_{50\%}$±SEM (h) was determined to 14.4±2.4 h as described under assay in a cross over study of formulation examples 2A to 2D.

2D: 6 Zn/6 Acylated Insulin Added after Phenol and m-Cresol and not Included Buffer LysB29Nε-hexadecandioyl-γ-Glu desB30 human insulin 600 μM, 6 Zn/6 acylated insulin added after, 1.6% glycerol, 16 mM phenol and 16 mM m-cresol, 20 mM NaCl, 7 mM phosphate, pH 7.5, 1.5 μCi $^{125}$I-Tyr$^{414}$-LysB29Nε-hexadecandioyl-γ-Glu desB30 human insulin tracer, and volume of 2 mL.

8.2 mg LysB29Nε-hexadecandioyl-γ-Glu desB30 human insulin was dissolved in 400 μL water and 3 μCi $^{125}$I-Tyr$^{414}$-LysB29Nε-hexadecandioyl-γ-Glu desB30 human insulin tracer was added, followed by 800 μL 4% glycerol and treated for 10-15 min in a vacuum centrifuge to remove added ethanol included in the tracer solution. 100 μL 0.32 M phenol was added and with 2 minutes interval followed by 200 μL 0.16 M m-cresol, 120 μL 10 mM Zn(AcO)$_2$, 80 μL 0.5 M NaCl, and adjusted to pH 7.5 mM and a total volume of 2 mL. The solution was filtered through a sterile 0.22 μm filter and used for a disappearance study after subcutaneous injection in pig. $T_{50\%}$±SEM (h) was determined to 13.5±1.7 h as described under assay in a cross over study of formulation examples 2A to 2D.

Example 3

Isolation of LysB29Nε-Hexadecandioyl-γ-Glu desB30 Human Insulin by Crystallisation LysB29Nε-hexadecandioyl-γ-Glu desB30 human insulin can be crystallized as a hexamer with a zinc content of 2-6 mol zinc per 6 mol insulin and an excess of a phenol-like molecule (preferred phenol). As precipitants, ionic salts are used with NaCl being preferred. Furthermore crystallisation can be enhanced by adding small amounts of organic solvents (ethanol).

Preparation of a Protein Solution (Solution A):

40.5 mg freeze-dried LysB29Nε-hexadecandioyl-γ-Glu desB30 human insulin is suspended in 4 ml 0.02 mol/l trishydroxymethylaminomethan buffer (adjusted to pH 7.0 with HCl).

To 1.8 ml of this LysB29Nε-hexadecandioyl-γ-Glu desB30 human insulin solution is added 69.5 μl of a solution containing 0.010 mol/l Zn(OAc)$_2$ in water, and 18 μl of a solution containing 2 mol/l Phenol in ethanol.

Preparation of the Precipitant Solution (Solution B):

To a 5 ml of a solution containing 0.1M trishydroxymethylaminomethan (adjusted to pH 7.5 with HCl) is added 1.75 g NaCl and 1 ml Ethanol and the final volume adjusted to 10 ml.

Crystallisation:

Equal amounts (typically 500 µl) of solution A and solution B are mixed in a glass vial. Crystallisation is complete after 12 h at room temperature and the resulting crystals can be isolated by filtration or centrifugation.

Example 4

Formulation

B29Nε-hexadecandioyl-γ-Glu desB30 insulin (to 600 µM) was suspended in water and dissolved by addition of sodium hydroxide, and added in following order: glycerol 1.6%, phenol and 16 mM m-cresol 16 mM, zinc acetate 0 to 6 Zn/bins, sodium chloride 10 mM, phosphate 7 mM, pH 7.5, and water to volume adjustment.

SEC Method:

Analysis by size exclusion chromatography (SEC) on a Superose 6 PC column (0.32*30 cm) using isotonic 10 mM tris-buffered saline optionally added 2 mM phenol at 37° C. and pH 7.3, injection volume of 20 µL, flow of 0.05 mL/min and run time 130 min. First reference of Blue dextran (>>5 MDa, $K_{AV}$ 0.0), Thyroglobulin (669 kDa, $K_{AV}$ 0.28), Ferritin (440 kDa, $K_{AV}$ 0.39), Ovalbumin (44.5 kDa, $K_{AV}$ 0.56), Ribonuclease (13.7 kDa, $K_{AV}$ 0.69) and a second reference of Albumin (66 kDa, $K_{AV}$ 0.53), Co(III)insulin-hexamer (35 kDa, $K_{AV}$ 0.61), and monomeric insulin X2 (6 kDa, $K_{AV}$ 0.73). Retention time of blue dextran was 17.9 min ($t_o$) and 0.74 min without column ($t_d$), and retention time of albumin (HSA) was about 34.1 min, $K_{AV} = (t - t_0)/(V_t/f + t_d - t_0)$ with t: retention time (min)

$t_0$: retention time of blue dextran (exclusion limit)

$t_d$: retention time of blue dextran without column (void volume)

$V_t$: total column volume (mL)

f: flow (mL/min)

Data Format:

| | |
|---|---|
| $K_{AV}$ peak1 | x.xx |
| Area peak1 (%) | xxx |
| $K_{AV}$ peak2 | x.xx |
| Area peak2 (%) | xxx |

$K_{AV}$ area peak1 is measured from $K_{AV}$=0 to $K_{AV}$=0.46 (32 min) as relative area % of total area for $K_{AV}$<0.46 corresponding to self association larger than albumin. For $K_{AV}$ peak 1 about 0.56 (albumin size) integration cut is between albumin size and insulin hexamer size.

SEC Method for Mix of Long Acting Insulin Derivative and Rapid Acting Insulin Aspart Using Specific Detection of Peak Fractions:

Miscibility of Insulin Aspart (3Zn/6ins) and prolonged acting insulin derivative 50:50, as measured by collecting fractions from SEC and quantifying by HPLC the presence of fast-acting and prolonged-acting insulins in the high molecular weight fraction (peak1) and in the low molecular weight fraction (peak2). Fraction cut is following integration cut mentioned above.

For SEC method without phenol in eluent peak1 contain associated forms larger than albumin and peak2 contain dihexameric, hexameric, dimeric and monomeric forms of insulin.

For SEC method including 2 mM phenol in the eluent peak1 contain dihexameric and other larger forms of insulin and peak2 contain hexameric, dimeric and monomeric forms of insulin.

Specific detection of insulin derivative and insulin aspart by HPLC reverse phase chromatography on a Zorbax Eclipse XDB-C18 2.1*15 mm (1.8 µm) gradient eluted with A: 0.2 M sodium sulphate, 0.04 M sodium phosphate, 10% acetonitrile, pH 7.2 and B: 70% acetonitrile at 30° C., 19-34% B in 4.5 min. linear, sudden initial condition at 5 min., run time of 7 min., flow of 0.5 ml/min., injection volume of 14 µL and UV detection at 276 nm using Insulin Aspart reference material for both analogues.

Data Format:

| | |
|---|---|
| Area insulin derivative peak1 (%) | xxx |
| Area insulin aspart peak2 (%) | xxx |

Results:

TABLE 1

| Formulation: neutral dissolution of insulin, glycerol 1.6%, 16 mM phenol and 16 mM m-cresol, zinc addition, sodium chloride 10 mM, phosphate 7 mM, pH 7.5 | SEC eluent: | Kav peak1 | Relative area % peak1 | Kav peak2 | Relative area % peak2 |
|---|---|---|---|---|---|
| B29Nε-hexadecandioyl-γ-Glu desB30 insulin 600 µM, 0 Zn/6ins, | Without phenol | — | 1 | 0.73 | 99 |
| B29Nε-hexadecandioyl-γ-Glu desB30 insulin 600 µM, 1 Zn/6ins | Without phenol | 0.11 | 25 | 0.73 | 75 |
| B29Nε-hexadecandioyl-γ-Glu desB30 insulin 600 µM, 2 Zn/6ins | Without phenol | 0.08 | 48 | 0.73 | 52 |
| B29Nε-hexadecandioyl-γ-Glu desB30 insulin 600 µM, 3 Zn/6ins, | Without phenol | 0.07 | 69 | 0.73 | 31 |
| B29Nε-hexadecandioyl-γ-Glu desB30 insulin 600 µM, 4 Zn/6ins | Without phenol | 0.06 | 86 | 0.74 | 14 |
| B29Nε-hexadecandioyl-γ-Glu desB30 insulin 600 µM, 5 Zn/6ins | Without phenol | 0.01 | 93 | 0.74 | 7 |
| B29Nε-hexadecandioyl-γ-Glu desB30 insulin 600 µM, 6 Zn/6ins | Without phenol | 0.00 | 96 | 0.74 | 4 |
| B29Nε-hexadecandioyl-γ-Glu desB30 insulin 600 µM, 0 Zn/6ins, | Phenol 2 mM | 0.54 | 17 | 0.72 | 83 |

TABLE 1-continued

| Formulation: neutral dissolution of insulin, glycerol 1.6%, 16 mM phenol and 16 mM m-cresol, zinc addition, sodium chloride 10 mM, phosphate 7 mM, pH 7.5 | SEC eluent: | Kav peak1 | Relative area % peak1 | Kav peak2 | Relative area % peak2 |
|---|---|---|---|---|---|
| B29Nε-hexadecandioyl-γ-Glu desB30 insulin 600 μM, 1 Zn/6ins | Phenol 2 mM | 0.54 | 56 | 0.73 | 44 |
| B29Nε-hexadecandioyl-γ-Glu desB30 insulin 600 μM, 2 Zn/6ins | Phenol 2 mM | 0.54 | 85 | 0.73 | 15 |
| B29Nε-hexadecandioyl-γ-Glu desB30 insulin 600 μM, 3 Zn/6ins, | Phenol 2 mM | 0.54 | 94 | 0.73 | 6 |
| B29Nε-hexadecandioyl-γ-Glu desB30 insulin 600 μM, 4 Zn/6ins | Phenol 2 mM | 0.54 | 97 | — | 3 |
| B29Nε-hexadecandioyl-γ-Glu desB30 insulin 600 μM, 5 Zn/6ins | Phenol 2 mM | 0.54 | 98 | — | 2 |
| B29Nε-hexadecandioyl-γ-Glu desB30 insulin 600 μM, 6 Zn/6ins | Phenol 2 mM | 0.54 | 98 | — | 2 |
| B29Nε-hexadecandioyl-γ-Glu desB30 insulin 600 μM, 0 Zn/6ins mixed with Insulin aspart 600 μM, 3 Zn/6ins 1:1 | Without phenol | 0.33 | Deriv. 33 | 0.73 | Aspart 94 |
| B29Nε-hexadecandioyl-γ-Glu desB30 insulin 600 μM, 1 Zn/6ins mixed with Insulin aspart 600 μM, 3 Zn/6ins 1:1 | Without phenol | 0.41 | Deriv. 34 | 0.74 | Aspart 89 |
| B29Nε-hexadecandioyl-γ-Glu desB30 insulin 600 μM, 2 Zn/6ins mixed with Insulin aspart 600 μM, 3 Zn/6ins 1:1 | Without phenol | 0.41 | Deriv. 39 | 0.74 | Aspart 91 |
| B29Nε-hexadecandioyl-γ-Glu desB30 insulin 600 μM, 3 Zn/6ins mixed with Insulin aspart 600 μM, 3 Zn/6ins 1:1 | Without phenol | 0.01 | Deriv. 89 | 0.74 | Aspart 98 |
| B29Nε-hexadecandioyl-γ-Glu desB30 insulin 600 μM, 4 Zn/6ins mixed with Insulin aspart 600 μM, 3 Zn/6ins 1:1 | Without phenol | 0.00 | Deriv. 98 | 0.73 | Aspart 100 |
| B29Nε-hexadecandioyl-γ-Glu desB30 insulin 600 μM, 5 Zn/6ins mixed with Insulin aspart 600 μM, 3 Zn/6ins 1:1 | Without phenol | 0.00 | Deriv. 98 | 0.73 | Aspart 100 |
| B29Nε-hexadecandioyl-γ-Glu desB30 insulin 600 μM, 6Zn/6ins mixed with Insulin aspart 600 μM, 3 Zn/6ins 1:1 | Without phenol | 0.00 | Deriv. 97 | 0.73 | Aspart 100 |
| B29Nε-hexadecandioyl-γ-Glu desB30 insulin 600 μM, 0 Zn/6ins mixed with Insulin aspart 600 μM, 3 Zn/6ins 1:1 | Phenol 2 mM | 0.55 | Deriv. 71 | 0.73 | Aspart 77 |
| B29Nε-hexadecandioyl-γ-Glu desB30 insulin 600 μM, 1 Zn/6ins mixed with Insulin aspart 600 μM, 3 Zn/6ins 1:1 | Phenol 2 mM | 0.55 | Deriv. 80 | 0.73 | Aspart 69 |
| B29Nε-hexadecandioyl-γ-Glu desB30 insulin 600 μM, 2 Zn/6ins mixed with Insulin aspart 600 μM, 3 Zn/6ins 1:1 | Phenol 2 mM | 0.55 | Deriv. 88 | 0.73 | Aspart 57 |
| B29Nε-hexadecandioyl-γ-Glu desB30 insulin 600 μM, 3 Zn/6ins mixed with Insulin aspart 600 μM, 3 Zn/6ins 1:1 | Phenol 2 mM | 0.55 | Deriv. 91 | 0.72 | Aspart 73 |
| B29Nε-hexadecandioyl-γ-Glu desB30 insulin 600 μM, 4 Zn/6ins mixed with Insulin aspart 600 μM, 3 Zn/6ins 1:1 | Phenol 2 mM | 0.54 | Deriv. 98 | 0.67 | Aspart 99 |
| B29Nε-hexadecandioyl-γ-Glu desB30 insulin 600 μM, 5 Zn/6ins mixed with Insulin aspart 600 μM, 3 Zn/6ins 1:1 | Phenol 2 mM | 0.54 | Deriv. 98 | 0.66 | Aspart 99 |
| B29Nε-hexadecandioyl-γ-Glu desB30 insulin 600 μM, 6 Zn/6ins mixed with Insulin aspart 600 μM, 3 Zn/6ins 1:1 | Phenol 2 mM | 0.54 | Deriv. 98 | 0.66 | Aspart 99 |

Conclusion: SEC (Size Exclusion Chromatography) using isotonic saline eluent at body temperature is used as a model for insulin self association after injection in subcutis when phenolic preservatives have disappeared. Including phenol in the eluent SEC evaluates the state of insulin self association in the pharmaceutical formulation and briefly upon injection.

B29Nε-hexadecandioyl-γ-Glu desB30 insulin 600 μM was formulated with zinc concentrations increasing stepwise by one from 0 to 6 Zn/6ins, and the SEC method showed self association to very high molecular weight and more than human albumin for more than 90%, when the zinc concentration was 5 Zn/6ins. Including phenol in the SEC eluent two sharp peaks were seen, at insulin dihexamer size and insulin monomer size, and at 4 Zn/6ins more than 95% was at dihexamer size.

All the formulations were mixed with insulin aspart (3 Zn/6ins) at equal concentration and volume and the content of the collected peaks were specifically analysed. At 4 Zn/6ins more than 95% of B29Nε-hexadecandioyl-γ-Glu desB30 insulin was found at very high molecular weight and more than 95% of aspart was found at monomer size. Including phenol in the eluent two peaks were seen, at insulin dihexamer size and insulin monomer size, and at 4 Zn/6ins more than 95% of the long acting insulin was at dihexamer size separated from more than 95% of insulin aspart centered between monomer and hexamer size. No blunting of the equimolar formulation mix was seen when the long acting analog formulation contained less than 5% of the monomeric form.

Example 5

Miscibility of B29Nε-Hexadecandioyl-γ-Glu desB30 Insulin with Insulin Aspart: Euglycaemic Clamp Studies in Pigs Formulation B29Nε-hexadecandioyl-γ-Glu desB30 insulin (ins.deriv.) (to 1200 μM) was suspended in water, dissolved and added glycerol 1.6%, and 16 mM phenol and 16 mM m-cresol. Before zinc addition pH was adjusted to 7.5 by sodium hydroxide, and zinc acetate added in smaller portions of max 1 Zn/6ins up to 3 Zn/6ins (ad I), to 5.62 Zn/6ins (ad II), and to 6 Zn/6ins (III). Sodium chloride was then added to 10 mM followed by adjustment of pH to 7.5 by sodium hydroxide, and adjustment of volume by water.

Insulin aspart (to 600 μM) was suspended in water and added hydrochloric acid to about pH 2.5, zinc acetate to 3 Zn/6ins, glycerol to 1.6%, 16 mM phenol and 16 mM m-cresol to sodium chloride to 10 mM, pH to 7.5 and water to final volume (IV).

Finally insulin aspart (IV) was mixed to B29Nε-hexadecandioyl-γ-Glu desB30 insulin in molar relation of 1:8 and total zinc concentration of 3.38 Zn/6ins.deriv.(I)(lowZnmix) and 6 Zn/6ins.deriv.(II)(highZnmix).

Animal Experiment

Figure 13:
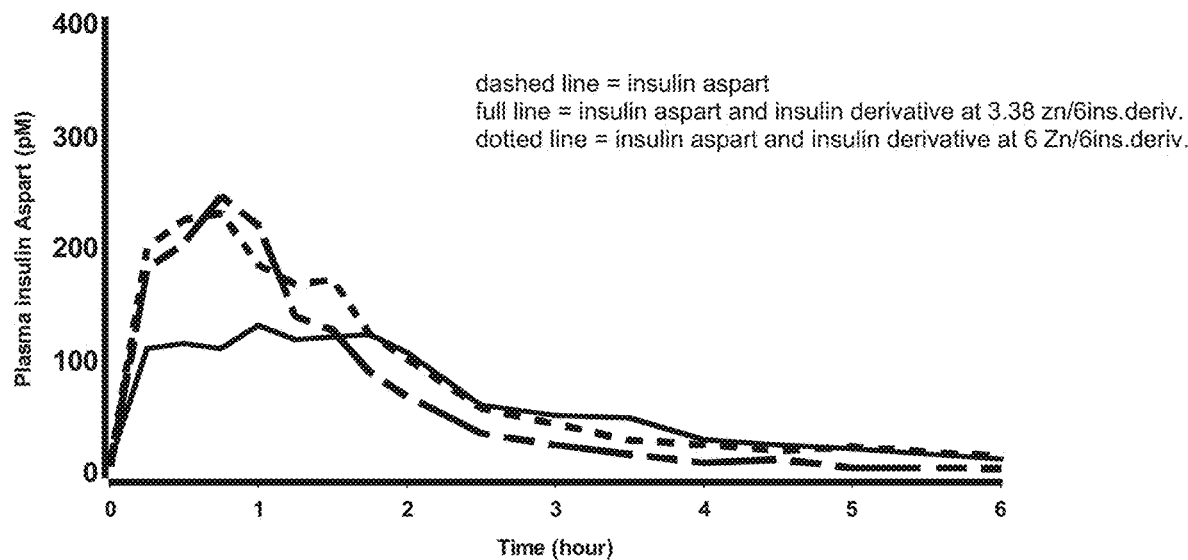
Figure 14:
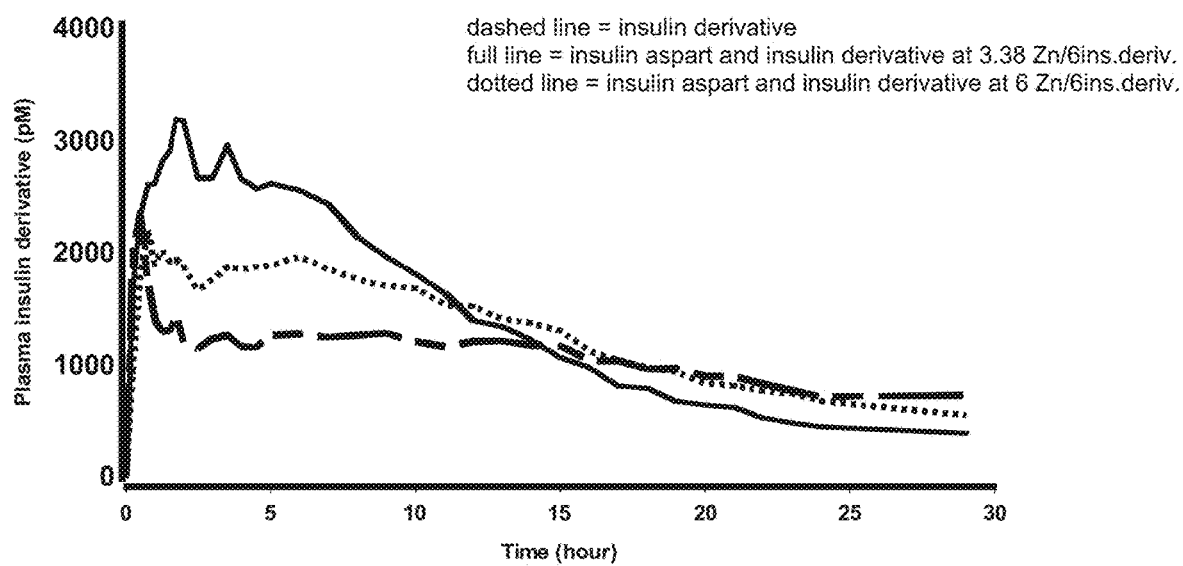
FIG. 14. Plasma profile of B29Nε-hexadecandioyl-γ-Glu desB30 insulin given separately (III, dashed line, N=8) and given in mix with insulin Aspart at low zinc concentration (I, 3.38 Zn/6ins.deriv., full line, N=8) and at high zinc concentration (II, 6 Zn/6ins.deriv., dotted line, N=7).

Female pigs (N=8, mean body weight 80 kg) were fasted 18 hours prior to the studies. To investigate the effect of mixing insulin aspart and B29Nε-hexadecandioyl-γ-Glu desB30 insulin, each pig received sc in random order either a lowZnmix (I) or a highZnmix (II) or the two analogues (III and IV) administered separately in the same pig. The doses were 0.9 nmol/kg of insulin aspart and 7.2 nmol/kg of B29Nε-hexadecandioyl-γ-Glu desB30 insulin. The pigs were kept euglycaemic at their individual fasting glucose levels by infusion of a 20% glucose solution. Dependent on changes in plasma glucose concentration adjustments of glucose infusion rate were made empirically. Blood samples were collected 0-24 h for specific ELISA plasma analysis of immunoreactive insulin, and the pharmacokinetic profiles are shown in FIG. 13 and FIG. 14.

Conclusion

The degree of blunting of both insulin components in the two mix preparations was examined. A marked blunting of both insulin aspart and insulin 454 was seen with low zinc concentration in the mix (3.38 Zn/6ins.deriv.). However, when the zinc concentration was increased to 6 zinc/6ins.deriv., no blunting of the pharmacokinetic profiles was observed. The glucose infusion rate compared well with the sum of the pharmacokinetic profiles of the individual insulin analogues.

Example 6

Citrate as Zinc Buffer

B29Nε-hexadecandioyl-γ-Glu des(B30) insulin (ins.deriv.)(to 600 μM) was suspended in water, dissolved and added glycerol 1.6%, phenol 16 mM, and m-cresol 16 mM. pH was adjusted to 7.5 by sodium hydroxide, and citrate was added in three formulations to 0.6, 1.8 and 6 mM respectively in connection with zinc acetate to 6 zinc/6 insulin deriv. Sodium chloride was then added to 10 mM and sodium phosphate (pH 7.5) to 5 mM followed by adjustment of pH to 7.5 or 7.8 by sodium hydroxide, and adjustment of volume by water.

The formulations were studied after storage 2 week at 37C compared to storage at 5C by the SEC method described in example 4 using an eluent with 2 mM phenol. Reference formulations without citrate at 3, 5 and 6 Zn/6ins.deriv. were included.

Miscibility of Insulin Aspart (3Zn/6ins) and prolonged acting insulin derivative 30:70, as measured by collecting fractions from SEC and quantifying by HPLC the presence of fast-acting and prolonged-acting insulins in the high molecular weight fraction (peak1) and in the low molecular weight fraction (peak2). Fraction cut and quantitation is following example 4.

Results:

TABLE 2

| Formulation: neutral dissolution of insulin deriv. 600 μM, glycerol 1.6%, phenol 16 mM, m-cresol 16 mM, citrate and zinc addition, sodium chloride 10 mM, phosphate 5 mM, pH 7.5 | SEC eluent: | Kav peak1 | Relative area % peak1 | Kav peak2 | Relative area % peak2 |
|---|---|---|---|---|---|
| Citrate 0.6 mM, 6 Zn/6ins. deriv., storage 5 C | +Phenol | 0.54 | 97 | 0.73 | 3 |
| Citrate 1.8 mM, 6 Zn/6ins. deriv., storage 5 C | +Phenol | 0.54 | 96 | 0.73 | 4 |
| Citrate 6.0 mM, 6 Zn/6ins. deriv., storage 5 C | +Phenol | 0.54 | 96 | 0.73 | 4 |
| Citrate 0 mM, 3 Zn/6ins. deriv., storage 5 C | +Phenol | 0.54 | 94 | 0.73 | 6 |
| Citrate 0 mM, 5 Zn/6ins. deriv., storage 5 C | +Phenol | 0.54 | 98 | 0.73 | 2 |
| Citrate 0 mM, 6 Zn/6ins. deriv., storage 5 C | +Phenol | 0.54 | 98 | 0.73 | 2 |
| Citrate 0.6 mM, 6 Zn/6ins. deriv., storage 2 w 37 C | +Phenol | 0.54 | 96 | 0.73 | 4 |

TABLE 2-continued

Formulation: neutral dissolution of insulin deriv. 600 µM, glycerol 1.6%, phenol 16 mM, m-cresol 16 mM, citrate and zinc addition, sodium chloride 10 mM, phosphate 5 mM, pH 7.5

| Sample | SEC eluent: | Kav peak1 | Relative area % peak1 | Kav peak2 | Relative area % peak2 |
|---|---|---|---|---|---|
| Citrate 1.8 mM, 6 Zn/6ins. deriv., storage 2 w 37 C | +Phenol | 0.54 | 96 | 0.73 | 4 |
| Citrate 6.0 mM, 6 Zn/6ins. deriv., storage 2 w 37 C | +Phenol | 0.54 | 95 | 0.73 | 5 |
| Citrate 0 mM, 3 Zn/6ins. deriv., storage 2 w 37 C | +Phenol | 0.54 | 93 | 0.73 | 7 |
| Citrate 0 mM, 5 Zn/6ins. deriv., storage 2 w 37 C | +Phenol | 0.54 | 98 | 0.73 | 2 |
| Citrate 0 mM, 6 Zn/6ins. deriv., storage 2 w 37 C | +Phenol | 0.54 | 98 | 0.73 | 2 |
| Citrate 0.6 mM, 6 Zn/6ins. deriv., pH 7.8, storage 2 w 37 C | +Phenol | 0.54 | 96 | 0.73 | 4 |
| Citrate 0.6 mM, 6 Zn/6ins. deriv., storage 5 C | +Phenol | 0.54 | Ins. deriv. 98 | 0.73 | Ins. aspart 97 |
| Citrate 1.8 mM, 6 Zn/6ins. deriv., storage 5 C | +Phenol | 0.54 | Ins. deriv. 97 | 0.73 | Ins. aspart 98 |
| Citrate 6.0 mM, 6 Zn/6ins. deriv., storage 5 C | +Phenol | 0.54 | Ins. deriv. 97 | 0.73 | Ins. aspart 98 |
| Citrate 0 mM, 3 Zn/6ins. deriv., storage 5 C | +Phenol | 0.54 | Ins. deriv. 95 | 0.73 | Ins. aspart 96 |
| Citrate 0 mM, 5 Zn/6ins. deriv., storage 5 C | +Phenol | 0.54 | Ins. deriv. 98 | 0.73 | Ins. aspart 99 |
| Citrate 0 mM, 6 Zn/6ins. deriv., storage 5 C | +Phenol | 0.54 | Ins. deriv. 97 | 0.73 | Ins. aspart 97 |
| Citrate 0.6 mM, 6 Zn/6ins. deriv., storage 2 w 37 C | +Phenol | 0.54 | Ins. deriv. 97 | 0.73 | Ins. aspart 96 |
| Citrate 1.8 mM, 6 Zn/6ins. deriv., storage 2 w 37 C | +Phenol | 0.54 | Ins. deriv. 97 | 0.73 | Ins. aspart 97 |
| Citrate 6.0 mM, 6 Zn/6ins. deriv., storage 2 w 37 C | +Phenol | 0.54 | Ins. deriv. 96 | 0.73 | Ins. aspart 97 |
| Citrate 0 mM, 3 Zn/6ins. deriv., storage 2 w 37 C | +Phenol | 0.54 | Ins. deriv. 93 | 0.73 | Ins. aspart 79 |
| Citrate 0 mM, 5 Zn/6ins. deriv., storage 2 w 37 C | +Phenol | 0.54 | Ins. deriv. 98 | 0.73 | Ins. aspart 97 |
| Citrate 0 mM, 6 Zn/6ins. deriv., storage 2 w 37 C | +Phenol | 0.54 | Ins. deriv. 98 | 0.73 | Ins. aspart 96 |

Conclusion:

Using a SEC isotonic saline eluent comprising 2 mM phenol the long acting insulin derivative is predominantly associated at a size of albumin corresponding to a dihexameric form (and not higher associated forms), and the amount of insulin derivative in the monomeric form is decreased at zinc concentration increased from 3 to 5 and 6 Zn/6ins.deriv. Adding 1, 3 or 10 citrate equivalents to the zinc concentration at 6 Zn/6ins.deriv. showed less content of the monomeric insulin derivative compared to a reference at 3 Zn/ins.deriv. The self associating pattern was not changed after storage 2 weeks at 37° C.

Miscibility of Insulin Aspart (3Zn/6ins) formulated without citrate and prolonged acting insulin derivative formulated as shown in the series above in this example—in the molar proportion of 30:70—is shown in the table after storage at 5 C and 2 weeks at 37 C. The insulin derivative formulations comprising citrate at three levels and 6 Zn/6ins were shown to be mixable with insulin aspart after 2 weeks storage at 37 C, whereas insulin aspart was partly included in the high molecular weight fraction at the normal level of zinc at 3 Zn/6ins.

Example 7

Zinc Citrate is Added

B29Nε-hexadecandioyl-γ-Glu desB30 insulin (ins.deriv.) (to 600 µM) is suspended in water, dissolved, (if needed by addition of sodium hydroxide), and added glycerol 1.6%, phenol 16 mM, and m-cresol 16 mM. pH is adjusted to 7.5 by sodium hydroxide, and zinc citrate is added to 0.6 mM Zinc ion. Sodium chloride is then added to 10 mM and sodium phosphate (pH 7.5) to 5 mM followed by adjustment of pH to 7.5 and adjustment of volume by water.

Example 8

A Surfactant is Added and Mixtures with Rapid Acting Analogues

B29Nε-hexadecandioyl-γ-Glu desB30 insulin (ins.deriv.) (to 600 μM) is suspended in water, dissolved and added glycerol 1.6%, and 16 mM phenol and 16 mM m-cresol. pH is adjusted to 7.5 by sodium hydroxide, and zinc acetate to 6 zinc/6 insulin deriv. (optionally zinc as citrate). Sodium chloride is then added to 10 mM, a surfactant eg. poloxamer 188 or polysorbate 20 to about 0.002% and sodium phosphate (pH 7.5) to 5 mM followed by adjustment of pH to 7.5 and adjustment of volume by water.

Insulin Aspart (AspB28 human insulin) or Insulin L isPro (LysB28ProB29 human insulin) or Insulin Glulisine (LysB3 GluB29 human insulin) (all 600 μM) are mixed with B29Nε-hexadecandioyl-γ-Glu desB30 insulin formulated according to example 7 or to example 8 in a molar relation about 3/7 to about 7/3.

Example 9

Table 3 shows SEC, measured as described in example 4 with 2 or 6 Zn(II) per 6 insulins. For preparation of the compounds mentioned in the table, see WO2006/082204 and WO2006/082205

TABLE 3

| Formulation: neutral dissolution of 600 μM insulin, glycerol 1.6%, phenol 16 m, m-cresol 16 mM, 2 or 6 zinc/hexamer, sodium chloride 10 mM, phosphate 7 mM, pH 7.5 | Kav 2 Zn peak 1 | Relative area % peak 1 | Kav 6 Zn peak 1 | Relative area % peak 1 |
|---|---|---|---|---|
| B29Nε-(4-{[(2-Carboxy-ethyl)-(15-carboxy-pentadecanoyl)-amino]-methyl}-benzoyl) desB30 human insulin | 0.01 | 84 | 0.00 | 98 |
| B29Nε-hexadecandioyl-gamma-Glu-(3-(2-{2-[2-(2-amino-ethoxy)-ethoxy]-ethoxy}-ethoxy)-propionyl desB30 human insulin | 0.09 | 79 | 0.06 | 89 |
| B29Nε-(4-{[(2-Carboxy-ethyl)-(14-carboxy-tetradecanoyl)-amino]-methyl}-benzoyl) desB30 human insulin | 0.09 | 55 | 0.00 | 96 |
| B29Nε-[(5-{[(2-Carboxy-ethyl)-(15-carboxy-pentadecanoyl)-amino]-methyl}-furan-2-carbonyl) desB30 human insulin | 0.02 | 81 | 0.03 | 96 |
| B29Nε-hexadecandioyl-gamma-Glu-(4-aminomethyl-benzoyl) desB30 human insulin | 0.15 | 48 | 0.00 | 97 |
| B29Nε-(2-{[(2-Carboxy-ethyl)-(15-carboxy-pentadecanoyl)-amino]-methyl}-benzoyl) desB30 human insulin | 0.16 | 54 | 0.03 | 93 |

Example 10

Preparation of 1,16-Hexadecanedioic Acid Mono Benzyl Ester

Hexadecanedioic acid (20.0 g, 69.8 mmol), n-octane and Dowex® are suspended and heated to reflux. Benzyl formate (22.0 g, 162 mmol) is added. After 6 hours additional benzyl formate (22.0 g, 162 mmol) is added. The heating is continued for 50 hours. The reaction mixture is filtered at 80° C. The filtrate is cooled to 20° C., and the precipitate is collected by filtration. The crude product (20.2 g) is suspended in dichloromethane (220 ml) at 20° C. for 4 hours. The suspension is filtered, and the filtrate is evacuated to dryness at 20-30° C. The resulting solid (13.9 g) is recrystallised from 2-propanol (140 ml).

The product is isolated by filtration, and dried to constant weight under reduced pressure at 30-40° C. Yield: 10.2 g (39%) of white material.

Preparation of L-2-(15-benzyloxycarbonyl-pentadecanoylamino)-pentanedioic acid 5-benzyl ester 1-(2,5-dioxo-pyrrolidin-1-yl) ester 1,16-hexadecanedioic acid mono benzyl ester (20.0 g, 53.1 mmol) is dissolved in acetone at 35-40° C. N-Hydroxysuccinimide (6.42 g/55.8 mmol) is added. To the resulting solution dicyclohexylcarbodiimide (DCC) (12.1 g/58.4 mmol) is added. The reaction mixture is stirred for 3-4 hours at 35° C. To the resulting suspension triethylamine (7.40 ml, 53.1 mmol) og L-glutamic acid a-benzyl ester (12.6 g/53.1 mmol) are added. The reaction mixture is stirred for 8-16 hours at 35-40° C. The reaction mixture is cooled to 20-25° C. Methanesulfonic acid (3.45 ml/53.1 mmol) and DCC (12.1 g/53.1 mmol) are added. The reaction mixture is stirred for 8-16 hours at 20-25° C. The reaction mixture is filtered, and the filtrate evacuated to dryness. The residue is partitioned between water (100 ml) and toluene (200 ml). The toluene phase is dried by distilling of water. Silica gel (20 g) is added to the residue. The suspension is stirred for 30 minutes at 20-25° C., then filtered. The volume of the filtrate is reduced to ca 100-120 ml by evaporation under reduced pressure. N-heptane (150 ml) is added over a period of 15-30 minutes. The resulting suspension is stirred for 2 hours. The product is isolated by filtration, and dried to constant weight under reduced pressure at 20-25° C. Yield 21 g (58%) of white material.

Preparation of L-2-(15-carboxy-pentadecanoylamino)-pentanedioic acid 5-(2,5-dioxo-pyrrolidin-1-yl) ester (PC2414)

L-2-(15-benzyloxycarbonyl-pentadecanoylamino)-pentanedioic acid 5-benzyl ester 1-(2,5-dioxo-pyrrolidin-1-yl) ester (5.0 g, 7.3 mmol) is dissolved in acetone (95 ml)

containing trifluoroacetic acid (95 µl). Palladium on carbon, 10% (0.50 g) is added. Under stirring at 30-35° C. hydrogen is added. When the consumption of hydrogen stops the reaction mixture is filtered. The filtrate is cooled to 20° C. and n-heptane (140 ml) is added over a period of 15-30 minutes. The resulting suspension is cooled to 0-5° C. for 2-3 hours. The product is isolated by filtration, and dried to constant weight under reduced pressure at 20-25° C. Yield 3 g (84%) of white material.

The product is analysed by proton NMR (Bruker 600 MHz) using acetone-d6 as solvent.

Proton NMR assignments from the 1D spectrum (internal reference is TMS at δ 0.0 ppm)

| $^1H$ | Chemical Shift δ (ppm) | Integral | Coupling Pattern | Coupling Constants $^nJ_{HH}$ (Hz) |
|---|---|---|---|---|
| H2 | 2.28 | 2H | t | $^3J_{HH}$ = 7.5 |
| H3/H14 | 1.60 | 4H | m | ND |
| H4-H13 | 1.29 | 20H | m | ND |
| H15 | 2.26 | 2H | dt | $^2J_{HH}$ = 2.5, $^3J_{HH}$ = 7.5 |
| H17 | 4.59 | 1H | ddd | $^3J_{HH}$ = 8.0/7.5/5.2 |
| H19 | 2.31/2.10 | 2H | m | ND |
| H20 | 2.82/2.75 | 2H | ddd | $^2J_{HH}$ = 16.5, $^3J_{HH}$ = 10.0/6.0 |
| H23/H24 | 2.88 | 4H | s | — |
| NH | 7.37 | 1H | d | $^3J_{HH}$ = 7.5 |

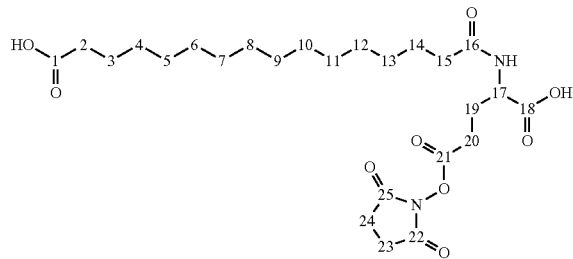

Acylation of the Human Insulin desB30 ε-Aminogroup in Lysine in Position B29 with PC2414

4 g of desB30 human insulin is suspended in 64 g of purified water. 1.85 ml of triethyl amine (TEA) is added to dissolve desB30 human insulin and to raise the pH to 11.4-12.0. The solution is cooled to 2-5° C.

448 mg of PC2414 is dissolved in 3.5 g NMP (N-methyl-2-pyrrolidon) stabilised with 10 µl 5% sulphuric acid.

The desB30 human insulin solution is stirred and the PC2414 solution is added over a 20 min period, while keeping the temperature low.

After the addition of PC2414 the reaction mixture is diluted with 2.5 weight of a solution consisting of: Tris-hydroxymethylaminomethan (20 mmol/kg), Ammonium acetate (30 mmol/kg), ethanol 42.5% w/w, the rest purified water, pH 7.5

After dilution the pH is adjusted to 7.5 by slowly adding 1 M acetic acid, while stirring.

Analysis by HPLC demonstrates the formation of 72.11% Lys$^{B29}$(Nε-hexadecandioyl-γ-glutamyl) des(B30) human insulin with 14.22% residual desB30 human insulin.

Analytical HPLC Method:

A 150×4.6 mm I.D. column packed with a octyldimethylsilyl substituted silica having pore size of about 100 A and particle diameter of about 3.5 µm and equilibrated at 40° C. at a flow rate of 1 ml/min with a mixture consisting of 1: a buffer of 20 mM NaH$_2$PO$_4$.H$_2$O and 100 mmol Na$_2$SO$_4$ adjusted to pH 5.9 with NaOH in the aqueous buffer containing 7.8% (w/w) and 2: acetonitrile solvent containing 42.8% w/w acetonitrile, to make 25% (w/w) acetonitrile.

Lys$^{B29}$(Nε-hexadecandioyl-γ-glutamyl) des(B30) human insulin emerged from the column after about 20 min. desB30 human insulin emerged from the column after about 6 min.

Assay (II)

Potency of the Insulin Derivatives of the Invention Relative to Human Insulin

Sprague Dawley male rats weighing 238-383 g on the experimental day were used for the clamp experiment. The rats had free access to feed under controlled ambient conditions and were fasted overnight (from 3 µm) prior to the clamp experiment.

Experimental Protocol

The rats were acclimatized in the animal facilities for at least 1 week prior to the surgical procedure. Approximately 1 week prior to the clamp experiment Tygon catheters were inserted under halothane anaesthesia into the jugular vein (for infusion) and the carotid artery (for blood sampling) and exteriorised and fixed on the back of the neck. The rats were given Streptocilin vet. (Boehringer Ingelheim; 0.15 ml/rat, i.m.) post-surgically and placed in an animal care unit (25° C.) during the recovery period. In order to obtain analgesia, Anorphin (0.06 mg/rat, s.c.) was administered during anaesthesia and Rimadyl (1.5 mg/kg, s.c.) was administered after full recovery from the anaesthesia (2-3 h) and again once daily for 2 days.

The clamp technique employed was adapted from (1). At 7 am on the experimental day overnight fasted (from 3 µm the previous day) rats were weighed and connected to the sampling syringes and infusion system (Harvard 22 Basic pumps, Harvard, and Perfectum Hypodermic glass syringe, Aldrich) and then placed into individual clamp cages where they rested for ca. 45 min before start of experiment. The rats were able to move freely on their usual bedding during the entire experiment and had free access to drinking water. After a 30 min basal period during which plasma glucose levels were measured at 10 min intervals, the insulin derivative to be tested and human insulin (one dose level per rat, n=6-7 per dose level) were infused (i.v.) at a constant rate for 300 min. Plasma glucose levels were measured at 10 min intervals throughout and infusion of 20% aqueous glucose was adjusted accordingly in order to maintain euglyceamia. Samples of re-suspended erythrocytes were pooled from each rat and returned in about ½ ml volumes via the carotid catheter.

On each experimental day, samples of the solutions of the individual insulin derivatives to be tested and the human insulin solution were taken before and at the end of the clamp experiments and the concentrations of the peptides were confirmed by HPLC. Plasma concentrations of rat insulin and C-peptide as well as of the insulin derivative to be tested and human insulin were measured at relevant time points before and at the end of the studies. Rats were killed at the end of experiment using a pentobarbital overdose.

Assay (III)

Determination in Pigs of T$_{50}$% of the Insulin Derivatives of the Invention

T$_{50\%}$ is the time when 50% of an injected amount of the A14 Tyr[$^{125}$I] labelled derivative of an insulin to be tested has disappeared from the injection site as measured with an external γ-counter.

The principles of laboratory animal care were followed, Specific pathogen-free LYYD, non-diabetic female pigs, cross-breed of Danish Landrace, Yorkshire and Duroc, were used (Holmenlund, Haarloev, Denmark) for pharmacokinetic and pharmacodynamic studies. The pigs were conscious, 4-5 months of age and weighing 70-95 kg. The animals were fasted overnight for 18 h before the experiment.

Formulated preparations of insulin derivatives labelled in Tyr$^{A14}$ with $^{125}$I were injected sc. in pigs as previously described (Ribel, U., Jorgensen, K, Brange, J, and Henriksen, U. The pig as a model for subcutaneous insulin absorption in man. Serrano-Rios, M and Lefébvre, P. J. 891-896. 1985. Amsterdam; New York; Oxford, Elsevier Science Publishers. 1985 (Conference Proceeding)).

At the beginning of the experiments a dose of 60 nmol of the insulin derivative according to the invention (test compound) and a dose of 60 nmol of insulin detemir (both $^{125}$I labelled in Tyr A14) were injected at two separate sites in the neck of each pig.

The disappearance of the radioactive label from the site of sc. injection was monitored using a modification of the traditional external gamma-counting method (Ribel, U. Subcutaneous absorption of insulin analogues. Berger, M. and Gries, F. A. 70-77 (1993). Stuttgart; New York, Georg Thime Verlag (Conference Proceeding)). With this modified method it was possible to measure continuously the disappearance of radioactivity from a subcutaneous depot for several days using cordless portable device (Scancys Laboratorieteknik, Vrlose, DK-3500, Denmark). The measurements were performed at 1-min intervals, and the counted values were corrected for background activity.

The invention claimed is:

1. A pharmaceutical formulation comprising:
   LysB29(N$^\varepsilon$-hexadecandioyl-γ-Glu)des(B30) human insulin;
   a ratio of zinc to LysB29(N$^\varepsilon$-hexadecandioyl-γ-Glu)des(B30) human insulin of 5.5 to 12 zinc atoms per 6 molecules of LysB29(N$^\varepsilon$-hexadecandioyl-γ-Glu)des(B30) human insulin; and
   a pharmaceutically acceptable carrier and excipients;
   wherein the excipients include a preservative selected from phenol, m-cresol, or mixtures thereof, and wherein the formulation is soluble at physiological pH.

2. A pharmaceutical formulation comprising:
   LysB29(N$^\varepsilon$-hexadecandioyl-γ-Glu)des(B30) human insulin;
   a ratio of zinc to LysB29(N$^\varepsilon$-hexadecandioyl-γ-Glu)des(B30) human insulin of from 5.5 to 6 zinc atoms per 6 molecules of LysB29(N$^\varepsilon$-hexadecandioyl-γ-Glu)des(B30) human insulin; and
   a pharmaceutically acceptable carrier and excipients;
   wherein the formulation is soluble at physiological pH, and
   wherein zinc-LysB29(N$^\varepsilon$-hexadecandioyl-γ-Glu)des(B30) human insulin aggregates, having a molecular weight greater than that of thyroglobulin (669 kDa) as measured by size exclusion chromatography, are formed subcutaneously following administration to a subject in need thereof.

3. A pharmaceutical formulation comprising:
   a) LysB29(N$^\varepsilon$-hexadecandioyl-γ-Glu)des(B30) human insulin;
   b) a ratio of zinc to LysB29(N$^\varepsilon$-hexadecandioyl-γ-Glu)des(B30) human insulin of 5.5 to 12 zinc atoms per 6 molecules of LysB29(N$^\varepsilon$-hexadecandioyl-γ-Glu)des(B30) human insulin; and
   c) a pharmaceutically acceptable carrier and excipients, wherein the excipients include a preservative selected from phenol, m-cresol, or mixtures thereof;
   wherein the formulation is soluble at physiological pH; and wherein, after the pharmaceutical formulation is administered subcutaneously to a subject in need thereof, zinc-LysB29(N$^\varepsilon$-hexadecandioyl-γ-Glu)des(B30) human insulin aggregates are formed subcutaneously, said aggregates having a molecular weight greater than that of thyroglobulin (669 kDa) as measured by size exclusion chromatography.

4. The pharmaceutical formulation according to claim 1 comprising 5.5 zinc atoms per 6 molecules of LysB29(N$^\varepsilon$-hexadecandioyl-γ-Glu)des(B30)human insulin.

5. The pharmaceutical formulation according to claim 1 comprising 6 zinc atoms per 6 molecules of LysB29(N$^\varepsilon$-hexadecandioyl-γ-Glu)des(B30)human insulin.

6. The pharmaceutical formulation according to claim 3 comprising 5.5 zinc atoms per 6 molecules of LysB29(N$^\varepsilon$-hexadecandioyl-γ-Glu)des(B30)human insulin.

7. The pharmaceutical formulation according to claim 3 comprising 6 zinc atoms per 6 molecules of LysB29(N$^\varepsilon$-hexadecandioyl-γ-Glu)des(B30)human insulin.

* * * * *